United States Patent
Smith

(10) Patent No.: US 11,299,535 B2
(45) Date of Patent: Apr. 12, 2022

(54) HUMAN IGE ANTIBODIES BINDING TO ASPERGILLUS ALLERGENS

(71) Applicant: VANDERBILT UNIVERSITY, Nashville, TN (US)

(72) Inventor: Scott A. Smith, Nashville, TN (US)

(73) Assignee: VANDERBILT UNIVERSITY, Nashville, TN (US)

(*) Notice: Subject to any disclaimer, the term of this patent is extended or adjusted under 35 U.S.C. 154(b) by 0 days.

(21) Appl. No.: 16/653,147

(22) Filed: Oct. 15, 2019

(65) Prior Publication Data

US 2020/0115439 A1  Apr. 16, 2020

Related U.S. Application Data

(60) Provisional application No. 62/746,437, filed on Oct. 16, 2018.

(51) Int. Cl.
| | | |
|---|---|---|
| *C07K 16/14* | (2006.01) | |
| *G01N 33/569* | (2006.01) | |
| *A61K 39/00* | (2006.01) | |
| *A61P 31/10* | (2006.01) | |
| *C07K 14/47* | (2006.01) | |

(52) U.S. Cl.
CPC .......... *C07K 16/14* (2013.01); *A61K 39/0002* (2013.01); *A61P 31/10* (2018.01); *C07K 14/47* (2013.01); *G01N 33/56961* (2013.01); *C07K 2317/24* (2013.01); *C07K 2317/31* (2013.01); *C07K 2317/54* (2013.01); *C07K 2317/55* (2013.01); *C07K 2317/565* (2013.01); *C07K 2317/622* (2013.01); *C07K 2317/94* (2013.01); *C07K 2319/30* (2013.01)

(58) Field of Classification Search
None
See application file for complete search history.

(56) References Cited

U.S. PATENT DOCUMENTS 10,479,825 B2 * 11/2019 Crowe .................. C07K 16/10

FOREIGN PATENT DOCUMENTS

WO   WO 2018/144425   8/2018

OTHER PUBLICATIONS

Wurth et al. (American Journal of Respiratory Critical Care Medicine, 2017 195:A3210).*
Esch RE. Manufacturing and standardizing fungal allergen products. *J Allergy Clin Immunol.* 2004;113(2):210-215.
Kuwabara K, Hirose M, Kato K, Yokoi T, Shiga M, Kondo R, Nakamura M, Matsunaga K, Horiguchi T. Serological analysis of sensitization in allergic bronchopulmonary aspergillosis: a study on allergen components and interspecies relationships. *J Asthma.* Jun. 2020;57(6):610-617. [Abstract].
Vailes L, Sridhara S, Cromwell O, Weber B, Breitenbach M, Chapman M. Quantitation of the major fungal allergens, Alt a 1 and Asp f 1, in commercial allergenic products. *J Allergy Clin Immunol.* 2001;107(4):641-646.
Wurth, Mark A., et al. "Human IgE mAbs define variability in commercial Aspergillus extract allergen composition." *JCI Insight* 3.20 (2018).
Hessell, Ann J., et al. "Fc receptor but not complement binding is important in antibody protection against HIV." *Nature* 449.7158 (2007): 101-104.
Hezareh, Marjan, et al. "Effector function activities of a panel of mutants of a broadly neutralizing antibody against human immunodeficiency virus type 1." *Journal of Virology* 75.24 (2001): 12161-12168.
Niwa, Rinpei, et al. "IgG subclass-independent improvement of antibody-dependent cellular cytotoxicity by fucose removal from Asn297-linked oligosaccharides." *Journal of immunological methods* 306.1-2 (2005): 151-160.

* cited by examiner

*Primary Examiner* — Robert A Zeman
(74) *Attorney, Agent, or Firm* — Parker Highlander PLLC

(57) ABSTRACT

The present disclosure is directed to antibodies binding to *Aspergillus* allergens and methods for use thereof.

Figure 1:
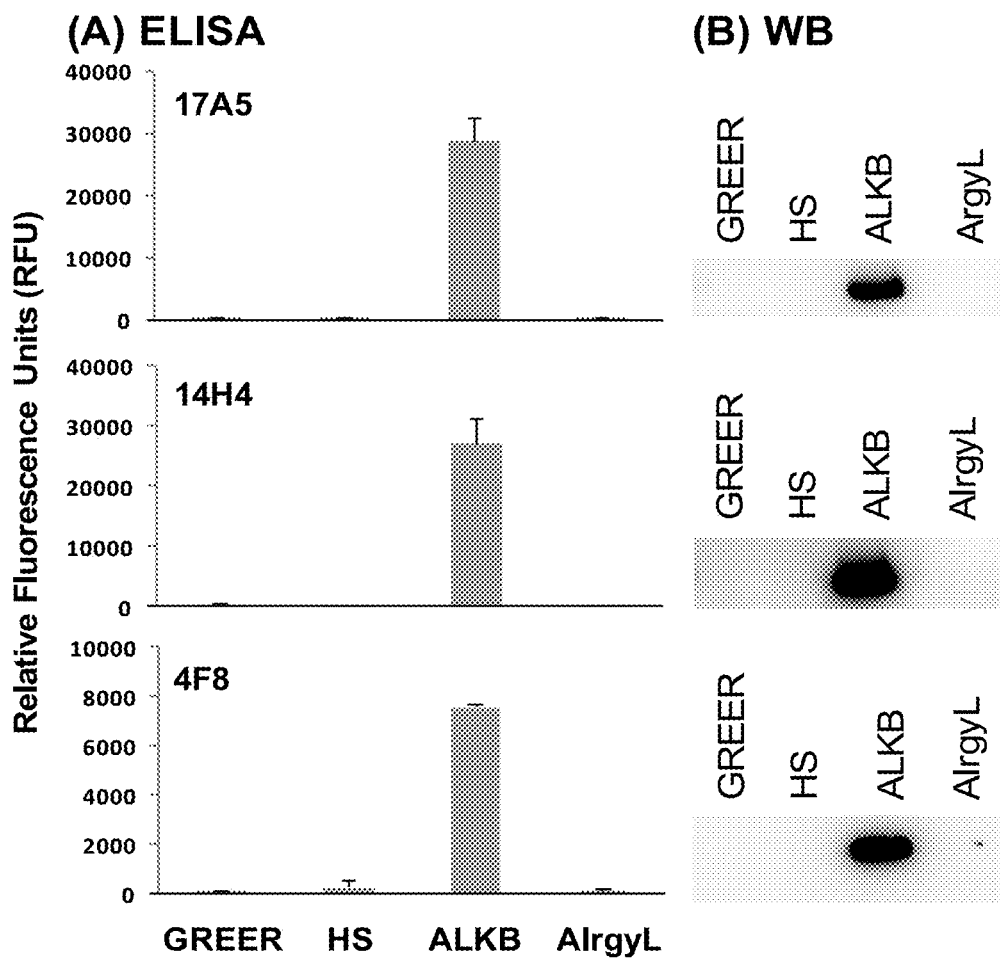

13 Claims, 2 Drawing Sheets
(1 of 2 Drawing Sheet(s) Filed in Color)
Specification includes a Sequence Listing.

FIGS. 1A-B

SEQUENCE LISTING

```
<160> NUMBER OF SEQ ID NOS: 134

<210> SEQ ID NO 1
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 1
caggtgcagc tggtggagtc tggggggaggc ttggtcaagc ctggggggtc cctgagactc      60
tcctgtgcag cctctggatt cccctttcagt gattatcaca tgacctggat ccgccaggct     120
ccggggaagg ggctggaatg gatttcacac atcagtagtc tggcaataa gatacattac       180 gcagagtctg tgaagggccg gttcaccata tccagggaca acgccaagaa ttctctgttt      240
ctgcacatga acagcctgag agccgaggac acggccatgt attactgtgc cagagatgcg      300
ggatattatc atggttcggg gaataatgca atttatcacg gtatggacgt ctggggccag      360
gggaccacgg tcaccgtctc ctca                                              384

<210> SEQ ID NO 2
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 2
cagtctgtgt tgacgcagcc gccctcagtg tctgcggccc caggacagag ggtcaccatc      60
tcctgctctg gcggcagttc caacattggt tataattatg tggcctggta ccagcaattc      120
ccaggaacag cccccaaact cctcctctat gacgatgatg agcggccctc tggcattcct      180
gaccgattct ctggctccag gtctggcacg tcagccaccc tggtcatcac cggactccag      240
actggggacg aggccgacta ctactgcgga acttgggata gtagcctgtc tgttgtggtg      300
ttcggcgggg ggaccaggct gaccgtccta g                                      331

<210> SEQ ID NO 3
<211> LENGTH: 382
<212> TYPE: DNA
<213> ORGANISM: Artificial sequence
<220> FEATURE:
<223> OTHER INFORMATION: Synthetic oligonucleotide

<400> SEQUENCE: 3
gaggtgcagc tggtgcagtc tggagcagag gtgaagaggg ccggggagtc tctgaagatc      60
```

```
tcctgtaagg gttctggata ccccttttgcc acctactggg tcggctgggt gcgccagatg    120
cccggaaaag gcctggaatg gatgactatc atctatcctg aggactccga caccagatac    180
agcccgtcct tccaagacca tgtcaccatc tcagccgaca agtccctcag caccgcctac    240
ctgcagtgga gcagcctaaa ggcctcggac acagccatgt attactgtgc gagagtgtcc    300
cggtattatt atgatagtag aagttattac cctgatgctt ttgacatctg gggccaaggg    360
acaatggtca ccgtctcctc ag                                             382

<210> SEQ ID NO 4
<211> LENGTH: 319
<212> TYPE: DNA
<213> ORGANISM: Artificial sequence
<220> FEATURE:
<223> OTHER INFORMATION: Synthetic oligonucleotide

<400> SEQUENCE: 4
tcctatgagc tgactcagcc accctcagtg tccgtgtccc caggacagac agccagcatc     60
acctgctctg gagataaatt gggggataaa tatgtttgct ggtatcaaca gaagccaggc    120
cggtcccctg tgttggtcgt ccatcaagat accaagcggc cctcagggat ccctgagcga    180
ttctctggct ccaattctgg ggacacagcc actctgacca tcagcgggac ccaggctatg    240
gatgaggctg actattactg tcaggcgtgg gacagtacca ttggggtctt cgggcctggg    300
accagggtca ccgtcctag                                                 319

<210> SEQ ID NO 5
<211> LENGTH: 355
<212> TYPE: DNA
<213> ORGANISM: Artificial sequence
<220> FEATURE:
<223> OTHER INFORMATION: Synthetic oligonucleotide

<400> SEQUENCE: 5
caggtgcagc tacaggagtg gggcgcagga ctgttgaagc cctcggagac cctgtccctc     60
acctgcgctg tctatggtgg gtccttcagt gattactact ggaactggat ccgccagccc    120
ccagggaagg gctggagtg gattggagac atcactcaca gtggagccac caactacaac    180
ccgtccctca cgagtcgagt caccttctca gtagacattt ctaagaacca ctttttccttg    240 aagctgacct ctgtgaccgc cgcggacacg gctatgtact actgtgcgag aataggagaa    300
aaaactggtg attatacaat ctggggccaa gggacaatgg tcaccgtctc ctcag         355

<210> SEQ ID NO 6
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 6
gccatccaga tgacccagtc tccatcgtcc ctgtctgcat ctataggaga cagagtcacc     60
atcacttgcc gggcaagtca gggcattaga aataatttag ctggtatca gcaggcacca    120 gggaaagccc ctaggctcct gatctatgct gcatccagtt tacaaagtga cgtcccatca    180
aggttcagcg gcagtgggtc tggcacagat ttcactctca ccatcagcgc cctgcagcct    240
gaagattttg caacttatta ctgtctacaa gactacaatt accctcggac gttcggccaa    300
gggaccaagg tggaaatcaa ac                                             322
```

-continued

```
<210> SEQ ID NO 7
<211> LENGTH: 363
<212> TYPE: DNA
<213> ORGANISM: Artificial sequence
<220> FEATURE:
<223> OTHER INFORMATION: Synthetic oligonucleotide

<400> SEQUENCE: 7
gaggtgcagc tggtggagtc tgggggaggc ttggtccagc cggggggtc cctgaaactc      60 tcctgtgcag tctctgggtt cagcgtcagt gactctgcta tacactgggt ccgccaggct    120
tccgggaaag gactggagtg ggtaggccac atgcgaagtc aggcgaacag ttacgcgaca    180
gcctatggtg cgtcggtgag aggcaggttc aacatctcca gagatgactc aaagaacacg    240
gcatatctgc aaatgaacag cctgaacatc gatgacacgg ccgtatatta ttgtactaga    300
aaggtggata tcgacacgg aatggacgtc tggggccaag gaccacggt caccgtctcc      360 tca                                                                  363

<210> SEQ ID NO 8
<211> LENGTH: 324
<212> TYPE: DNA
<213> ORGANISM: Artificial sequence
<220> FEATURE:
<223> OTHER INFORMATION: Synthetic oligonucleotide

<400> SEQUENCE: 8
tcctatgtgt tgacgcagcc tccctctgtg tcagtggccc caggacagac ggccaggatt     60
ccctgtgggg gaaacagcat tgggagtaga agtgtgcact ggtaccagca gaagccaggc    120
cgggcccctg tgttggtcat ctattatgat agggaccggc cctcggggat ccctgagcga    180
ttctctggct ccaactctgg gaacacggcc accctgacca tcgacagggt cgaggccggg    240
gatgaggccg actactactg tcaggtgtgg gatggtagta gcgaccaata tgtcttcgga    300
attgggacca aggtcaccgt ccta                                           324

<210> SEQ ID NO 9
<211> LENGTH: 128
<212> TYPE: PRT
<213> ORGANISM: Artificial sequence
<220> FEATURE:
<223> OTHER INFORMATION: Synthetic amino acid

<400> SEQUENCE: 9

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Pro Phe Ser Asp Tyr
            20                  25                  30

His Met Thr Trp Ile Arg Gln Ala Pro Gly Lys Gly Leu Glu Trp Ile
        35                  40                  45

Ser His Ile Ser Ser Ala Gly Asn Lys Ile His Tyr Ala Glu Ser Val
    50                  55                  60

Lys Gly Arg Phe Thr Ile Ser Arg Asp Asn Ala Lys Asn Ser Leu Phe
65                  70                  75                  80

Leu His Met Asn Ser Leu Arg Ala Glu Asp Thr Ala Met Tyr Tyr Cys
                85                  90                  95

Ala Arg Asp Ala Gly Tyr Tyr His Gly Ser Gly Asn Asn Ala Ile Tyr
           100                 105                 110

His Gly Met Asp Val Trp Gly Gln Gly Thr Thr Val Thr Val Ser Ser
       115                 120                 125
```

```
<210> SEQ ID NO 10
<211> LENGTH: 110
<212> TYPE: PRT
<213> ORGANISM: Artificial sequence
<220> FEATURE:
<223> OTHER INFORMATION: Synthetic amino acid

<400> SEQUENCE: 10

Gln Ser Val Leu Thr Gln Pro Pro Ser Val Ser Ala Ala Pro Gly Gln
1               5                   10                  15

Arg Val Thr Ile Ser Cys Ser Gly Gly Ser Ser Asn Ile Gly Tyr Asn
            20                  25                  30

Tyr Val Ala Trp Tyr Gln Gln Phe Pro Gly Thr Ala Pro Lys Leu Leu
        35                  40                  45

Leu Tyr Asp Asp Asp Glu Arg Pro Ser Gly Ile Pro Asp Arg Phe Ser
50                  55                  60

Gly Ser Arg Ser Gly Thr Ser Ala Thr Leu Val Ile Thr Gly Leu Gln
65                  70                  75                  80

Thr Gly Asp Glu Ala Asp Tyr Tyr Cys Gly Thr Trp Asp Ser Ser Leu
                85                  90                  95

Ser Val Val Val Phe Gly Gly Gly Thr Arg Leu Thr Val Leu
            100                 105                 110

<210> SEQ ID NO 11
<211> LENGTH: 127
<212> TYPE: PRT
<213> ORGANISM: Artificial sequence
<220> FEATURE:
<223> OTHER INFORMATION: Synthetic amino acid

<400> SEQUENCE: 11

Glu Val Gln Leu Val Gln Ser Gly Ala Glu Val Lys Arg Ala Gly Glu
1               5                   10                  15

Ser Leu Lys Ile Ser Cys Lys Gly Ser Gly Tyr Pro Phe Ala Thr Tyr
            20                  25                  30

Trp Val Gly Trp Val Arg Gln Met Pro Gly Lys Gly Leu Glu Trp Met
        35                  40                  45

Thr Ile Ile Tyr Pro Glu Asp Ser Asp Thr Arg Tyr Ser Pro Ser Phe
50                  55                  60

Gln Asp His Val Thr Ile Ser Ala Asp Lys Ser Leu Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Val Ser Arg Tyr Tyr Tyr Asp Ser Arg Ser Tyr Tyr Pro Asp
            100                 105                 110

Ala Phe Asp Ile Trp Gly Gln Gly Thr Met Val Thr Val Ser Ser
        115                 120                 125

<210> SEQ ID NO 12
<211> LENGTH: 106
<212> TYPE: PRT
<213> ORGANISM: Artificial sequence
<220> FEATURE:
<223> OTHER INFORMATION: Synthetic amino acid

<400> SEQUENCE: 12

Ser Tyr Glu Leu Thr Gln Pro Pro Ser Val Ser Val Ser Pro Gly Gln
1               5                   10                  15

Thr Ala Ser Ile Thr Cys Ser Gly Asp Lys Leu Gly Asp Lys Tyr Val
```

```
                   20                  25                  30

Cys Trp Tyr Gln Gln Lys Pro Gly Arg Ser Pro Val Leu Val Val His
                35                  40                  45

Gln Asp Thr Lys Arg Pro Ser Gly Ile Pro Glu Arg Phe Ser Gly Ser
            50                  55                  60

Asn Ser Gly Asp Thr Ala Thr Leu Thr Ile Ser Gly Thr Gln Ala Met
65                  70                  75                  80

Asp Glu Ala Asp Tyr Tyr Cys Gln Ala Trp Asp Ser Thr Ile Gly Val
                85                  90                  95

Phe Gly Pro Gly Thr Arg Val Thr Val Leu
                100                 105

<210> SEQ ID NO 13
<211> LENGTH: 118
<212> TYPE: PRT
<213> ORGANISM: Artificial sequence
<220> FEATURE:
<223> OTHER INFORMATION: Synthetic amino acid

<400> SEQUENCE: 13

Gln Val Gln Leu Gln Glu Trp Gly Ala Gly Leu Leu Lys Pro Ser Glu
1               5                   10                  15

Thr Leu Ser Leu Thr Cys Ala Val Tyr Gly Gly Ser Phe Ser Asp Tyr
                20                  25                  30

Tyr Trp Asn Trp Ile Arg Gln Pro Pro Gly Lys Gly Leu Glu Trp Ile
            35                  40                  45

Gly Asp Ile Thr His Ser Gly Ala Thr Asn Tyr Asn Pro Ser Leu Thr
        50                  55                  60

Ser Arg Val Thr Phe Ser Val Asp Ile Ser Lys Asn His Phe Ser Leu
65                  70                  75                  80

Lys Leu Thr Ser Val Thr Ala Ala Asp Thr Ala Met Tyr Tyr Cys Ala
                85                  90                  95

Arg Ile Gly Glu Lys Thr Gly Asp Tyr Thr Ile Trp Gly Gln Gly Thr
            100                 105                 110

Met Val Thr Val Ser Ser
        115

<210> SEQ ID NO 14
<211> LENGTH: 107
<212> TYPE: PRT
<213> ORGANISM: Artificial sequence
<220> FEATURE:
<223> OTHER INFORMATION: Synthetic amino acid

<400> SEQUENCE: 14

Ala Ile Gln Met Thr Gln Ser Pro Ser Ser Leu Ser Ala Ser Ile Gly
1               5                   10                  15

Asp Arg Val Thr Ile Thr Cys Arg Ala Ser Gln Gly Ile Arg Asn Asn
                20                  25                  30

Leu Gly Trp Tyr Gln Gln Ala Pro Gly Lys Ala Pro Arg Leu Leu Ile
            35                  40                  45

Tyr Ala Ala Ser Ser Leu Gln Ser Asp Val Pro Ser Arg Phe Ser Gly
        50                  55                  60

Ser Gly Ser Gly Thr Asp Phe Thr Leu Thr Ile Ser Ala Leu Gln Pro
65                  70                  75                  80

Glu Asp Phe Ala Thr Tyr Tyr Cys Leu Gln Asp Tyr Asn Tyr Pro Arg
                85                  90                  95
```

```
Thr Phe Gly Gln Gly Thr Lys Val Glu Ile Lys
            100                 105

<210> SEQ ID NO 15
<211> LENGTH: 100
<212> TYPE: PRT
<213> ORGANISM: Artificial sequence
<220> FEATURE:
<223> OTHER INFORMATION: Synthetic amino acid

<400> SEQUENCE: 15

Glu Val Gln Leu Val Glu Ser Gly Gly Gly Leu Val Gln Pro Gly Gly
1               5                   10                  15

Ser Leu Lys Leu Ser Cys Ala Val Ser Gly Phe Ser Val Ser Asp Ser
            20                  25                  30

Ala Ile His Trp Val Arg Gln Ala Ser Gly Lys Gly Leu Glu Trp Val
        35                  40                  45

Gly His Met Arg Ser Gln Ala Asn Ser Tyr Ala Thr Ala Tyr Gly Ala
    50                  55                  60

Ser Val Arg Gly Arg Phe Asn Ile Ser Arg Asp Asp Ser Lys Asn Thr
65                  70                  75                  80

Ala Tyr Leu Gln Met Asn Ser Leu Asn Ile Asp Asp Thr Ala Val Tyr
                85                  90                  95

Tyr Cys Thr Arg
            100

<210> SEQ ID NO 16
<211> LENGTH: 95
<212> TYPE: PRT
<213> ORGANISM: Artificial sequence
<220> FEATURE:
<223> OTHER INFORMATION: Synthetic amino acid

<400> SEQUENCE: 16

Ser Tyr Val Leu Thr Gln Pro Pro Ser Val Ser Val Ala Pro Gly Gln
1               5                   10                  15

Thr Ala Arg Ile Pro Cys Gly Gly Asn Ser Ile Gly Ser Arg Ser Val
            20                  25                  30

His Trp Tyr Gln Gln Lys Pro Gly Arg Ala Pro Val Leu Val Ile Tyr
        35                  40                  45

Tyr Asp Arg Asp Arg Pro Ser Gly Ile Pro Glu Arg Phe Ser Gly Ser
    50                  55                  60

Asn Ser Gly Asn Thr Ala Thr Leu Thr Ile Asp Arg Val Glu Ala Gly
65                  70                  75                  80

Asp Glu Ala Asp Tyr Tyr Cys Gln Val Trp Asp Gly Ser Ser Asp
                85                  90                  95

<210> SEQ ID NO 17
<211> LENGTH: 8
<212> TYPE: PRT
<213> ORGANISM: Artificial sequence
<220> FEATURE:
<223> OTHER INFORMATION: Synthetic amino acid

<400> SEQUENCE: 17

Gly Phe Pro Phe Ser Asp Tyr His
1               5

<210> SEQ ID NO 18
<211> LENGTH: 8
<212> TYPE: PRT
```

-continued

```
<213> ORGANISM: Artificial sequence
<220> FEATURE:
<223> OTHER INFORMATION: Synthetic amino acid

<400> SEQUENCE: 18

Ile Ser Ser Ala Gly Asn Lys Ile
1               5

<210> SEQ ID NO 19
<211> LENGTH: 21
<212> TYPE: PRT
<213> ORGANISM: Artificial sequence
<220> FEATURE:
<223> OTHER INFORMATION: Synthetic amino acid

<400> SEQUENCE: 19

Ala Arg Asp Ala Gly Tyr Tyr His Gly Ser Gly Asn Asn Ala Ile Tyr
1               5                   10                  15

His Gly Met Asp Val
            20

<210> SEQ ID NO 20
<211> LENGTH: 8
<212> TYPE: PRT
<213> ORGANISM: Artificial sequence
<220> FEATURE:
<223> OTHER INFORMATION: Synthetic amino acid

<400> SEQUENCE: 20

Gly Tyr Pro Phe Ala Thr Tyr Trp
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic amino acid

<400> SEQUENCE: 21

Ile Tyr Pro Glu Asp Ser Asp Thr
1               5

<210> SEQ ID NO 22
<211> LENGTH: 20
<212> TYPE: PRT
<213> ORGANISM: Artificial sequence
<220> FEATURE:
<223> OTHER INFORMATION: Synthetic amino acid

<400> SEQUENCE: 22

Ala Arg Val Ser Arg Tyr Tyr Tyr Asp Ser Arg Ser Tyr Tyr Pro Asp
1               5                   10                  15

Ala Phe Asp Ile
            20

<210> SEQ ID NO 23
<211> LENGTH: 8
<212> TYPE: PRT
<213> ORGANISM: Artificial sequence
<220> FEATURE:
<223> OTHER INFORMATION: Synthetic amino acid

<400> SEQUENCE: 23

Gly Gly Ser Phe Ser Asp Tyr Tyr
1               5
```

```
<210> SEQ ID NO 24
<211> LENGTH: 7
<212> TYPE: PRT
<213> ORGANISM: Artificial sequence
<220> FEATURE:
<223> OTHER INFORMATION: Synthetic amino acid

<400> SEQUENCE: 24

Ile Thr His Ser Gly Ala Thr
1               5

<210> SEQ ID NO 25
<211> LENGTH: 12
<212> TYPE: PRT
<213> ORGANISM: Artificial sequence
<220> FEATURE:
<223> OTHER INFORMATION: Synthetic amino acid

<400> SEQUENCE: 25

Ala Arg Ile Gly Glu Lys Thr Gly Asp Tyr Thr Ile
1               5                   10

<210> SEQ ID NO 26
<211> LENGTH: 8
<212> TYPE: PRT
<213> ORGANISM: Artificial sequence
<220> FEATURE:
<223> OTHER INFORMATION: Synthetic amino acid

<400> SEQUENCE: 26

Gly Phe Ser Val Ser Asp Ser Ala
1               5

<210> SEQ ID NO 27
<211> LENGTH: 10
<212> TYPE: PRT
<213> ORGANISM: Artificial sequence
<220> FEATURE:
<223> OTHER INFORMATION: Synthetic amino acid

<400> SEQUENCE: 27

Met Arg Ser Gln Ala Asn Ser Tyr Ala Thr
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic amino acid

<400> SEQUENCE: 28

Thr Arg Lys Val Asp Asn Arg His Gly Met Asp Val
1               5                   10

<210> SEQ ID NO 29
<211> LENGTH: 8
<212> TYPE: PRT
<213> ORGANISM: Artificial sequence
<220> FEATURE:
<223> OTHER INFORMATION: Synthetic amino acid

<400> SEQUENCE: 29

Ser Ser Asn Ile Gly Tyr Asn Tyr
1               5
```

<210> SEQ ID NO 30
<211> LENGTH: 11
<212> TYPE: PRT
<213> ORGANISM: Artificial sequence
<220> FEATURE:
<223> OTHER INFORMATION: Synthetic amino acid

<400> SEQUENCE: 30

Gly Thr Trp Asp Ser Ser Leu Ser Val Val Val
1               5                   10

<210> SEQ ID NO 31

<400> SEQUENCE: 31

000

<210> SEQ ID NO 32
<211> LENGTH: 6
<212> TYPE: PRT
<213> ORGANISM: Artificial sequence
<220> FEATURE:
<223> OTHER INFORMATION: Synthetic amino acid

<400> SEQUENCE: 32

Lys Leu Gly Asp Lys Tyr
1               5

<210> SEQ ID NO 33
<211> LENGTH: 9
<212> TYPE: PRT
<213> ORGANISM: Artificial sequence
<220> FEATURE:
<223> OTHER INFORMATION: Synthetic amino acid

<400> SEQUENCE: 33

Gln Ala Trp Asp Ser Thr Ile Gly Val
1               5

<210> SEQ ID NO 34

<400> SEQUENCE: 34

000

<210> SEQ ID NO 35
<211> LENGTH: 6
<212> TYPE: PRT
<213> ORGANISM: Artificial sequence
<220> FEATURE:
<223> OTHER INFORMATION: Synthetic amino acid

<400> SEQUENCE: 35

Gln Gly Ile Arg Asn Asn
1               5

<210> SEQ ID NO 36
<211> LENGTH: 9
<212> TYPE: PRT
<213> ORGANISM: Artificial sequence
<220> FEATURE:
<223> OTHER INFORMATION: Synthetic amino acid

<400> SEQUENCE: 36

Leu Gln Asp Tyr Asn Tyr Pro Arg Thr
1               5

<210> SEQ ID NO 37

<400> SEQUENCE: 37

000

<210> SEQ ID NO 38
<211> LENGTH: 6
<212> TYPE: PRT
<213> ORGANISM: Artificial sequence
<220> FEATURE:
<223> OTHER INFORMATION: Synthetic amino acid

<400> SEQUENCE: 38

Ser Ile Gly Ser Arg Ser
1               5

<210> SEQ ID NO 39
<211> LENGTH: 11
<212> TYPE: PRT
<213> ORGANISM: Artificial sequence
<220> FEATURE:
<223> OTHER INFORMATION: Synthetic amino acid

<400> SEQUENCE: 39

Gln Val Trp Asp Gly Ser Ser Asp Gln Tyr Val
1               5                   10

<210> SEQ ID NO 40

<400> SEQUENCE: 40

000

<210> SEQ ID NO 41
<211> LENGTH: 21
<212> TYPE: DNA
<213> ORGANISM: Artificial sequence
<220> FEATURE:
<223> OTHER INFORMATION: Synthetic phosphorothioate-modified
      oligodeoxynucleotide
<220> FEATURE:
<221> NAME/KEY: modified_base
<222> LOCATION: (1)..(21)
<223> OTHER INFORMATION: phosphorothioate base

<400> SEQUENCE: 41
tcgtcgtttt tcggtcgttt t                                       21

<210> SEQ ID NO 42
<211> LENGTH: 376
<212> TYPE: DNA
<213> ORGANISM: Artificial sequence
<220> FEATURE:
<223> OTHER INFORMATION: Synthetic oligonucleotide

<400> SEQUENCE: 42
caggtgcagc tggtggagtc tgggggaggc gtggtccagc ctggggaggtc cctgagactc    60 tcctgcgcag cctctggatt caccttcagc aattatgcca tgcactgggt ccgccaggct   120
ccaggcaagg ggctggagtg gtggcagtt atttcatatg atggaaggag tgaattctat    180
gaagactccg tgaagggccg attctccatc tccagagaca attccaaaag cacgctgtat   240
ctgcaaatga acagcctgag aggtgaggac accgctatgt attactgtgc gaaacccgac   300
tcagctctga accaatatag cagcagctgg acccctgact actggggcca gggaaccctg   360

| | |
|---|---:|
| gtcaccgtct cctcag | 376 |

<210> SEQ ID NO 43
<211> LENGTH: 337
<212> TYPE: DNA
<213> ORGANISM: Artificial sequence
<220> FEATURE:
<223> OTHER INFORMATION: Synthetic oligonucleotide

<400> SEQUENCE: 43

| | |
|---|---:|
| gatgttgtga tgactcagtc tccactctcc ctgcccgtca cccttggaca gccggcctcc | 60 |
| atctcctgca ggtctagtca gaacctcgta cacagtgatg gaaacaccta cttgaattgg | 120 |
| tttcagcaga ggccaggcca atctccaagg cgcctaattt ataagttttc taaccgggac | 180 |
| tctggggtcc cagacagatt cagcggcagt gggtcaggca ctgatttcac actgaaaatc | 240 |
| agcagggtgg aggctgagga tgttggggtt tattactgca tgcaaggtac acactggcct | 300 |
| ccgacgttcg gccaagggac caaggtggaa atcaaac | 337 |

<210> SEQ ID NO 44
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 44

| | |
|---|---:|
| caggtgcagc tggtggagtc tgggggaggc gtggtccagc ctgggaggtc cgtgagactc | 60 |
| tcctgtgaag cctctgggtt catgttcaga agtcatgttc tgcactgggt ccgccagtct | 120 |
| ccaggcaagg ggctggagtg ggtggcagta atttcatatg atggaacaag tcaatatgtc | 180 |
| gcagactccg tgaagggccg ggtcaccgtc tccagagaca attccaggag catgatgttt | 240 |
| ctgcaaatga acagcctcaa aagtgaagat acggctgtgt attactgtgc aagagggagg | 300 |
| aacggctatg aggatttgc tgaccagtgg ggccagggaa ccctggtcac cgtctcctca | 360 |
| g | 361 |

<210> SEQ ID NO 45
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 45

| | |
|---|---:|
| gacatccaga tgacccagtc tccatcctcc ctgtctgcat ctgtgggaga cagagtcacc | 60 |
| atcacttgcc ggccaagtca gaatattcgc aatttttac attggtatca gcagaaaccc | 120 |
| gggaaagccc cgagtctcct gatttattct acatccaatt tagaaagtgg ggtcccctca | 180 |
| aggttcagtg gccgtggatc tgggacagat ttctctctca ccatcgacgg tctgcagccg | 240 |
| gaagatcttg caacttacta ctgtcaacag agttacagtg aatcgtggac attcggccaa | 300 |
| gggaccaggg tggaaatgaa ac | 322 |

<210> SEQ ID NO 46
<211> LENGTH: 349
<212> TYPE: DNA
<213> ORGANISM: Artificial sequence
<220> FEATURE:
<223> OTHER INFORMATION: Synthetic oligonucleotide

<400> SEQUENCE: 46

```
caggtgcagc tgcaggagtc gggcccagga ctggtgaagc cttcggagac cctgtccctc    60
atttgcactg tctctggtgg ctccctcagt aatcactact ggagctggat ccggcaaacc   120
ccagggaaga aactggagtg gattggctat atctattaca gtgggagcac caattacaac   180
ccctccctca agagtcgagt caccatgtca gtagacacgc gcagaaacca ggtctccctg   240
aacctgacct ctgtgaccgc tgcggacacg gccatgtatt tctgtgcgag atataggggg   300
agtggttttg atatctgggg ccaggggaca gtggtcaccg tctcctcag               349

<210> SEQ ID NO 47
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 47
gccatccgga tgacccagtc tccatcctca ttctctgcat ctacaggaga cagagtcacc    60
atcacttgtc gggcgagtca ggatattagc tattttttag cctggtatca gcaaaaacca   120
gggaaagccc ctgagttcct gatgcatgct gcatccactt tgcaaagtgg ggtcccatca   180
aggttcagcg gcagtggctc tgggacagat ttcactctca ccatcagtag tctgcagtct   240
gaagattctg caacttatta ctgtcaacag tattatactt accctcctac gttcggccaa   300
gggaccaagg tggaaatcaa ac                                           322

<210> SEQ ID NO 48
<211> LENGTH: 367
<212> TYPE: DNA
<213> ORGANISM: Artificial sequence
<220> FEATURE:
<223> OTHER INFORMATION: Synthetic oligonucleotide

<400> SEQUENCE: 48
caggtgcagc tgcaggagtc gggcccagga ctggtgaagc cttcggggac cctgtccctc    60
acctgcactg tctctggtgg ctccatcagt catcactact ggagttggat ccggcagccc   120
ccagggaggg gactggagtg gattggttat atctctaaca atgagagcac ccactacagt   180
ccccccctca agagtcgagt caccatatca attgacgcgt ccaagagcca gttctccctg   240
aagctgacct ctgtgaccgt tgctgacacg gccctgtatt tctgtgcgag aggcatccac   300
ctcgactaca tttccgtttt gatgtttgac tcctggggcc agggaaccct cgtcaccgtc   360
tcctcag                                                             367

<210> SEQ ID NO 49
<211> LENGTH: 319
<212> TYPE: DNA
<213> ORGANISM: Artificial sequence
<220> FEATURE:
<223> OTHER INFORMATION: Synthetic oligonucleotide

<400> SEQUENCE: 49
tcctatgagc tgactcagcc accctcagtg tccgtgtccc caggacagac agccagcatc    60
acctgctctg gagatagatt gggggataaa tatacgtcct ggtatcagca gaagtcaggc   120
cagtcccctg tcctggtcat gtatcacgat accaagcggc cctctgggat ccctgagcga   180
ttctctggct ccaactctgg gaacacagcc actctgacca tcagcgggac ccagactgtg   240
gatgaggctg attattactg tcaggcgtgg gacagcagca ctgaagtctt cgggactggg   300
```
accaaggtct ccgtccttg 319

<210> SEQ ID NO 50
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 50
caggtgcagc tgcaggagtc gggcccagga ctggtgaggt cttcagagac cctgtccctc 60
acctgctctg tctctggcgt ccccatccgc agtggagatt actactggaa ttggatgcgc 120
cagtcccccg ggaagggcct ggaatggatt gggtacatct attacagtgg gagtacctcc 180
tacaccccgt cactcaagag tcgactttca atgtcaatag acacgtccaa gaaccaattc 240
tccctggaga tgacttctgt gactgccgca gacacggccg tctattactg tgccagagtg 300
gctttaagcg ggtactttct tgacaattgg ggccagggtg ccctggtcac cgtctcctca 360
g 361

<210> SEQ ID NO 51
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 51
cagtctgtgc tgactcagcc accctcagtg tctgggaccc ccgggcagag ggtcactatc 60
tcttgttctg gaagcagctc caacatcgga agaaattatg tatattggta ctaccagctc 120
ccaggaacgg ccccccaagt cctcatgtat aagaataatc agcggccctc agggtccct 180 gaccgattct ctggctccaa gtctggcact tcagcctccc tggccatcag cgggctccgg 240
tccgaagatg aggctgatta ttactgtgca gcgtgggatg acagcctgag tggtcatgtc 300
ttcggaagtg ggaccaaggt caccgtccta g 331

<210> SEQ ID NO 52
<211> LENGTH: 370
<212> TYPE: DNA
<213> ORGANISM: Artificial sequence
<220> FEATURE:
<223> OTHER INFORMATION: Synthetic oligonucleotide

<400> SEQUENCE: 52
caggtgcagc tggtggagtc tgggggaggc gtggtccagc ctgggaggtc cttgagactc 60
tcttgtggag cgtctggatt caccttcaga caatatggca tgcactgggt ccgccaggct 120
ccaggcaagg ggctggagtg ggtggcagtt atttggttcg acggaagtaa ggaatattat 180
gtcgactccg tgaagggccg tttcaccatc tccagagaca actccaagaa tacgctcttt 240
ttgcaaatga acagcctgag agccgaggac acggctgtgt atttttgtgt gagagatggt 300
cctctcggcg acagcagtgg gacctctttg gacgtctggg gccaagggac cacggtcacc 360
gtctcctcag 370

<210> SEQ ID NO 53
<211> LENGTH: 331
<212> TYPE: DNA
<213> ORGANISM: Artificial sequence
<220> FEATURE:
<223> OTHER INFORMATION: Synthetic oligonucleotide

<400> SEQUENCE: 53

| | |
|---|---|
| tcttctgagc tgactcagga ccctgctgtg tctgtggcct tgggacagac agtcaggatt | 60 |
| acatgccgag agacagcct cagatactat tatgcaagct ggtaccagca gaagccagga | 120 |
| caggcccctc ttcttgtcgt ctatggtaaa acaaccggc cctcaggaat cccagaccgg | 180 |
| ttctctggct ccacctcagg aaacacagct tccttgacca tcactggggc tcaggcggaa | 240 |
| gatgaggctg actattactg tgactcccgg gacagtagtg gtttccatca cgatgttttc | 300 |
| ttcggcggag ggaccagatt gaccgtccta g | 331 |

<210> SEQ ID NO 54
<211> LENGTH: 396
<212> TYPE: DNA
<213> ORGANISM: Artificial sequence
<220> FEATURE:
<223> OTHER INFORMATION: Synthetic oligonucleotide

<400> SEQUENCE: 54

| | |
|---|---|
| caggtgcagc tgcaggagtc gggcccagga ctggtgaagc cttcgcagac cctgtccctc | 60 |
| acctgctctg tctctggtgg cgccattaga agtgatggca acgactgcag gtggacctgg | 120 |
| atccggcagc ccgccgggaa gggactggag tggcttgggc gtgtctcttc cagtgggagc | 180 |
| accagctaca acccctccct caagagtcga ctcaccatgt cgatagactc gtccaagaac | 240 |
| ctcctctccc tgaggctgac ctctgtgacc gccgcagaca cggccgtcta ttactgtgcg | 300 |
| agagaggacg actttaatgc tagtgatttt taccgtagga attacttccc cgctctggac | 360 |
| gtctggggcc gggggactat ggtcaccgtc tcctca | 396 |

<210> SEQ ID NO 55
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 55

| | |
|---|---|
| gacatccaga tgacccagtc tccatcgtcg ctgtctgcat ctgtagggga cagtgtcacc | 60 |
| atcacttgtc gggcaagcca gagaatcggc aattatttaa attggtatca gcacaagcca | 120 |
| gggaaagccc ctaaactcct gatatatgct acatcccgtt tgcaccgtgg ggtcccatcc | 180 |
| aggttcagtg gcggtggatc tgggacagaa ttcactctca ctatcaagac tctcttgcct | 240 |
| gaagattttg caacttattt ctgtcaacag actttcggtg ccctccgtg gacgttcggc | 300 |
| caggggacca aggttgaagc ccgac | 325 |

<210> SEQ ID NO 56
<211> LENGTH: 367
<212> TYPE: DNA
<213> ORGANISM: Artificial sequence
<220> FEATURE:
<223> OTHER INFORMATION: Synthetic oligonucleotide

<400> SEQUENCE: 56

| | |
|---|---|
| caggtgcagc tgcaggagtc gggcccaaga ttggtgaggc cttcagagac cctgtccctc | 60 |
| acctgcactg tctctggtgg ctcgatcagc gataccaatt accattggag ttgggtccgc | 120 |
| cagcccccgg ggaagggcct ggagtggatt ggatacatct attacagcgg gttctctatac | 180 |
| tccaccccgt ccctcaaggg tcgagttacc atatcaatag acatgtccaa gaaccagttc | 240 |

| | |
|---|---|
| tccttgaagc tgacctctgt gtcggccgca gacacggccg tctatttctg tgccagagac | 300 |
| cccatctctt acgctaatgg tgtctttgac ttctggggcc agggagccct ggtcaccgtc | 360 |
| tcctcag | 367 |

<210> SEQ ID NO 57
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 57

| | |
|---|---|
| gacatccaga tgacccagtc tccatcctcc ctgtctgcat ctgtcggaga cagagtcacc | 60 |
| atcacttgcc gggcaagtca gggccttaga aataatttag ctggtatca gcagaagcca | 120 |
| gggcaagccc ctaagcgcct gatctatgct gcttccaagt tacaagatgg ggtcccattg | 180 |
| aggttcagcg gcaatggatc tgggacagaa ttcactctca cgatccacag cctgcagcct | 240 |
| gaggattttg caacttacta ctgtctacag cataatagtt ttcctcgcac gttcggccaa | 300 |
| gggacccagg tggaagtcaa ac | 322 |

<210> SEQ ID NO 58
<211> LENGTH: 361
<212> TYPE: DNA
<213> ORGANISM: Artificial sequence
<220> FEATURE:
<223> OTHER INFORMATION: Synthetic oligonucleotide

<400> SEQUENCE: 58

| | |
|---|---|
| cagctgcagc tgcaggagtc gggcccagga ctggtgaagc cttcggagac cctgtccctc | 60 |
| acctgcactg tctctggtgg ctctttcacc agcaccagtt actactggga ctggatccgc | 120 |
| cagccccag ggaaggggct ggagtggatt gggagtatct attatagtgg gagcacctac | 180 |
| tataaccgt ccctcaagag tcgactcacc atatccgtag acagttccaa gaaccagttc | 240 |
| tccctgaagc tgacctctgt gaccgccgca gacacggctg tctattactg tgcgagacat | 300 |
| gagaagcagt ggacagact tgactcctgg ggccagggaa ccctggtaac cgtctcctca | 360 |
| g | 361 |

<210> SEQ ID NO 59
<211> LENGTH: 322
<212> TYPE: DNA
<213> ORGANISM: Artificial sequence
<220> FEATURE:
<223> OTHER INFORMATION: Synthetic oligonucleotide

<400> SEQUENCE: 59

| | |
|---|---|
| gacatccaga tgacccagtc tccatcctcc ctgtctgcat ctgtaggaga cagagtcacc | 60 |
| atcacttgcc gggcaagtca gagcatctcc acctatttac attggtatca gcagaaacca | 120 |
| ggaaaagccc ctgagctcct gatctatgct gcatccactt tgcaaagtgg ggtcccatca | 180 |
| aggttcagtg gcagtggatc tcggacagat ttcactctca ccatcagcag tctgcaacct | 240 |
| gaagattttg caacttacta ctgtcaacag agttacagta ccgtcctcac tttcggcgga | 300 |
| gggaccaagg tggagatcaa gc | 322 |

<210> SEQ ID NO 60
<211> LENGTH: 384
<212> TYPE: DNA
<213> ORGANISM: Artificial sequence
<220> FEATURE:
<223> OTHER INFORMATION: Synthetic oligonucleotide

<400> SEQUENCE: 60
gaggtgcagc tggtgcagtc tggagcagag gtgaaaaagc cgggggagtc tctgaagatt      60
tcctgtaagg cttctggata cacctttacc aactactgga tcggctgggt gcgccagatg     120
cccgggaaag gcctggagtg gatgggaatc gtctatggtg gtggttctgc gaccacctac     180
aacccgtcct tccaaggccg ggtcaccatc tccgccgaca gtccatcag cacccgcctac     240
ttggagtgga gcagcctgga ggcctcggac accgccatgt attactgtgc gcgacatgta     300
ggtggaggat atagtggctc cggatactac tacttctata gtctggatgt ctggggccaa     360
gggaccacgg tcaccgtctc ctca                                             384

<210> SEQ ID NO 61
<211> LENGTH: 325
<212> TYPE: DNA
<213> ORGANISM: Artificial sequence
<220> FEATURE:
<223> OTHER INFORMATION: Synthetic oligonucleotide

<400> SEQUENCE: 61
gaaattgtgt tgacacagtc tccgggcacc ctgtctttgt ctccagggga cagcgccacc      60
ctctcctgca gggccagtca gggtcttacc agcaactact tagcctggta ccagcagaga     120
cctggccagg ctcccaggct cctcatctat ggtgcatcca aagggccac tggcatccca     180
gacaggttca gtggcagtgg gtctgggaca gacttcactg tcaccatcag tcgactggag     240
cctgaagatt ttgcagtgta ttattgtcag tactatggta cctcacctcc gcctttcggc     300
ggagggacca aggtggagat caaac                                            325

<210> SEQ ID NO 62
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 62

Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Asn Tyr
            20                  25                  30
Ala Met His Trp Val Arg Gln Ala Pro Gly Lys Gly Leu Glu Trp Val
        35                  40                  45
Ala Val Ile Ser Tyr Asp Gly Arg Ser Glu Tyr Glu Asp Ser Val
    50                  55                  60
Lys Gly Arg Phe Ser Ile Ser Arg Asp Asn Ser Lys Ser Thr Leu Tyr
65                  70                  75                  80
Leu Gln Met Asn Ser Leu Arg Gly Glu Asp Thr Ala Met Tyr Tyr Cys
                85                  90                  95
Ala

<210> SEQ ID NO 63
<211> LENGTH: 100
<212> TYPE: PRT
<213> ORGANISM: Artificial sequence
<220> FEATURE:
<223> OTHER INFORMATION: Synthetic polypeptide

```
<400> SEQUENCE: 63

Asp Val Val Met Thr Gln Ser Pro Leu Ser Leu Pro Val Thr Leu Gly
1               5                   10                  15

Gln Pro Ala Ser Ile Ser Cys Arg Ser Ser Gln Asn Leu Val His Ser
            20                  25                  30

Asp Gly Asn Thr Tyr Leu Asn Trp Phe Gln Gln Arg Pro Gly Gln Ser
        35                  40                  45

Pro Arg Arg Leu Ile Tyr Lys Phe Ser Asn Arg Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Thr His Trp Pro
            100

<210> SEQ ID NO 64
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 64

Gln Val Gln Leu Val Glu Ser Gly Gly Gly Val Val Gln Pro Gly Arg
1               5                   10                  15

Ser Val Arg Leu Ser Cys Glu Ala Ser Gly Phe Met Phe Arg Ser His
            20                  25                  30

Val Leu His Trp Val Arg Gln Ser Pro Gly Lys Gly Leu Glu Trp Val
        35                  40                  45

Ala Val Ile Ser Tyr Asp Gly Thr Ser Gln Tyr Val Ala Asp Ser Val
    50                  55                  60

Lys Gly Arg Val Thr Val Ser Arg Asp Asn Ser Arg Ser Met Met Phe
65                  70                  75                  80

Leu Gln Met Asn Ser Leu Lys Ser Glu Asp Thr Ala Val Tyr Tyr Cys
                85                  90                  95

Ala Arg

<210> SEQ ID NO 65
<211> LENGTH: 93
<212> TYPE: PRT
<213> ORGANISM: Artificial sequence
<220> FEATURE:
<223> OTHER INFORMATION: Synthetic polypeptide

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Arg Pro Ser Gln Asn Ile Arg Asn Phe
            20                  25                  30

Leu His Trp Tyr Gln Gln Lys Pro Gly Lys Ala Pro Ser Leu Leu Ile
        35                  40                  45

Tyr Ser Thr Ser Asn Leu Glu Ser Gly Val Pro Ser Arg Phe Ser Gly
    50                  55                  60

Arg Gly Ser Gly Thr Asp Phe Ser Leu Thr Ile Asp Gly Leu Gln Pro
65                  70                  75                  80

Glu Asp Leu Ala Thr Tyr Tyr Cys Gln Gln Ser Tyr Ser
```

-continued

```
                85                  90

<210> SEQ ID NO 66
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 66

Gln Val Gln Leu Gln Glu Ser Gly Pro Gly Leu Val Lys Pro Ser Glu
1               5                   10                  15

Thr Leu Ser Leu Ile Cys Thr Val Ser Gly Gly Ser Leu Ser Asn His
            20                  25                  30

Tyr Trp Ser Trp Ile Arg Gln Thr Pro Gly Lys Lys Leu Glu Trp Ile
        35                  40                  45

Gly Tyr Ile Tyr Tyr Ser Gly Ser Thr Asn Tyr Asn Pro Ser Leu Lys
    50                  55                  60

Ser Arg Val Thr Met Ser Val Asp Thr Ser Gln Asn Gln Val Ser Leu
65                  70                  75                  80

Asn Leu Thr Ser Val Thr Ala Ala Asp Thr Ala Met Tyr Phe Cys Ala
                85                  90                  95

Arg

<210> SEQ ID NO 67
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 67

Ala Ile Arg Met Thr Gln Ser Pro Ser Ser Phe Ser Ala Ser Thr Gly
1               5                   10                  15

Asp Arg Val Thr Ile Thr Cys Arg Ala Ser Gln Asp Ile Ser Tyr Phe
            20                  25                  30

Leu Ala Trp Tyr Gln Gln Lys Pro Gly Lys Ala Pro Glu Phe Leu Met
        35                  40                  45

His Ala Ala Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Ser
65                  70                  75                  80

Glu Asp Ser Ala Thr Tyr Tyr Cys Gln Gln Tyr Tyr Thr Tyr Pro
                85                  90                  95

<210> SEQ ID NO 68
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 68

Gln Val Gln Leu Gln Glu Ser Gly Pro Gly Leu Val Lys Pro Ser Gly
1               5                   10                  15

Thr Leu Ser Leu Thr Cys Thr Val Ser Gly Gly Ser Ile Ser His His
            20                  25                  30

Tyr Trp Ser Trp Ile Arg Gln Pro Pro Gly Arg Gly Leu Glu Trp Ile
        35                  40                  45
```

Gly Tyr Ile Ser Asn Asn Glu Ser Thr His Tyr Ser Pro Pro Leu Lys
            50                  55                  60

Ser Arg Val Thr Ile Ser Ile Asp Ala Ser Lys Ser Gln Phe Ser Leu
 65                  70                  75                  80

Lys Leu Thr Ser Val Thr Val Ala Asp Thr Ala Leu Tyr Phe Cys Ala
                    85                  90                  95

Arg

<210> SEQ ID NO 69
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 69

Ser Tyr Glu Leu Thr Gln Pro Pro Ser Val Ser Val Ser Pro Gly Gln
 1               5                  10                  15

Thr Ala Ser Ile Thr Cys Ser Gly Asp Arg Leu Gly Asp Lys Tyr Thr
                20                  25                  30

Ser Trp Tyr Gln Gln Lys Ser Gly Gln Ser Pro Val Leu Val Met Tyr
            35                  40                  45

His Asp Thr Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Thr Val
 65                  70                  75                  80

Asp Glu Ala Asp Tyr Tyr Cys Gln Ala Trp Asp Ser Ser Thr
                85                  90

<210> SEQ ID NO 70
<211> LENGTH: 99
<212> TYPE: PRT
<213> ORGANISM: Artificial sequence
<220> FEATURE:
<223> OTHER INFORMATION: Synthetic polypeptide

<400> SEQUENCE: 70

Gln Val Gln Leu Gln Glu Ser Gly Pro Gly Leu Val Arg Ser Ser Glu
 1               5                  10                  15

Thr Leu Ser Leu Thr Cys Ser Val Ser Gly Val Pro Ile Arg Ser Gly
                20                  25                  30

Asp Tyr Tyr Trp Asn Trp Met Arg Gln Ser Pro Gly Lys Gly Leu Glu
            35                  40                  45

Trp Ile Gly Tyr Ile Tyr Tyr Ser Gly Ser Thr Ser Tyr Thr Pro Ser
 50                  55                  60

Leu Lys Ser Arg Leu Ser Met Ser Ile Asp Thr Ser Lys Asn Gln Phe
 65                  70                  75                  80

Ser Leu Glu Met Thr Ser Val Thr Ala Ala Asp Thr Ala Val Tyr Tyr
                85                  90                  95

Cys Ala Arg

<210> SEQ ID NO 71
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 71

```
Gln Ser Val Leu Thr Gln Pro Pro Ser Val Ser Gly Thr Pro Gly Gln
1               5                   10                  15

Arg Val Thr Ile Ser Cys Ser Gly Ser Ser Asn Ile Gly Arg Asn
            20                  25                  30

Tyr Val Tyr Trp Tyr Tyr Gln Leu Pro Gly Thr Ala Pro Lys Val Leu
            35                  40                  45

Met Tyr Lys Asn Asn Gln Arg Pro Ser Gly Val Pro Asp Arg Phe Ser
50                  55                  60

Gly Ser Lys Ser Gly Thr Ser Ala Ser Leu Ala Ile Ser Gly Leu Arg
65                  70                  75                  80

Ser Glu Asp Glu Ala Asp Tyr Tyr Cys Ala Ala Trp Asp Asp Ser Leu
                85                  90                  95

Ser Gly
```

<210> SEQ ID NO 72
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 72

```
Gln Val Gln Leu Val Glu Ser Gly Gly Gly Val Val Gln Pro Gly Arg
1               5                   10                  15

Ser Leu Arg Leu Ser Cys Gly Ala Ser Gly Phe Thr Phe Arg Gln Tyr
            20                  25                  30

Gly Met His Trp Val Arg Gln Ala Pro Gly Lys Gly Leu Glu Trp Val
            35                  40                  45

Ala Val Ile Trp Phe Asp Gly Ser Lys Glu Tyr Tyr Val Asp Ser Val
50                  55                  60

Lys Gly Arg Phe Thr Ile Ser Arg Asp Asn Ser Lys Asn Thr Leu Phe
65                  70                  75                  80

Leu Gln Met Asn Ser Leu Arg Ala Glu Asp Thr Ala Val Tyr Phe Cys
                85                  90                  95

Val Arg
```

<210> SEQ ID NO 73
<211> LENGTH: 96
<212> TYPE: PRT
<213> ORGANISM: Artificial sequence
<220> FEATURE:
<223> OTHER INFORMATION: Synthetic polypeptide

<400> SEQUENCE: 73

```
Ser Ser Glu Leu Thr Gln Asp Pro Ala Val Ser Val Ala Leu Gly Gln
1               5                   10                  15

Thr Val Arg Ile Thr Cys Arg Gly Asp Ser Leu Arg Tyr Tyr Tyr Ala
            20                  25                  30

Ser Trp Tyr Gln Gln Lys Pro Gly Gln Ala Pro Leu Leu Val Val Tyr
            35                  40                  45

Gly Lys Asn Asn Arg Pro Ser Gly Ile Pro Asp Arg Phe Ser Gly Ser
50                  55                  60

Thr Ser Gly Asn Thr Ala Ser Leu Thr Ile Thr Gly Ala Gln Ala Glu
65                  70                  75                  80

Asp Glu Ala Asp Tyr Tyr Cys Asp Ser Arg Asp Ser Ser Gly Phe His
                85                  90                  95
```

<210> SEQ ID NO 74
<211> LENGTH: 97
<212> TYPE: PRT
<213> ORGANISM: Artificial sequence
<220> FEATURE:
<223> OTHER INFORMATION: Synthetic polypeptide

<400> SEQUENCE: 74

```
Gln Glu Ser Gly Pro Gly Leu Val Lys Pro Ser Gln Thr Leu Ser Leu
1               5                   10                  15

Thr Cys Ser Val Ser Gly Gly Ala Ile Arg Ser Asp Gly Asn Asp Cys
            20                  25                  30

Arg Trp Thr Trp Ile Arg Gln Pro Ala Gly Lys Gly Leu Glu Trp Leu
        35                  40                  45

Gly Arg Val Ser Ser Gly Ser Thr Ser Tyr Asn Pro Ser Leu Lys
    50                  55                  60

Ser Arg Leu Thr Met Ser Ile Asp Ser Ser Lys Asn Leu Leu Ser Leu
65                  70                  75                  80

Arg Leu Thr Ser Val Thr Ala Ala Asp Thr Ala Val Tyr Tyr Cys Ala
                85                  90                  95

Arg
```

<210> SEQ ID NO 75
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 75

```
Asp Ile Gln Met Thr Gln Ser Pro Ser Ser Leu Ser Ala Ser Val Gly
1               5                   10                  15

Asp Ser Val Thr Ile Thr Cys Arg Ala Ser Gln Arg Ile Gly Asn Tyr
            20                  25                  30

Leu Asn Trp Tyr Gln His Lys Pro Gly Lys Ala Pro Lys Leu Leu Ile
        35                  40                  45

Tyr Ala Thr Ser Arg Leu His Arg Gly Val Pro Ser Arg Phe Ser Gly
    50                  55                  60

Gly Gly Ser Gly Thr Glu Phe Thr Leu Thr Ile Lys Thr Leu Leu Pro
65                  70                  75                  80

Glu Asp Phe Ala Thr Tyr Phe Cys Gln Gln Thr Phe Gly Ala Pro
                85                  90                  95
```

<210> SEQ ID NO 76
<211> LENGTH: 99
<212> TYPE: PRT
<213> ORGANISM: Artificial sequence
<220> FEATURE:
<223> OTHER INFORMATION: Synthetic polypeptide

<400> SEQUENCE: 76

```
Gln Val Gln Leu Gln Glu Ser Gly Pro Arg Leu Val Arg Pro Ser Glu
1               5                   10                  15

Thr Leu Ser Leu Thr Cys Thr Val Ser Gly Gly Ser Ile Ser Asp Thr
            20                  25                  30

Asn Tyr His Trp Ser Trp Val Arg Gln Pro Pro Gly Lys Gly Leu Glu
        35                  40                  45

Trp Ile Gly Tyr Ile Tyr Tyr Ser Gly Phe Ser Tyr Ser Thr Pro Ser
    50                  55                  60
```

```
Leu Lys Gly Arg Val Thr Ile Ser Ile Asp Met Ser Lys Asn Gln Phe
 65                  70                  75                  80

Ser Leu Lys Leu Thr Ser Val Ser Ala Ala Asp Thr Ala Val Tyr Phe
                 85                  90                  95

Cys Ala Arg
```

<210> SEQ ID NO 77
<211> LENGTH: 95
<212> TYPE: PRT
<213> ORGANISM: Artificial sequence
<220> FEATURE:
<223> OTHER INFORMATION: Synthetic polypeptide

<400> SEQUENCE: 77

```
Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Gly Leu Arg Asn Asn
                 20                  25                  30

Leu Gly Trp Tyr Gln Gln Lys Pro Gly Gln Ala Pro Lys Arg Leu Ile
             35                  40                  45

Tyr Ala Ala Ser Lys Leu Gln Asp Gly Val Pro Leu Arg Phe Ser Gly
 50                  55                  60

Asn Gly Ser Gly Thr Glu Phe Thr Leu Thr Ile His Ser Leu Gln Pro
 65                  70                  75                  80

Glu Asp Phe Ala Thr Tyr Tyr Cys Leu Gln His Asn Ser Phe Pro
                 85                  90                  95
```

<210> SEQ ID NO 78
<211> LENGTH: 99
<212> TYPE: PRT
<213> ORGANISM: Artificial sequence
<220> FEATURE:
<223> OTHER INFORMATION: Synthetic polypeptide

<400> SEQUENCE: 78

```
Gln Leu Gln Leu Gln Glu Ser Gly Pro Gly Leu Val Lys Pro Ser Glu
  1               5                  10                  15

Thr Leu Ser Leu Thr Cys Thr Val Ser Gly Gly Ser Phe Thr Ser Thr
                 20                  25                  30

Ser Tyr Tyr Trp Asp Trp Ile Arg Gln Pro Pro Gly Lys Gly Leu Glu
             35                  40                  45

Trp Ile Gly Ser Ile Tyr Tyr Ser Gly Ser Thr Tyr Tyr Asn Pro Ser
 50                  55                  60

Leu Lys Ser Arg Leu Thr Ile Ser Val Asp Ser Ser Lys Asn Gln Phe
 65                  70                  75                  80

Ser Leu Lys Leu Thr Ser Val Thr Ala Ala Asp Thr Ala Val Tyr Tyr
                 85                  90                  95

Cys Ala Arg
```

<210> SEQ ID NO 79
<211> LENGTH: 94
<212> TYPE: PRT
<213> ORGANISM: Artificial sequence
<220> FEATURE:
<223> OTHER INFORMATION: Synthetic polypeptide

<400> SEQUENCE: 79

```
Asp Ile Gln Met Thr Gln Ser Pro Ser Ser Leu Ser Ala Ser Val Gly
  1               5                  10                  15
```

```
Asp Arg Val Thr Ile Thr Cys Arg Ala Ser Gln Ser Ile Ser Thr Tyr
            20                  25                  30

Leu His Trp Tyr Gln Gln Lys Pro Gly Lys Ala Pro Glu Leu Leu Ile
        35                  40                  45

Tyr Ala Ala Ser Thr Leu Gln Ser Gly Val Pro Ser Arg Phe Ser Gly
50                  55                  60

Ser Gly Ser Arg Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr
                85                  90
```

<210> SEQ ID NO 80
<211> LENGTH: 98
<212> TYPE: PRT
<213> ORGANISM: Artificial sequence
<220> FEATURE:
<223> OTHER INFORMATION: Synthetic polypeptide

<400> SEQUENCE: 80

```
Glu Val Gln Leu Val Gln Ser Gly Ala Glu Val Lys Lys Pro Gly Glu
1               5                   10                  15

Ser Leu Lys Ile Ser Cys Lys Ala Ser Gly Tyr Thr Phe Thr Asn Tyr
            20                  25                  30

Trp Ile Gly Trp Val Arg Gln Met Pro Gly Lys Gly Leu Glu Trp Met
        35                  40                  45

Gly Ile Val Tyr Gly Gly Gly Ser Ala Thr Thr Tyr Asn Pro Ser Phe
50                  55                  60

Gln Gly Arg Val Thr Ile Ser Ala Asp Lys Ser Ile Ser Thr Ala Tyr
65                  70                  75                  80

Leu Glu Trp Ser Ser Leu Glu Ala Ser Asp Thr Ala Met Tyr Tyr Cys
                85                  90                  95

Ala Arg
```

<210> SEQ ID NO 81
<211> LENGTH: 96
<212> TYPE: PRT
<213> ORGANISM: Artificial sequence
<220> FEATURE:
<223> OTHER INFORMATION: Synthetic polypeptide

<400> SEQUENCE: 81

```
Glu Ile Val Leu Thr Gln Ser Pro Gly Thr Leu Ser Leu Ser Pro Gly
1               5                   10                  15

Asp Ser Ala Thr Leu Ser Cys Arg Ala Ser Gln Gly Leu Thr Ser Asn
            20                  25                  30

Tyr Leu Ala Trp Tyr Gln Gln Arg Pro Gly Gln Ala Pro Arg Leu Leu
        35                  40                  45

Ile Tyr Gly Ala Ser Arg Arg Ala Thr Gly Ile Pro Asp Arg Phe Ser
50                  55                  60

Gly Ser Gly Ser Gly Thr Asp Phe Thr Val Thr Ile Ser Arg Leu Glu
65                  70                  75                  80

Pro Glu Asp Phe Ala Val Tyr Tyr Cys Gln Tyr Tyr Gly Thr Ser Pro
                85                  90                  95
```

<210> SEQ ID NO 82
<211> LENGTH: 8
<212> TYPE: PRT
<213> ORGANISM: Artificial sequence
<220> FEATURE:

<223> OTHER INFORMATION: Synthetic peptide

<400> SEQUENCE: 82

Gly Phe Thr Phe Ser Asn Tyr Ala
1               5

<210> SEQ ID NO 83
<211> LENGTH: 8
<212> TYPE: PRT
<213> ORGANISM: Artificial sequence
<220> FEATURE:
<223> OTHER INFORMATION: Synthetic peptide

<400> SEQUENCE: 83

Ile Ser Tyr Asp Gly Arg Ser Glu
1               5

<210> SEQ ID NO 84
<211> LENGTH: 18
<212> TYPE: PRT
<213> ORGANISM: Artificial sequence
<220> FEATURE:
<223> OTHER INFORMATION: Synthetic peptide

<400> SEQUENCE: 84

Ala Lys Pro Asp Ser Ala Leu Asn Gln Tyr Ser Ser Ser Trp Thr Pro
1               5                   10                  15

Asp Tyr

<210> SEQ ID NO 85
<211> LENGTH: 8
<212> TYPE: PRT
<213> ORGANISM: Artificial sequence
<220> FEATURE:
<223> OTHER INFORMATION: Synthetic peptide

<400> SEQUENCE: 85

Gly Phe Met Phe Arg Ser His Val
1               5

<210> SEQ ID NO 86
<211> LENGTH: 8
<212> TYPE: PRT
<213> ORGANISM: Artificial sequence
<220> FEATURE:
<223> OTHER INFORMATION: Synthetic peptide

<400> SEQUENCE: 86

Ile Ser Tyr Asp Gly Thr Ser Gln
1               5

<210> SEQ ID NO 87
<211> LENGTH: 13
<212> TYPE: PRT
<213> ORGANISM: Artificial sequence
<220> FEATURE:
<223> OTHER INFORMATION: Synthetic peptide

<400> SEQUENCE: 87

Ala Arg Gly Arg Asn Gly Tyr Gly Gly Phe Ala Asp Gln
1               5                   10

<210> SEQ ID NO 88
<211> LENGTH: 8
<212> TYPE: PRT
<213> ORGANISM: Artificial sequence

```
<220> FEATURE:
<223> OTHER INFORMATION: Synthetic peptide

<400> SEQUENCE: 88

Gly Gly Ser Leu Ser Asn His Tyr
1               5

<210> SEQ ID NO 89
<211> LENGTH: 7
<212> TYPE: PRT
<213> ORGANISM: Artificial sequence
<220> FEATURE:
<223> OTHER INFORMATION: Synthetic peptide

<400> SEQUENCE: 89

Ile Tyr Tyr Ser Gly Ser Thr
1               5

<210> SEQ ID NO 90
<211> LENGTH: 10
<212> TYPE: PRT
<213> ORGANISM: Artificial sequence
<220> FEATURE:
<223> OTHER INFORMATION: Synthetic peptide

<400> SEQUENCE: 90

Ala Arg Asp Arg Gly Ser Gly Phe Asp Ile
1               5                   10

<210> SEQ ID NO 91
<211> LENGTH: 8
<212> TYPE: PRT
<213> ORGANISM: Artificial sequence
<220> FEATURE:
<223> OTHER INFORMATION: Synthetic peptide

<400> SEQUENCE: 91

Gly Gly Ser Ile Ser His His Tyr
1               5

<210> SEQ ID NO 92
<211> LENGTH: 7
<212> TYPE: PRT
<213> ORGANISM: Artificial sequence
<220> FEATURE:
<223> OTHER INFORMATION: Synthetic peptide

<400> SEQUENCE: 92

Ile Ser Asn Asn Glu Ser Thr
1               5

<210> SEQ ID NO 93
<211> LENGTH: 16
<212> TYPE: PRT
<213> ORGANISM: Artificial sequence
<220> FEATURE:
<223> OTHER INFORMATION: Synthetic peptide

<400> SEQUENCE: 93

Ala Arg Gly Ile His Leu Asp Tyr Ile Ser Val Leu Met Phe Asp Ser
1               5                   10                  15

<210> SEQ ID NO 94
<211> LENGTH: 10
<212> TYPE: PRT
<213> ORGANISM: Artificial sequence
<220> FEATURE:
```

<223> OTHER INFORMATION: Synthetic peptide

<400> SEQUENCE: 94

Gly Val Pro Ile Arg Ser Gly Asp Tyr Tyr
1               5                   10

<210> SEQ ID NO 95
<211> LENGTH: 7
<212> TYPE: PRT
<213> ORGANISM: Artificial sequence
<220> FEATURE:
<223> OTHER INFORMATION: Synthetic peptide

<400> SEQUENCE: 95

Ile Tyr Tyr Ser Gly Ser Thr
1               5

<210> SEQ ID NO 96
<211> LENGTH: 12
<212> TYPE: PRT
<213> ORGANISM: Artificial sequence
<220> FEATURE:
<223> OTHER INFORMATION: Synthetic peptide

<400> SEQUENCE: 96

Ala Arg Val Ala Leu Ser Gly Tyr Phe Leu Asp Asn
1               5                   10

<210> SEQ ID NO 97
<211> LENGTH: 8
<212> TYPE: PRT
<213> ORGANISM: Artificial sequence
<220> FEATURE:
<223> OTHER INFORMATION: Synthetic peptide

<400> SEQUENCE: 97

Gly Phe Thr Phe Arg Gln Tyr Gly
1               5

<210> SEQ ID NO 98
<211> LENGTH: 8
<212> TYPE: PRT
<213> ORGANISM: Artificial sequence
<220> FEATURE:
<223> OTHER INFORMATION: Synthetic peptide

<400> SEQUENCE: 98

Ile Trp Phe Asp Gly Ser Lys Glu
1               5

<210> SEQ ID NO 99
<211> LENGTH: 16
<212> TYPE: PRT
<213> ORGANISM: Artificial sequence
<220> FEATURE:
<223> OTHER INFORMATION: Synthetic peptide

<400> SEQUENCE: 99

Val Arg Asp Gly Pro Leu Gly Asp Ser Ser Gly Thr Ser Leu Asp Val
1               5                   10                  15

<210> SEQ ID NO 100
<211> LENGTH: 8
<212> TYPE: PRT
<213> ORGANISM: Artificial sequence
<220> FEATURE:
<223> OTHER INFORMATION: Synthetic peptide

```
<400> SEQUENCE: 100

Arg Ser Asp Gly Asn Asp Cys Arg
1               5

<210> SEQ ID NO 101
<211> LENGTH: 7
<212> TYPE: PRT
<213> ORGANISM: Artificial sequence
<220> FEATURE:
<223> OTHER INFORMATION: Synthetic peptide

<400> SEQUENCE: 101

Val Ser Ser Ser Gly Ser Thr
1               5

<210> SEQ ID NO 102
<211> LENGTH: 22
<212> TYPE: PRT
<213> ORGANISM: Artificial sequence
<220> FEATURE:
<223> OTHER INFORMATION: Synthetic peptide

<400> SEQUENCE: 102

Ala Arg Glu Asp Asp Phe Asn Ala Ser Asp Phe Tyr Arg Arg Asn Tyr
1               5                   10                  15

Phe Pro Ala Leu Asp Val
            20

<210> SEQ ID NO 103
<211> LENGTH: 10
<212> TYPE: PRT
<213> ORGANISM: Artificial sequence
<220> FEATURE:
<223> OTHER INFORMATION: Synthetic peptide

<400> SEQUENCE: 103

Gly Gly Ser Ile Ser Asp Thr Asn Tyr His
1               5                   10

<210> SEQ ID NO 104
<211> LENGTH: 7
<212> TYPE: PRT
<213> ORGANISM: Artificial sequence
<220> FEATURE:
<223> OTHER INFORMATION: Synthetic peptide

<400> SEQUENCE: 104

Ile Tyr Tyr Ser Gly Phe Ser
1               5

<210> SEQ ID NO 105
<211> LENGTH: 14
<212> TYPE: PRT
<213> ORGANISM: Artificial sequence
<220> FEATURE:
<223> OTHER INFORMATION: Synthetic peptide

<400> SEQUENCE: 105

Ala Arg Asp Pro Ile Ser Tyr Ala Asn Gly Val Phe Asp Phe
1               5                   10

<210> SEQ ID NO 106
<211> LENGTH: 10
<212> TYPE: PRT
<213> ORGANISM: Artificial sequence
```

```
<220> FEATURE:
<223> OTHER INFORMATION: Synthetic peptide

<400> SEQUENCE: 106

Gly Gly Ser Phe Thr Ser Thr Ser Tyr Tyr
1               5                   10

<210> SEQ ID NO 107
<211> LENGTH: 7
<212> TYPE: PRT
<213> ORGANISM: Artificial sequence
<220> FEATURE:
<223> OTHER INFORMATION: Synthetic peptide

<400> SEQUENCE: 107

Ile Tyr Tyr Ser Gly Ser Thr
1               5

<210> SEQ ID NO 108
<211> LENGTH: 12
<212> TYPE: PRT
<213> ORGANISM: Artificial sequence
<220> FEATURE:
<223> OTHER INFORMATION: Synthetic peptide

<400> SEQUENCE: 108

Ala Arg His Glu Lys Gln Leu Asp Arg Leu Asp Ser
1               5                   10

<210> SEQ ID NO 109
<211> LENGTH: 8
<212> TYPE: PRT
<213> ORGANISM: Artificial sequence
<220> FEATURE:
<223> OTHER INFORMATION: Synthetic peptide

<400> SEQUENCE: 109

Gly Tyr Thr Phe Thr Asn Tyr Trp
1               5

<210> SEQ ID NO 110
<211> LENGTH: 8
<212> TYPE: PRT
<213> ORGANISM: Artificial sequence
<220> FEATURE:
<223> OTHER INFORMATION: Synthetic peptide

<400> SEQUENCE: 110

Val Tyr Gly Gly Gly Ser Ala Thr
1               5

<210> SEQ ID NO 111
<211> LENGTH: 21
<212> TYPE: PRT
<213> ORGANISM: Artificial sequence
<220> FEATURE:
<223> OTHER INFORMATION: Synthetic peptide

<400> SEQUENCE: 111

Ala Arg His Val Gly Gly Tyr Ser Gly Ser Gly Tyr Tyr Tyr Phe
1               5                   10                  15

Tyr Ser Leu Asp Val
            20

<210> SEQ ID NO 112
<211> LENGTH: 11
```

```
<212> TYPE: PRT
<213> ORGANISM: Artificial sequence
<220> FEATURE:
<223> OTHER INFORMATION: Synthetic peptide

<400> SEQUENCE: 112

Gln Asn Leu Val His Ser Asp Gly Asn Thr Tyr
1               5                   10

<210> SEQ ID NO 113
<211> LENGTH: 9
<212> TYPE: PRT
<213> ORGANISM: Artificial sequence
<220> FEATURE:
<223> OTHER INFORMATION: Synthetic peptide

<400> SEQUENCE: 113

Met Gln Gly Thr His Trp Pro Pro Thr
1               5

<210> SEQ ID NO 114
<211> LENGTH: 6
<212> TYPE: PRT
<213> ORGANISM: Artificial sequence
<220> FEATURE:
<223> OTHER INFORMATION: Synthetic peptide

<400> SEQUENCE: 114

Gln Asn Ile Arg Asn Phe
1               5

<210> SEQ ID NO 115
<211> LENGTH: 9
<212> TYPE: PRT
<213> ORGANISM: Artificial sequence
<220> FEATURE:
<223> OTHER INFORMATION: Synthetic peptide

<400> SEQUENCE: 115

Gln Gln Ser Tyr Ser Glu Ser Trp Thr
1               5

<210> SEQ ID NO 116
<211> LENGTH: 6
<212> TYPE: PRT
<213> ORGANISM: Artificial sequence
<220> FEATURE:
<223> OTHER INFORMATION: Synthetic peptide

<400> SEQUENCE: 116

Gln Asp Ile Ser Tyr Phe
1               5

<210> SEQ ID NO 117
<211> LENGTH: 9
<212> TYPE: PRT
<213> ORGANISM: Artificial sequence
<220> FEATURE:
<223> OTHER INFORMATION: Synthetic peptide

<400> SEQUENCE: 117

Gln Gln Tyr Tyr Thr Tyr Pro Pro Thr
1               5

<210> SEQ ID NO 118
<211> LENGTH: 6
<212> TYPE: PRT
```

```
<213> ORGANISM: Artificial sequence
<220> FEATURE:
<223> OTHER INFORMATION: Synthetic peptide

<400> SEQUENCE: 118

Arg Leu Gly Asp Lys Tyr
1               5

<210> SEQ ID NO 119
<211> LENGTH: 9
<212> TYPE: PRT
<213> ORGANISM: Artificial sequence
<220> FEATURE:
<223> OTHER INFORMATION: Synthetic peptide

<400> SEQUENCE: 119

Gln Ala Trp Asp Ser Ser Thr Glu Val
1               5

<210> SEQ ID NO 120
<211> LENGTH: 8
<212> TYPE: PRT
<213> ORGANISM: Artificial sequence
<220> FEATURE:
<223> OTHER INFORMATION: Synthetic peptide

<400> SEQUENCE: 120

Ser Ser Asn Ile Gly Arg Asn Tyr
1               5

<210> SEQ ID NO 121
<211> LENGTH: 11
<212> TYPE: PRT
<213> ORGANISM: Artificial sequence
<220> FEATURE:
<223> OTHER INFORMATION: Synthetic peptide

<400> SEQUENCE: 121

Ala Ala Trp Asp Asp Ser Leu Ser Gly His Val
1               5                   10

<210> SEQ ID NO 122
<211> LENGTH: 6
<212> TYPE: PRT
<213> ORGANISM: Artificial sequence
<220> FEATURE:
<223> OTHER INFORMATION: Synthetic peptide

<400> SEQUENCE: 122

Ser Leu Arg Tyr Tyr Tyr
1               5

<210> SEQ ID NO 123
<211> LENGTH: 13
<212> TYPE: PRT
<213> ORGANISM: Artificial sequence
<220> FEATURE:
<223> OTHER INFORMATION: Synthetic peptide

<400> SEQUENCE: 123

Asp Ser Arg Asp Ser Ser Gly Phe His His Asp Val Phe
1               5                   10

<210> SEQ ID NO 124
<211> LENGTH: 6
<212> TYPE: PRT
<213> ORGANISM: Artificial sequence
```

<220> FEATURE:
<223> OTHER INFORMATION: Synthetic peptide

<400> SEQUENCE: 124

Gln Arg Ile Gly Asn Tyr
1               5

<210> SEQ ID NO 125
<211> LENGTH: 10
<212> TYPE: PRT
<213> ORGANISM: Artificial sequence
<220> FEATURE:
<223> OTHER INFORMATION: Synthetic peptide

<400> SEQUENCE: 125

Gln Gln Thr Phe Gly Ala Pro Pro Trp Thr
1               5                   10

<210> SEQ ID NO 126
<211> LENGTH: 6
<212> TYPE: PRT
<213> ORGANISM: Artificial sequence
<220> FEATURE:
<223> OTHER INFORMATION: Synthetic peptide

<400> SEQUENCE: 126

Gln Gly Leu Arg Asn Asn
1               5

<210> SEQ ID NO 127
<211> LENGTH: 9
<212> TYPE: PRT
<213> ORGANISM: Artificial sequence
<220> FEATURE:
<223> OTHER INFORMATION: Synthetic peptide

<400> SEQUENCE: 127

Leu Gln His Asn Ser Phe Pro Arg Thr
1               5

<210> SEQ ID NO 128
<211> LENGTH: 6
<212> TYPE: PRT
<213> ORGANISM: Artificial sequence
<220> FEATURE:
<223> OTHER INFORMATION: Synthetic peptide

<400> SEQUENCE: 128

Gln Ser Ile Ser Thr Tyr
1               5

<210> SEQ ID NO 129
<211> LENGTH: 9
<212> TYPE: PRT
<213> ORGANISM: Artificial sequence
<220> FEATURE:
<223> OTHER INFORMATION: Synthetic peptide

<400> SEQUENCE: 129

Gln Gln Ser Tyr Ser Thr Val Leu Thr
1               5

<210> SEQ ID NO 130
<211> LENGTH: 7
<212> TYPE: PRT
<213> ORGANISM: Artificial sequence
<220> FEATURE:

```
<223> OTHER INFORMATION: Synthetic peptide

<400> SEQUENCE: 130

Gln Gly Leu Thr Ser Asn Tyr
1               5

<210> SEQ ID NO 131
<211> LENGTH: 9
<212> TYPE: PRT
<213> ORGANISM: Artificial sequence
<220> FEATURE:
<223> OTHER INFORMATION: Synthetic peptide

<400> SEQUENCE: 131

Gln Tyr Tyr Gly Thr Ser Pro Pro Pro
1               5

<210> SEQ ID NO 132
<211> LENGTH: 23
<212> TYPE: PRT
<213> ORGANISM: Artificial sequence
<220> FEATURE:
<223> OTHER INFORMATION: Synthetic peptide

<400> SEQUENCE: 132

Cys Ala Arg Asp Ala Gly Tyr Tyr His Gly Ser Gly Asn Asn Ala Ile
1               5                   10                  15

Tyr His Gly Met Asp Val Trp
            20

<210> SEQ ID NO 133
<211> LENGTH: 22
<212> TYPE: PRT
<213> ORGANISM: Artificial sequence
<220> FEATURE:
<223> OTHER INFORMATION: Synthetic peptide

<400> SEQUENCE: 133

Cys Ala Arg Val Ser Arg Tyr Tyr Tyr Asp Ser Arg Ser Tyr Tyr Pro
1               5                   10                  15

Asp Ala Phe Asp Ile Trp
            20

<210> SEQ ID NO 134
<211> LENGTH: 14
<212> TYPE: PRT
<213> ORGANISM: Artificial sequence
<220> FEATURE:
<223> OTHER INFORMATION: Synthetic peptide

<400> SEQUENCE: 134

Cys Ala Arg Ile Gly Glu Lys Thr Gly Asp Tyr Thr Ile Trp
1               5                   10
```

HUMAN IGE ANTIBODIES BINDING TO ASPERGILLUS ALLERGENS

PRIORITY CLAIM

This application claims benefit of priority to U.S. Provisional Application Ser. No. 62/746,437, filed Oct. 16, 2018, the entire contents of which are hereby incorporated by reference.

GOVERNMENT SUPPORT CLAUSE

This invention was made with government support under Grant Nos. 1R21AI123307 and 1R01AI130459 awarded by the National Institutes of Health. The government has certain rights in the invention.

BACKGROUND

1. Field of the Disclosure

The present disclosure relates generally to the fields of medicine, infectious disease, and immunology. More particular, the disclosure relates to human IgE antibodies binding to *Aspergillus fumigatus* antigens.

2. Background

At the center of the pathogenesis of type I hypersensitivity reactions lies the IgE molecule (Johansson & Bennich, 1967). In sensitized (IgE antibody positive) individuals, re-exposure to allergen results in IgE engagement by allergen, resulting in FcεRI cross-linking and activation of mast cells and basophils (Oettgen & Burton, 2015). This causes the release of mediators initially into the local tissue with quick spread to the systemic circulation, resulting in the vast array of symptoms associated with allergic disease, including anaphylactic shock. To date, studies of the human IgE molecule, and its targeted epitopes on allergens, have been very limited. Most of the knowledge of this process has come from studies using allergic patient sera (Casaulta et al., 2005). Because serum contains a mixture of many antibodies, with many specificities, directed toward many different epitopes, and having many different affinities, the ability to study and quantify the molecular interaction of IgE with its target allergen by serology is greatly limited. The ideal way to study this process is to use naturally-occurring human IgE mAbs, isolated from allergic patients; however, no such mAbs have previously ever been created.

The clinical evaluation of sensitization to mold occurs by one of two methodologies: direct testing of serum for the presence of fungal specific IgE or evaluation of the skin for a wheal and flare reaction following percutaneous or intradermal administration of a crude mold specific allergen extract. Testing for serum specific IgE is most commonly accomplished using a modified sandwich ELISA where allergen, either derived from allergen extracts, recombinant protein sources, or both is irreversibly bound to high binding capacity solid phase. This is then followed by binding of the patients' endogenous IgE to the allergosorbent and subsequent detection with an enzyme or fluorophore labeled secondary anti-IgE antibody. A positive percutaneous and intradermal test results from cross-linking of specific IgE on mast cell surfaces following introduction of allergen, with subsequent degranulation. Both methods of evaluation require the use of a commercially available fungal allergen extract which is assumed to contain the relevant allergen proteins recognized by the disease causing human IgE antibody response.

Identifying a patient's unique pattern of allergic sensitization to fungi is important both for counseling the patient regarding potential avoidance of allergic triggers, but also in formulating allergen immunotherapy using similar extracts to those used in diagnostic skin testing. There is some evidence that specific allergen immunotherapy to mold is effective in decreasing associated symptoms of mold allergy (Dreborg et al., 1986; Horst et al., 1990). At present, the commercially available mold allergen extracts used in skin testing and immunotherapy have not been standardized for their allergen content. There are marked differences among between mold extract manufacturers in the method of cultivation that they use. Variables include the substrate on which the mold is grown, the relative proportion of extract material derived from hyphae and spore material, and the inclusion of proteins secreted in the growth media, some of which, including Asp f 1, have been shown to be important allergens (Esch & Codina, 2017). Extensive variability among the commercial mold extracts has been demonstrated using protein staining of the crude extract following SDS-PAGE (Esch, 2004). Specific evaluation of Alt a 1 and Asp f 1 content in a number of commercially produced mold allergen extracts using mouse derived mAbs has also shown extensive variability involving several logs of potency between the preparations (Vailes et al., 2001).

ABPM occurs predominantly in the setting of mold colonization in the airway of patients with asthma or cystic fibrosis. The chronic antigenic stimulation leads to an exuberant allergic inflammatory reaction characterized by high total IgE levels which is viewed as evidence of type I hypersensitivity to the colonizing mold. There is often peripheral and airway eosinophilia, progressive airway remodeling with the development of bronchiectasis, and in some cases progression to respiratory failure if left untreated. Therapy for ABPM is primarily anti-inflammatory with the use of systemic corticosteroids. The addition of antifungal agents can be steroid sparing, but they are not consistently useful in inducing remission (Greenberger et al., 2014). Recently, there is evidence that treatment with omalizumab can decrease risk of recurrent exacerbations. This argues for IgE's central role in the pathology of the disease process (Voskamp et al., 2015; Emiralioglu et al., 2016). While a number of molds have been implicated as causes of ABPM, *Aspergillus* spp are by far the most common (Chowdhary et al., 2014). Routine surveillance of sputum samples of cystic fibrosis patients has shown an association between chronic airway colonization with *Aspergillus* and the eventual development of ABPM. During that period of colonization, patients who develop ABPM often display a broadening of the specificity of the IgE antibody response against increasing numbers of *Aspergillus* allergens. This diversification of the patient's IgE response appears to be associated with an increased risk of for the development of ABPM, although it remains unclear if a specific evolution of sensitization reliably predicts the transition to frank ABPM (Casaulta et al., 2005; Nikolaizik et al., 2002).

Because of the robust allergic response present in patients with ABPM, the high circulating IgE levels, and the diversity of mold proteins recognized by their serum IgE, these patients represent an ideal population from which to develop panels of IgE mAbs directed against *Aspergillus*. Such human IgE mAbs would be valuable tools to evaluate the specificity and quantity of relevant allergenic proteins in commercially available *Aspergillus fumigatus* extracts.

SUMMARY

Thus, in accordance with the present disclosure, there is provided a method of detecting an *Aspergillus* allergen comprising (a) contacting a sample suspected of containing said allergen subject with an antibody or antibody fragment having clone-paired heavy and light chain CDR sequences from Tables 3 and 4, respectively; and (b) detecting said allergen in said sample by binding of said antibody or antibody fragment to an allergen in said sample. The sample may be a body fluid, such as blood, sputum, tears, saliva, mucous or serum, semen, cervical or vaginal secretions, amniotic fluid, placental tissues, urine, exudate, transudate, tissue scrapings or feces. The sample may be an environmental sample, such as soil, house dust, water, and food. Detection may comprise ELISA, RIA, lateral flow assay or Western blot. The method may further comprising performing steps (a) and (b) a second time and determining a change in allergen levels as compared to the first assay.

The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

A method of treating an allergic respiratory disease or reducing the likelihood of developing an allergic respiratory disease in an at-risk subject, comprising delivering to said subject an IgG antibody or antibody fragment, wherein said antibody or antibody fragment has clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment.

The antibody may be a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody may be a chimeric antibody or a bispecific antibody. The antibody or antibody fragment may be administered prior to infection or after infection. The subject may suffer from mold allergy, including allergic bronchopulmonary mycosis (ABPM), asthma with fungal sensitization, or atopic dermatitis. Delivering may comprise antibody or antibody fragment administration, or genetic delivery with an RNA or DNA sequence or vector encoding the antibody or antibody fragment.

Also provided is a monoclonal antibody, wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')₂ fragment, or Fv fragment. The antibody may a chimeric antibody, or is bispecific antibody. The antibody may be an IgE, IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may further comprise a cell penetrating peptide and/or is an intrabody.

A further embodiment involves a hybridoma or engineered cell encoding an antibody or antibody fragment wherein the antibody or antibody fragment is characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')2 fragment, or Fv fragment. The antibody may a chimeric antibody or a bispecific antibody. The antibody may be an IgE, IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. The antibody or antibody fragment may further comprise a cell penetrating peptide and/or is an intrabody.

In still a further embodiment, there is provided a vaccine formulation comprising one or more IgG antibodies or antibody fragments characterized by clone-paired heavy and light chain CDR sequences from Tables 3 and 4, respectively. The antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The antibody fragment may be a recombinant scFv (single chain fragment variable) antibody, Fab fragment, F(ab')$_2$ fragment, or Fv fragment. The one or more antibodies may a chimeric antibody, or a bispecific antibody. The antibody or antibodies may be an IgG, or a recombinant IgG antibody or antibody fragment comprising an Fc portion mutated to alter (eliminate or enhance) FcR interactions, to increase half-life and/or increase therapeutic efficacy, such as a LALA, N297, GASD/ALIE, YTE or LS mutation or glycan modified to alter (eliminate or enhance) FcR interactions such as enzymatic or chemical addition or removal of glycans or expression in a cell line engineered with a defined glycosylating pattern. At least one of said antibodies or antibody fragments may further comprise a cell penetrating peptide and/or is an intrabody.

In still yet a further embodiment, there is provide a vaccine formulation comprising one or more expression vectors encoding a first IgG antibody or antibody fragment as defined above. The expression vector(s) may be Sindbis virus or VEE vector(s). The vaccine formulation may be formulated for delivery by needle injection, jet injection, or electroporation. The vaccine formulation may further comprise one or more expression vectors encoding for a second antibody or antibody fragment, such as a distinct antibody or antibody fragment as described herein.

In an additional embodiment, there is provided a method of determining the antigenic integrity, antigenic composition, antigenic conformation and/or correct sequence of an *Aspergillus* antigen or antigen extract comprising (a) contacting a sample comprising said antigen or extract with a first antibody or antibody fragment having clone-paired heavy and light chain CDR sequences from Tables 3 and 4, respectively; and (b) determining the antigenic integrity, antigenic composition, antigenic conformation and/or correct sequence by detectable binding of said first antibody or antibody fragment to said antigen or extract. The sample may comprise recombinantly produced antigen. The sample may comprise a vaccine formulation or vaccine production batch. Detection may comprise ELISA, RIA, western blot, a biosensor using surface plasmon resonance or biolayer interferometry, or flow cytometric staining.

The first antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The first antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The first antibody fragment may be a recombinant scFv (single chain fragment variable) antibody, Fab fragment, F(ab')$_2$ fragment, or Fv fragment. The method may further comprise performing steps (a) and (b) a second time to determine the antigenic stability of the antigen over time.

The method may further comprise (c) contacting a sample comprising said antigen or extract with a second antibody or antibody fragment having clone-paired heavy and light chain CDR sequences from Tables 3 and 4, respectively; and (d) determining the antigenic integrity, antigenic composition, antigenic conformation and/or correct sequence by detectable binding of said second antibody or antibody fragment to said antigen or extract.

The second antibody or antibody fragment may be encoded by clone-paired variable sequences as set forth in Table 1, may be encoded by light and heavy chain variable sequences having 70%, 80%, or 90% identity to clone-paired variable sequences as set forth in Table 1, or may be encoded by light and heavy chain variable sequences having 95% identity to clone-paired sequences as set forth in Table 1. The second antibody or antibody fragment may comprise light and heavy chain variable sequences according to clone-paired sequences from Table 2, may comprise light and heavy chain variable sequences having 70%, 80% or 90% identity to clone-paired sequences from Table 2, or may comprise light and heavy chain variable sequences having 95% identity to clone-paired sequences from Table 2. The second antibody fragment may be a recombinant scFv (single chain fragment variable) antibody, Fab fragment, F(ab')$_2$ fragment, or Fv fragment. The method may further comprise performing steps (c) and (d) a second time to determine the antigenic stability of the sample over time.

A further embodiment is a human IgE monoclonal antibody or antibody fragment, or hybridoma or engineered cell producing the same, wherein said antibody binds to Asp f 1 and Asp f9.

Another embodiment involves a method of de-sensitizing a subject to an *Aspergillus* allergen comprising (a) administering to said subject an *Aspergillus* allergen; and (b) administering to said subject an IgG antibody that has a binding specificity to said allergen obtained from an IgE antibody or antibody fragment having clone-paired heavy and light chain CDR sequences from Tables 3 and 4, respectively. The allergen and said IgG antibody may be mixed together prior to administering, or the allergen and said IgG antibody may be administered to said subject separately. The allergen and said IgG antibody may administered to said subject multiple times. The subject may be a human or a non-human mammal. The allergen may be administered with an adjuvant.

Also provided is a method of producing an IgG immune response to an *Aspergillus* allergen comprising (a) identifying an IgE epitope in an allergen by mapping the binding of an IgE antibody binding site, wherein said antibody has clone-paired heavy and light chain CDR sequences from Tables 3 and 4, respectively; (b) modifying one or more residues in said IgE antibody binding site to reduce or eliminate IgE antibody binding to said binding site, thereby producing a hypoallergenic *Aspergillus* allergen; (c) immunizing a subject with said hypoallergenic *Aspergillus* allergen to produce and IgG resopnse to said hypoallegenic *Aspergillus* allergen, while producing a reduced or no IgE response as compared to the allergen of step (a). The IgE antibody binding to said binding site may be reduced by at least 90%, or may be eliminated. The hypoallergenic *Aspergillus* allergen may be administered to said subject with an adjuvant and/or is administered multiple times.

A still yet further embodiment involves a method of identifying an IgE *Aspergillus* allergen comprising (a) obtaining an IgE-producing B cell having clone-paired heavy and light chain CDR sequences from Tables 3 and 4, respectively; (b) immortalizing said IgE-producing B cell; (c) obtaining monoclonal IgE from the immortalized B cell of step (b); (d) identifying an allergen that binds to said monoclonal IgE. The method may further comprise producing a vaccine that lacks the IgE epitope on said *Aspergilllus* allergen.

The use of the word "a" or "an" when used in conjunction with the term "comprising" in the claims and/or the specification may mean "one," but it is also consistent with the meaning of "one or more," "at least one," and "one or more than one." The word "about" means plus or minus 5% of the stated number.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The following drawings form part of the present specification and are included to further demonstrate certain aspects of the present disclosure. The disclosure may be better understood by reference to one or more of these drawings in combination with the detailed description of specific embodiments presented herein.

FIGS. 1A-B. Identification of Asp f 1 in commercial extracts using human IgE mAbs. Indirect fluorescence ELISA (FIG. 1A) and Western blot (FIG. 1B) analysis were performed on commercially manufactured allergenic extracts from GREER, HS, ALKB, and AlrgyL using human IgE mAbs to the major allergen Asp f 1.

FIG. 2. Asp f 1-induced anaphylaxis in human transgenic mice. Human FcεRIα transgenic mice were sensitized with human Asp f 1-specific IgE mAbs 17A5 and 14H4 or saline. Animals were challenged with 5 μg of recombinant Asp f 1 or the maximum tolerated dose of extract manufactured by GREER, HS, ALKB, or AlrgyL. Three mice were used in each group. Error bars represent standard error of the mean with temperature differences between control and allergen challenged animals assessed by paired t-test with a calculated p-value of less than 0.05 deemed as significant and highlighted by an asterisk.

DESCRIPTION OF ILLUSTRATIVE EMBODIMENTS

As discussed above, sensitization to *Aspergillus* spp. is associated with allergic respiratory diseases. Allergen immunotherapy with non-standardized *Aspergillus* extracts is commonly used as therapy in these patients. Unfortunately, no method exists to measure the relevant allergen protein content in diagnostic and therapeutic. Thus, there is critical need for *Aspergillus* extract standardization.

The inventors hypothesized that development of *Aspergillus*-specific human monoclonal IgE antibodies would allow for the characterization of the relevant human allergenic epitopes among currently available commercial *Aspergillus fumigatus* extracts. Patients with allergic bronchopulmonary mycosis (ABPM; ABPA in the case of *Aspergillus*) were recruited from within the Vanderbilt University Medical Center. Peripheral blood mononuclear cells (PBMCs) were isolated, and IgE antibody secreting B-cells were grown and immortalized using human hybridoma techniques developed by the inventors. This technology was used to generate a large unbiased panel of *Aspergillus*-specific human IgE mAbs from subjects with ABPM. Antibody was purified from hybridoma supernatants and used for western blot and ELISA assays of commercial allergen extract of *Aspergillus fumigatus*. Functional allergen content was assessed using murine anaphylaxis.

Twenty-six human *Aspergillus*-reactive IgE mAbs were used as capture and detection reagents to characterize the *Aspergillus* allergen content of commercial extracts. The inventors found extreme variability in the specificity and quantity of their protein targets. Just four mAbs reacted with all available commercial extracts and only one of four extracts contained the major allergen Asp f 1. This degree of variability will almost certainly to affect the efficacy of these reagents when used in diagnosis and treatment. Human monoclonal IgE antibodies represent an innovative tool for the evaluation of relevant human allergenic epitopes, which may assist in the development and long-term standardization of mold extracts in the future.

These and other aspects of the disclosure are described in detail below.

I. *ASPERGILLUS*

*Aspergillus* is a genus consisting of a few hundred mold species found in various climates worldwide. *Aspergillus* was first catalogued in 1729 by the Italian priest and biologist Pier Antonio Micheli. Viewing the fungi under a microscope, Micheli was reminded of the shape of an aspergillum (holy water sprinkler), from Latin spargere (to sprinkle), and named the genus accordingly. Aspergillum is an asexual spore-forming structure common to all *Aspergillus* species; around one-third of species are also known to have a sexual stage.

*Aspergillus* is defined as a group of conidial fungi—that is, fungi in an asexual state. Some of them, however, are known to have a teleomorph (sexual state) in the Ascomycota, so with DNA evidence forthcoming, members of the genus *Aspergillus* can tentatively be considered members of the Ascomycota. Members of the genus possess the ability to grow where a high osmotic pressure exists (high concentration of sugar, salt, etc.). *Aspergillus* species are highly aerobic and are found in almost all oxygen-rich environments, where they commonly grow as molds on the surface of a substrate, as a result of the high oxygen tension. Commonly, fungi grow on carbon-rich substrates like monosaccharides (such as glucose) and polysaccharides (such as amylose). *Aspergillus* species are common contaminants of starchy foods (such as bread and potatoes), and grow in or on many plants and trees.

In addition to growth on carbon sources, many species of *Aspergillus* demonstrate oligotrophy where they are capable of growing in nutrient-depleted environments, or environments with a complete lack of key nutrients. *A. niger* is a prime example of this; it can be found growing on damp walls, as a major component of mildew. *Aspergillus* are found in millions in pillows.

Species of *Aspergillus* are important medically and commercially. Some species can cause infection in humans and other animals. Some infections found in animals have been studied for years, while other species found in animals have been described as new and specific to the investigated disease, and others have been known as names already in use for organisms such as saprophytes. More than 60 *Aspergillus* species are medically relevant pathogens. For humans, a range of diseases such as infection to the external ear, skin lesions, and ulcers classed as mycetomas are found.

Other species are important in commercial microbial fermentations. For example, alcoholic beverages such as Japanese sake are often made from rice or other starchy ingredients (like manioc), rather than from grapes or malted barley. Typical microorganisms used to make alcohol, such as yeasts of the genus *Saccharomyces*, cannot ferment these starches. Therefore, koji mold such as *Aspergillus oryzae* is used to first break down the starches into simpler sugars. Members of the genus are also sources of natural products that can be used in the development of medications to treat human disease.

Perhaps the largest application of *Aspergillus niger* is as the major source of citric acid; this organism accounts for over 99% of global citric acid production, or more than 1.4 million tons per year. *A. niger* is also commonly used for the production of native and foreign enzymes, including glucose oxidase, lysozyme, and lactase. In these instances, the culture is rarely grown on a solid substrate, although this is still common practice in Japan, but is more often grown as a submerged culture in a bioreactor. In this way, the most important parameters can be strictly controlled, and maximal productivity can be achieved. This process also makes it far easier to separate the chemical or enzyme of importance from the medium and is therefore far more cost-effective.

*A. nidulans* (*Emericella nidulans*) has been used as a research organism for many years and was used by Guido Pontecorvo to demonstrate parasexuality in fungi. Recently, *A. nidulans* was one of the pioneering organisms to have its genome sequenced by researchers at the Broad Institute. As of 2008, a further seven *Aspergillus* species have had their genomes sequenced: the industrially useful *A. niger* (two strains), *A. oryzae*, and *A. terreus*, and the pathogens *A. clavatus*, *A. fischerianus* (*Neosartorya fischeri*), *A. flavus*, and *A. fumigatus* (two strains). *A. fischerianus* is hardly ever pathogenic but is very closely related to the common pathogen *A. fumigatus*; it was sequenced in part to better understand *A. fumigatus* pathogenicity.

The simultaneous publication of three *Aspergillus* genome manuscripts in Nature in December 2005 established the genus as the leading filamentous fungal genus for comparative genomic studies. Like most major genome projects, these efforts were collaborations between a large sequencing centre and the respective community of scientists. For example, the Institute for Genome Research (TIGR) worked with the *A. fumigatus* community. *A. nidulans* was sequenced at the Broad Institute. *A. oryzae* was sequenced in Japan at the National Institute of Advanced Industrial Science and Technology. The Joint Genome Institute of the Department of Energy has released sequence data for a citric acid-producing strain of *A. niger*.

Genome sizes for sequenced species of *Aspergillus* range from about 29.3 Mb for *A. fumigatus* to 37.1 Mb for *A. oryzae*, while the numbers of predicted genes vary from about 9926 for *A. fumigatus* to about 12,071 for *A. oryzae*. The genome size of an enzyme-producing strain of *A. niger* is of intermediate size at 33.9 Mb.

Some *Aspergillus* species cause serious disease in humans and animals. The most common pathogenic species are *A. fumigatus* and *A. flavus*, which produces aflatoxin which is both a toxin and a carcinogen, and which can contaminate foods such as nuts. The most common species causing allergic disease are *A. fumigatus* and *A. clavatus*. Other species are important as agricultural pathogens. *Aspergillus* spp. cause disease on many grain crops, especially maize, and some variants synthesize mycotoxins, including aflatoxin. *Aspergillus* can cause neonatal infections.

*A. fumigatus* (the most common species) infections are primary pulmonary infections and can potentially become a rapidly necrotizing pneumonia with a potential to disseminate. The organism can be differentiated from other common mold infections based on the fact that it takes on a mold form both in the environment and in the host (unlike *Candida albicans* which is a dimorphic mold in the environment and a yeast in the body).

Aspergillosis is the group of diseases caused by *Aspergillus*. The most common subtype among paranasal sinus infections associated with aspergillosis is *A. fumigatus*. The symptoms include fever, cough, chest pain, or breathlessness, which also occur in many other illnesses, so diagnosis can be difficult. Usually, only patients with already weakened immune systems or who suffer other lung conditions are susceptible. In humans, the major forms of disease are:
  Allergic bronchopulmonary aspergillosis, which affects patients with respiratory diseases such as asthma, cystic fibrosis, and sinusitis
  Acute invasive aspergillosis, a form that grows into surrounding tissue, more common in those with weakened immune systems such as AIDS or chemotherapy patients
  Disseminated invasive aspergillosis, an infection spread widely through the body
  Aspergilloma, a "fungus ball" that can form within cavities such as the lung Aspergillosis of the air passages is also frequently reported in birds, and certain species of *Aspergillus* have been known to infect insects.

*Aspergillus fumigatus* is a species of fungus in the genus *Aspergillus* and is one of the most common *Aspergillus* species to cause disease in individuals with an immunodeficiency. *A. fumigatus*, a saprotroph widespread in nature, is typically found in soil and decaying organic matter, such as compost heaps, where it plays an essential role in carbon and nitrogen recycling. Colonies of the fungus produce from conidiophores thousands of minute grey-green conidia (2-3 µm) that readily become airborne. For many years, *A. fumigatus* was thought to only reproduce asexually, as neither mating nor meiosis had ever been observed. In 2008, however, *A. fumigatus* was shown to possess a fully functional sexual reproductive cycle, 145 years after its original description by Fresenius. Although *A. fumigatus* occurs in areas with widely different climates and environments, it displays low genetic variation and a lack of population genetic differentiation on a global scale. Thus, the capability for sex is maintained, though little genetic variation is produced.

The fungus is capable of growth at 37° C. or 99° F. (normal human body temperature), and can grow at temperatures up to 50° C. or 122° F., with conidia surviving at 70° C. or 158° F.—conditions it regularly encounters in self-heating compost heaps. Its spores are ubiquitous in the atmosphere, and everybody inhales an estimated several hundred spores each day; typically, these are quickly eliminated by the immune system in healthy individuals. In immunocompromised individuals, such as organ transplant recipients and people with AIDS or leukemia, the fungus is more likely to become pathogenic, over-running the host's weakened defenses and causing a range of diseases generally termed aspergillosis. Several virulence factors have been postulated to explain this opportunistic behaviour.

When the fermentation broth of *A. fumigatus* was screened, a number of indolic alkaloids with antimitotic properties were discovered. The compounds of interest have been of a class known as tryprostatins, with spirotryprostatin B being of special interest as an anticancer drug. *Aspergillus fumigatus* grown on certain building materials can produce genotoxic and cytotoxic mycotoxins, such as gliotoxin.

*Aspergillus fumigatus* has a stable haploid genome of 29.4 million base pairs. The genome sequences of three *Aspergillus* species—*Aspergillus fumigatus, Aspergillus nidulans*, and *Aspergillus oryzae*—were published in Nature in December 2005.

*Aspergillus fumigatus* is the most frequent cause of invasive fungal infection in immunosuppressed individuals, which include patients receiving immunosuppressive therapy for autoimmune or neoplastic disease, organ transplant recipients, and AIDS patients. *A. fumigatus* primarily causes invasive infection in the lung and represents a major cause of morbidity and mortality in these individuals. Additionally, *A. fumigatus* can cause chronic pulmonary infections, allergic bronchopulmonary aspergillosis, or allergic disease in immunocompetent hosts.

Inhalational exposure to airborne conidia is continuous due to their ubiquitous distribution in the environment. However, in healthy individuals, the innate immune system is an efficacious barrier to *A. fumigatus* infection. A large portion of inhaled conidia are cleared by the mucociliary action of the respiratory epithelium. Due to the small size of conidia, many of them deposit in alveoli, where they interact with epithelial and innate effector cells. Alveolar macrophages phagocytize and destroy conidia within their phagosomes. Epithelial cells, specifically type II pneumocytes, also internalize conidia which traffic to the lysosome where ingested conidia are destroyed. First line immune cells also serve to recruit neutrophils and other inflammatory cells through release of cytokines and chemokines induced by ligation of specific fungal motifs to pathogen recognition receptors. Neutrophils are essential for aspergillosis resistance, as demonstrated in neutropenic individuals, and are capable of sequestering both conidia and hyphae through distinct, non-phagocytic mechanisms. Hyphae are too large for cell-mediated internalization, and thus neutrophil-mediated NADPH-oxidase induced damage represents the dominant host defense against hyphae. In addition to these cell-mediated mechanisms of elimination, antimicrobial peptides secreted by the airway epithelium contribute to host defense.

Immunosuppressed individuals are susceptible to invasive *A. fumigatus* infection, which most commonly manifests as invasive pulmonary aspergillosis. Inhaled conidia that evade host immune destruction are the progenitors of invasive disease. These conidia emerge from dormancy and make a morphological switch to hyphae by germinating in the warm, moist, nutrient-rich environment of the pulmonary alveoli. Germination occurs both extracellularly or in type II pneumocyte endosomes containing conidia. Following germination, filamentous hyphal growth results in epithelial penetration and subsequent penetration of the vascular endothelium. The process of angioinvasion causes endothelial damage and induces a proinflammatory response, tissue factor expression and activation of the coagulation cascade. This results in intravascular thrombosis and localized tissue infarction, however, dissemination of hyphal fragments is usually limited. Dissemination through the blood stream only occurs in severely immunocompromised individuals.

II. MONOCLONAL ANTIBODIES AND PRODUCTION THEREOF

An "isolated antibody" is one that has been separated and/or recovered from a component of its natural environment. Contaminant components of its natural environment are materials that would interfere with diagnostic or therapeutic uses for the antibody, and may include enzymes, hormones, and other proteinaceous or non-proteinaceous solutes. In particular embodiments, the antibody is purified: (1) to greater than 95% by weight of antibody as determined by the Lowry method, and most particularly more than 99% by weight; (2) to a degree sufficient to obtain at least 15 residues of N-terminal or internal amino acid sequence by use of a spinning cup sequenator; or (3) to homogeneity by SDS-PAGE under reducing or non-reducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

The basic four-chain antibody unit is a heterotetrameric glycoprotein composed of two identical light (L) chains and two identical heavy (H) chains. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable region ($V_H$) followed by three constant domains ($C_H$) for each of the alpha and gamma chains and four $C_H$ domains for mu and isotypes. Each L chain has at the N-terminus, a variable region ($V_L$) followed by a constant domain (CL) at its other end. The $V_L$ is aligned with the $V_H$ and the CL is aligned with the first constant domain of the heavy chain ($C_{H1}$). Particular amino acid residues are believed to form an interface between the light chain and heavy chain variable regions. The pairing of a $V_H$ and $V_L$ together forms a single antigen-binding site. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The term "variable" refers to the fact that certain segments of the V domains differ extensively in sequence among antibodies. The V domain mediates antigen binding and defines specificity of a particular antibody for its particular antigen. However, the variability is not evenly distributed across the 110-amino acid span of the variable regions. Instead, the V regions consist of relatively invariant stretches called framework regions (FRs) of 15-30 amino acids separated by shorter regions of extreme variability called "hypervariable regions" that are each 9-12 amino acids long. The variable regions of native heavy and light chains each comprise four FRs, largely adopting a beta-sheet configuration, connected by three hypervariable regions, which form loops connecting, and in some cases forming part of, the beta-sheet structure. The hypervariable regions in each chain are held together in close proximity by the FRs and, with the hypervariable regions from the other chain, contribute to the formation of the antigen-binding site of antibodies (see Kabat et al., Sequences of Proteins of Immunological Interest, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC), antibody-dependent cellular phagocytosis (ADCP), antibody-dependent neutrophil phagocytosis (ADNP), and antibody-dependent complement deposition (ADCD).

The term "hypervariable region" when used herein refers to the amino acid residues of an antibody that are responsible for antigen binding. The hypervariable region generally comprises amino acid residues from a "complementarity determining region" or "CDR" (e.g., around about residues 24-34 (L1), 50-56 (L2) and 89-97 (L3) in the $V_L$, and around about 31-35 (H1), 50-65 (H2) and 95-102 (H3) in the $V_H$ when numbered in accordance with the Kabat numbering system; Kabat et al., Sequences of Proteins of Immunological Interest, 5th Ed. Public Health Service, National Institutes of Health, Bethesda, Md. (1991)); and/or those residues from a "hypervariable loop" (e.g., residues 24-34 (L1), 50-56 (L2) and 89-97 (L3) in the $V_L$, and 26-32 (H1), 52-56 (H2) and 95-101 (H3) in the $V_H$ when numbered in accordance with the Chothia numbering system; Chothia and Lesk, J. Mol. Biol. 196:901-917 (1987)); and/or those residues from a "hypervariable loop"/CDR (e.g., residues 27-38 (L1), 56-65 (L2) and 105-120 (L3) in the $V_L$, and 27-38 (H1), 56-65 (H2) and 105-120 (H3) in the $V_H$ when numbered in accordance with the IMGT numbering system; Lefranc, M. P. et al. Nucl. Acids Res. 27:209-212 (1999), Ruiz, M. et al. Nucl. Acids Res. 28:219-221 (2000)). Optionally the antibody has symmetrical insertions at one or more of the following points 28, 36 (L1), 63, 74-75 (L2) and 123 (L3) in the $V_L$, and 28, 36 (H1), 63, 74-75 (H2) and 123 (H3) in the $V_{sub}H$ when numbered in accordance with AHo; Honneger, A. and Plunkthun, A. J. Mol. Biol. 309:657-670 (2001)).

By "germline nucleic acid residue" is meant the nucleic acid residue that naturally occurs in a germline gene encoding a constant or variable region. "Germline gene" is the DNA found in a germ cell (i.e., a cell destined to become an egg or in the sperm). A "germline mutation" refers to a heritable change in a particular DNA that has occurred in a germ cell or the zygote at the single-cell stage, and when transmitted to offspring, such a mutation is incorporated in every cell of the body. A germline mutation is in contrast to a somatic mutation which is acquired in a single body cell. In some cases, nucleotides in a germline DNA sequence encoding for a variable region are mutated (i.e., a somatic mutation) and replaced with a different nucleotide.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, the monoclonal antibodies useful in the present disclosure may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567) after single cell sorting of an antigen specific B cell, an antigen specific plasmablast responding to an infection or immunization, or capture of linked heavy and light chains from single cells in a bulk sorted antigen specific collection. The "monoclonal antibodies" may also be isolated from phage antibody libraries using the techniques described in Clackson et al., Nature, 352:624-628 (1991) and Marks et al., J. Mol. Biol., 222: 581-597 (1991), for example.

A. General Methods

It will be understood that IgE monoclonal antibodies will have several applications. These include the production of kits for use in measuring *Aspergillus* antigens or detecting and diagnosing *Aspergillus* infection or contaminations. In these contexts, one may link such antibodies to diagnostic agents, use them as capture agents or competitors in competitive assays, or use them individually without additional agents being attached thereto. Also, the antibodies may be used to assess the characteristics and content of antigen preparations, such as vaccines. The antibodies may be mutated or modified, as discussed further below. Methods for preparing and characterizing antibodies are well known in the art (see, e.g., Antibodies: A Laboratory Manual, Cold Spring Harbor Laboratory, 1988; U.S. Pat. No. 4,196,265).

The methods for generating monoclonal antibodies (MAbs) generally begin along the same lines as those for preparing polyclonal antibodies. The first step for both these methods is immunization of an appropriate host or identification of subjects who are immune due to prior natural infection or vaccination with a licensed or experimental vaccine. As is well known in the art, a given composition for immunization may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimyde and bis-biazotized benzidine. As also is well known in the art, the immunogenicity of a particular immunogen composition can be enhanced by the use of non-specific stimulators of the immune response, known as adjuvants. Exemplary and preferred adjuvants in animals include complete Freund's adjuvant (a non-specific stimulator of the immune response containing killed *Mycobacterium tuberculosis*), incomplete Freund's adjuvants and aluminum hydroxide adjuvant and in humans include alum, CpG, MFP59 and combinations of immunostimulatory molecules ("Adjuvant Systems", such as AS01 or AS03). Additional experimental forms of inoculation to induce *A. fumigatus*-specific B cells is possible, including nanoparticle vaccines, or gene-encoded antigens delivered as DNA or RNA genes in a physical delivery system (such as lipid nanoparticle or on a gold biolistic bead), and delivered with needle, gene gun, transcutaneous electroporation device. The antigen gene also can be carried as encoded by a replication competent or defective viral vector such as adenovirus, adeno-associated virus, poxvirus, herpesvirus, or alphavirus replicon, or alternatively a virus like particle.

In the case of human antibodies against natural pathogens, a suitable approach is to identify subjects that have been exposed to the pathogens, such as those who have been diagnosed as having contracted the disease, or those who have been vaccinated to generate protective immunity against the pathogen or to test the safety or efficacy of an experimental vaccine. Circulating anti-pathogen antibodies can be detected, and antibody encoding or producing B cells from the antibody-positive subject may then be obtained.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster injection, also may be given. The process of boosting and titering is repeated until a suitable titer is achieved. When a desired level of immunogenicity is obtained, the immunized animal can be bled and the serum isolated and stored, and/or the animal can be used to generate MAbs.

Following immunization, somatic cells with the potential for producing antibodies, specifically B lymphocytes (B cells), are selected for use in the MAb generating protocol. These cells may be obtained from biopsied spleens, lymph nodes, tonsils or adenoids, bone marrow aspirates or biopsies, tissue biopsies from mucosal organs like lung or GI tract, or from circulating blood. The antibody-producing B lymphocytes from the immunized animal or immune human are then fused with cells of an immortal myeloma cell, generally one of the same species as the animal that was immunized or human or human/mouse chimeric cells. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas). Any one of a number of myeloma cells may be used, as are known to those of skill in the art (Goding, pp. 65-66, 1986; Campbell, pp. 75-83, 1984). HMMA2.5 cells or MFP-2 cells are particularly useful examples of such cells.

Methods for generating hybrids of antibody-producing spleen or lymph node cells and myeloma cells usually comprise mixing somatic cells with myeloma cells in a 2:1 proportion, though the proportion may vary from about 20:1 to about 1:1, respectively, in the presence of an agent or agents (chemical or electrical) that promote the fusion of cell membranes. In some cases, transformation of human B cells with Epstein Barr virus (EBV) as an initial step increases the size of the B cells, enhancing fusion with the relatively large-sized myeloma cells. Transformation efficiency by EBV is enhanced by using CpG and a Chk2 inhibitor drug in the transforming medium. Alternatively, human B cells can be activated by co-culture with transfected cell lines expressing CD40 Ligand (CD154) in medium containing additional soluble factors, such as IL-21 and human B cell Activating Factor (BAFF), a Type II member of the TNF superfamily. Fusion methods using Sendai virus have been described by Kohler and Milstein (1975; 1976), and those using polyethylene glycol (PEG), such as 37% (v/v) PEG, by Gefter et al. (1977). The use of electrically induced fusion methods also is appropriate (Goding, pp. 71-74, 1986) and there are processes for better efficiency (Yu et al., 2008). Fusion procedures usually produce viable hybrids at low frequencies, about $1\times10^{-6}$ to $1\times10^{-8}$, but with optimized procedures one can achieve fusion efficiencies close to 1 in 200 (Yu et al., 2008). However, relatively low efficiency of fusion does not pose a problem, as the viable, fused hybrids are differentiated from the parental, infused cells (particularly the infused myeloma cells that would normally continue to divide indefinitely) by culturing in a selective medium. The selective medium is generally one that contains an agent that blocks the de novo synthesis of nucleotides in the tissue culture medium. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the medium is supplemented with hypoxanthine and thymidine as a source of nucleotides (HAT medium). Where azaserine is used, the medium is supplemented with hypoxanthine. Ouabain is added if the B cell source is an EBV-transformed human B cell line, in order to eliminate EBV-transformed lines that have not fused to the myeloma.

The preferred selection medium is HAT or HAT with ouabain. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B cells can operate this pathway, but they have a limited life span in culture and generally die within about two weeks. Therefore, the only cells that can survive in the selective media are those hybrids formed from myeloma and B cells. When the source of B cells used for fusion is a line of EBV-transformed B cells, as here, ouabain may also be used for drug selection of hybrids as EBV-transformed B cells are susceptible to drug killing, whereas the myeloma partner used is chosen to be ouabain resistant.

Culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays dot immunobinding assays, and the like. The selected hybridomas are then serially diluted or single-cell sorted by flow cytometric sorting and cloned into individual antibody-producing cell lines, which clones can then be propagated indefinitely to provide mAbs. The cell lines may be exploited for MAb production in two basic ways. A sample of the hybridoma can be injected (often into the peritoneal cavity) into an animal (e.g., a mouse). Optionally, the animals are primed with a hydrocarbon, especially oils such as pristane (tetramethylpentadecane) prior to injection.

When human hybridomas are used in this way, it is optimal to inject immunocompromised mice, such as SCID mice, to prevent tumor rejection. The injected animal develops tumors secreting the specific monoclonal antibody produced by the fused cell hybrid. The body fluids of the animal, such as serum or ascites fluid, can then be tapped to provide MAbs in high concentration. The individual cell lines could also be cultured in vitro, where the MAbs are naturally secreted into the culture medium from which they can be readily obtained in high concentrations. Alternatively, human hybridoma cells lines can be used in vitro to produce immunoglobulins in cell supernatant. The cell lines can be adapted for growth in serum-free medium to optimize the ability to recover human monoclonal immunoglobulins of high purity.

MAbs produced by either means may be further purified, if desired, using filtration, centrifugation and various chromatographic methods such as FPLC or affinity chromatography. Fragments of the monoclonal antibodies of the disclosure can be obtained from the purified monoclonal antibodies by methods which include digestion with enzymes, such as pepsin or papain, and/or by cleavage of disulfide bonds by chemical reduction. Alternatively, monoclonal antibody fragments encompassed by the present disclosure can be synthesized using an automated peptide synthesizer.

It also is contemplated that a molecular cloning approach may be used to generate monoclonal antibodies. Single B cells labelled with the antigen of interest can be sorted physically using paramagnetic bead selection or flow cytometric sorting, then RNA can be isolated from the single cells and antibody genes amplified by RT-PCR. Alternatively, antigen-specific bulk sorted populations of cells can be segregated into microvesicles and the matched heavy and light chain variable genes recovered from single cells using physical linkage of heavy and light chain amplicons, or common barcoding of heavy and light chain genes from a vesicle. Matched heavy and light chain genes form single cells also can be obtained from populations of antigen specific B cells by treating cells with cell-penetrating nanoparticles bearing RT-PCR primers and barcodes for marking transcripts with one barcode per cell. The antibody variable genes also can be isolated by RNA extraction of a hybridoma line and the antibody genes obtained by RT-PCR and cloned into an immunoglobulin expression vector. Alternatively, combinatorial immunoglobulin phagemid libraries are prepared from RNA isolated from the cell lines and phagemids expressing appropriate antibodies are selected by panning using antigens. The advantages of this approach over conventional hybridoma techniques are that approximately $10^4$ times as many antibodies can be produced and screened in a single round, and that new specificities are generated by H and L chain combination which further increases the chance of finding appropriate antibodies.

Other U.S. patents, each incorporated herein by reference, that teach the production of antibodies useful in the present disclosure include U.S. Pat. No. 5,565,332, which describes the production of chimeric antibodies using a combinatorial approach; U.S. Pat. No. 4,816,567 which describes recombinant immunoglobulin preparations; and U.S. Pat. No. 4,867,973 which describes antibody-therapeutic agent conjugates.

B. IgE Antibodies of the Present Disclosure

1. Biology

Immunoglobulin E (IgE), first discovered in 1966, is a kind of antibody (or immunoglobulin (Ig) "isotype") that has only been found in mammals. IgE is synthesised by plasma cells. Monomers of IgE consist of two heavy chains (c chain) and two light chains, with the c chain containing 4 Ig-like constant domains (Cε1-Cε4). IgE's main function is immunity to parasites such as helminths like *Schistosoma mansoni, Trichinella spiralis*, and *Fasciola hepatica*. IgE is utilized during immune defense against certain protozoan parasites such as Plasmodium falciparum.

IgE also has an essential role in type I hypersensitivity, which manifests in various allergic diseases, such as allergic asthma, most types of sinusitis, allergic rhinitis, food allergies, and specific types of chronic urticaria and atopic dermatitis. IgE also plays a pivotal role in responses to allergens, such as: anaphylactic drugs, bee stings, and antigen preparations used in desensitization immunotherapy.

Although IgE is typically the least abundant isotype—blood serum IgE levels in a normal ("non-atopic") individual are only 0.05% of the Ig concentration, compared to 75% for the IgGs at 10 mg/ml, which are the isotypes responsible for most of the classical adaptive immune response—it is capable of triggering the most powerful inflammatory reactions.

IgE primes the IgE-mediated allergic response by binding to Fc receptors found on the surface of mast cells and basophils. Fc receptors are also found on eosinophils, monocytes, macrophages and platelets in humans. There are two types of Fcε receptors, FcεRI (type I Fcε receptor), the high-affinity IgE receptor, and FcεRII (type II Fcε receptor), also known as CD23, the low-affinity IgE receptor. IgE can upregulate the expression of both types of Fcε receptors. FcεRI is expressed on mast cells, basophils, and the antigen-presenting dendritic cells in both mice and humans. Binding of antigens to IgE already bound by the FcεRI on mast cells causes cross-linking of the bound IgE and the aggregation of the underlying FcεRI, leading to the degranulation and the release of mediators from the cells. Basophils, upon the cross-linking of their surface IgE by antigens, release type 2 cytokines like interleukin-4 (IL-4) and interleukin-13 (IL-13) and other inflammatory mediators. The low-affinity receptor (FcεRII) is always expressed on B cells; but IL-4 can induce its expression on the surfaces of macrophages, eosinophils, platelets, and some T cells.

There is much speculation into what physiological benefits IgE contributes, and, so far, circumstantial evidence in animal models and statistical population trends have hinted that IgE may be beneficial in fighting gut parasites such as *Schistosoma mansoni*, but this has not been conclusively proven in humans. Epidemiological research shows that IgE level is increased when infected by *Schistosoma mansoni, Necator americanus*, and nematodes in human. It is most likely beneficial in removal of hookworms from the lung.

Although it is not yet well understood, IgE may play an important role in the immune system's recognition of cancer, in which the stimulation of a strong cytotoxic response against cells displaying only small amounts of early cancer markers would be beneficial. If this were the case, anti-IgE treatments such as omalizumab (for allergies) might have some undesirable side effects. However, a recent study, which was performed based on pooled analysis using comprehensive data from 67 phase I to IV clinical trials of omalizumab in various indications, concluded that a causal relationship between omalizumab therapy and malignancy is unlikely.

Atopic individuals can have up to 10 times the normal level of IgE in their blood (as do sufferers of hyper-IgE syndrome). However, this may not be a requirement for symptoms to occur as has been seen in asthmatics with normal IgE levels in their blood—recent research has shown that IgE production can occur locally in the nasal mucosa.

IgE that can specifically recognize an "allergen" (typically this is a protein, such as dust mite Der p 1, cat Fel d 1, grass or ragweed pollen, etc.) has a unique long-lived interaction with its high-affinity receptor FcεRI so that basophils and mast cells, capable of mediating inflammatory reactions, become "primed", ready to release chemicals like histamine, leukotrienes, and certain interleukins. These chemicals cause many of the symptoms are associated with allergy, such as airway constriction in asthma, local inflammation in eczema, increased mucus secretion in allergic rhinitis, and increased vascular permeability, it is presumed, to allow other immune cells to gain access to tissues, but which can lead to a potentially fatal drop in blood pressure as in anaphylaxis. IgE is known to be elevated in various autoimmune disorders such as lupus (SLE), rheumatoid arthritis (RA) and psoriasis, and is theorized to be of pathogenetic importance in RA and SLE by eliciting a hypersensitivity reaction.

Regulation of IgE levels through control of B cell differentiation to antibody-secreting plasma cells is thought to involve the "low-affinity" receptor FcεRII, or CD23. CD23 may also allow facilitated antigen presentation, an IgE-dependent mechanism whereby B cells expressing CD23 are able to present allergen to (and stimulate) specific T helper cells, causing the perpetuation of a Th2 response, one of the hallmarks of which is the production of more antibodies.

Diagnosis of allergy is most often done by reviewing a person's medical history and finds a positive result for the presence of allergen specific IgE when conducting a skin or blood test. Specific IgE testing is the proven test for allergy detection; evidence does not show that indiscriminate IgE testing or testing for immunoglobulin G (IgG) can support allergy diagnosis.

2. IgE and its Role in Helminthic Immunity

A major branch of the mammalian immune system has evolved to deal with helminth infections, known as type-2 immunity. Both the innate (basophils and eosinophils) and adaptive (CD4+ T cells and B cells) arms are heavily involved. Studies, primarily using murine animal model systems, have shown that this host immune response plays a critical role in trying to kill and expel the adult parasite as well as reducing survival of parasites during secondary infection (Finkelman, et al., 2004; Voehringer et al., 2006; Herbert et al., 2004; Abraham et al., 2004; Gurish et al., 2004 and King et al., 1997). Massive epidemiologic studies have conclusively demonstrated a clear link between helminth infection and eosinophilia and elevated levels of IgE. Thus it is clear that this branch of human immunity is induced, but what benefits are provided, if any, by IgE is not known. There is only sparse data that link the levels of IgE directed toward the helminth and infection rates or worm burden in humans (McSharry et al., 1999; Turner et al., 2005 and Turner et al., 2003). Therefore, the role of IgE in protective immunity against helminth parasites is not clear, but it may be contributing to aspects of host immunity such as life-cycle stages, re-infection, or a specific helminth parasite (Hagan et al., 1991). A randomized controlled trial tested the effect of anti-IgE therapy (Omalizumab) in populations at risk of helminth infection. Although numbers were small, treatment did not appear to be associated with increased morbidity attributable to helminth infection (Cruz et al., 2007).

One group of helminth proteins, which are known targets of the human immune response, studied by several groups as potential vaccine candidate proteins, are the nematode polyprotein allergens (NPAs). NPAs are unusual lipid-binding proteins found only in nematodes that are felt to play roles in nutrient scavenging, immunomodulation, and IgE antibody responses to infection. NPAs are the target of strong immune responses, often associated with hypersensitivities. The most extensively studied of these is ABA-1, which is the most abundant protein in the body fluid of *Ascaris lumbricoides*. Epidemiological data using patient serum suggest that IgE antibody responses to ABA-1 are associated with the development of resistance to the infection (McSharry et al., 1999).

Nearly all of the field's understanding of the natural anti-helminth IgE antibody has come from the very low concentration present in infected patients' serum. Serum contains an immeasurable mixture of antibodies, which have many protein specificities, target untold numbers of epitopes, and have different affinities. This results in the inability to accurately study the molecular interaction of IgE with its target antigen. Since there are no natural antigen-specific human IgE mAbs, there are no controls to determine the accuracy/inaccuracy of any study that uses serum. Since there are no IgE mAbs that represent the molecules being tested in human serum, there are no means to verify/calibrate any assay with any degree of certainty. Serum has been used to study the helminth-specific IgE antibody response (Nutman et al., 1989; Lee et al., 1990; McCarthy et al. 1994 and Mitre et al., 2004). Several longitudinal studies aimed at measuring parasite-specific IgE levels during helminth infection have been performed (Chapa-Ruiz et al., and Steel, 1991).

The persistence of B cell memory was evaluated for antigen-specific IgE responses years after treatment of human filarial infections (Mitre and Nutman, 2006). Interestingly, frequencies of *Wuchereria bancrofti* antigen-specific IgE serum levels decreased significantly over time, but remained detectable in the majority of patients years after definitive treatment. More importantly they showed presence of circulating memory B cells producing helminth-specific IgE antibodies—using B cell ELISPOT analysis. Lastly, using affinity-purified serum IgE from a patient with a filarial parasitic infection, a major allergen γ-glutamyl transpeptidase was identified (Lobos et al., 1996). These studies provide evidence that helminth-specific circulating memory B cells remain following elimination of the infection and will be available for us to culture and study.

The hygiene hypothesis suggests that helminth infection might modulate the host immune response and decrease responsiveness to innocuous environmental proteins (Strachan, 1989 and Liu and Leung, 2006). Indeed, helminth-infected individuals have been found to have an overall lower prevalence of allergic disease in several studies (Cooper et al., 2003; Rodrigues et al., 2008 and van den Biggelaar et al., 2000). However, many other studies have demonstrated an increase in allergic disease in helminth-infected individuals, particularly when looking at asthma (Hagel et al., 2007; Wordemann et al., 2008 and Leonardi-Bee et al., 2006). This discrepancy may be explained by the phenomenon of cross-sensitization (phenomena often seen with allergens). Homology exists between some helminth proteins and allergens, and theoretically could be bound by the same IgE molecule. In fact, cross-sensitization due to homology between helminth proteins and allergen proteins has been shown using serum. The two most studied of these are the tropomyosin and glutathione-S-transferase proteins found in dust mite, *Dermatophagoides pteronyssinus*. Using allergic patient serum, the human IgE-binding components in *Ascaris* extract were identified using mass spectroscopy, confirming the IgE cross-reactivity between these parasitic worm proteins and dust mite allergens (Acevedo et al., 2009). More recently cross-reactivity was also shown between a major glutathione-S transferase allergen of cockroach and the protein homolog found in *Wuchereria bancrofti* (Santiago et al., 2012; Santiago et al., 2012 and Santiago et al., 2015). Since all of these studies use polyclonal serum, the epitopes, affinity toward helminth versus crossreactive allergen protein, and the functional significance of this cross-sensitization phenomenon cannot be studied further. Having natural human helminth protein specific IgE mAbs will allow us to study the molecular mechanisms underlying this effect.

3. IgE-Mediated Allergic Diseases

The allergic response itself offers no evident advantage and is instead understood to be a side effect of the primary function of the IgE class of antibodies: to prevent infection by helminth worms (such as hookworm and schistosomes). Through mechanisms that are yet to be elucidated, allergens appear to be innocuous antigens that inappropriately produce an IgE antibody response that is typically specific for helminths.

For more than 50 years, the prevalence of allergic diseases has risen steadily in the industrialized world (Food Allergy Among U.S. Children: Trends in Prevalence and Hospitalizations. In the US, allergy is the fifth leading chronic disease in people of all ages and the third most common chronic disease in children (Sicherer et al., 1999 and American Academy of Allergy Asthma and Immunology: Food Allergy). IgE-mediated allergic diseases include: asthma, atopic dermatitis, allergic rhinitis, allergic conjunctivitis, anaphylaxis, drug allergies, insect venom allergies, etc. These diseases are invoked and perpetuated by proteins contained in an array of plant and animal species that humans are exposed to on a daily basis. These allergen proteins exist in things like: foods, venoms, drugs, trees, molds, mites, cockroaches, dogs, cats, latex, etc. Although allergy is among our country's most common diseases, it is often overlooked. New diagnostics and therapeutics are needed. Gaining a basic understanding of the molecular interactions at the heart of the pathogenesis of allergic diseases will open up new strategies for developing allergy diagnostics and therapeutics.

Asthma affects nearly 300 million individuals worldwide, about 25 million people in the U.S. alone. It affects all age groups, but it is children that are at the highest risk, with a prevalence that is rapidly growing. Asthma is the most prevalent cause of childhood disability in the U.S., and affects the poor disproportionately. Despite the prevalence, significant morbidity, and cost of this disease, little progress has been made with regard to understanding the pathogenesis or development of new strategies for treatment or prevention. Many of the allergens responsible for asthma are also associated with allergic rhinitis, affects between 10 and 30 percent of the population in developed countries. The most common indoor/outdoor triggers are: dust mites, cockroaches, and cat, dog and rodent dander. Also of great importance, particularly in the case of allergic rhinitis, are: trees, grasses, weed pollens, and mold spores.

Skin allergies are also very common and are one of the most important groups of allergic diseases that include eczema, hives, chronic hives and contact allergies. In the U.S., 8.8 million children have skin allergies, affecting the very young (age 0-4) disproportionately. Primary allergen culprits again include contact with dust mites and cockroaches, foods or even latex.

The most recent estimates suggest that up to 15 million Americans have allergies to food, and this number is rapidly rising. The Centers for Disease Control and Prevention reported that food allergies among children increased about 50% between 1997 and 2011, but there is no clear answer as to why (Food Allergy Among U.S. Children: Trends in Prevalence and Hospitalizations). The Centers for Disease Control also reported that food allergies result in more than 300,000 ambulatory-care and more than 200,000 emergency department visits a year among children (Sicherer et al., 1999). The economic cost of food allergies in children has reached nearly $25 billion per year. Food allergy is the leading cause of anaphylaxis outside the hospital setting. Eight foods account for 90 percent of all reactions: milk, eggs, peanuts, tree nuts, soy, wheat, fish and shellfish. Peanut and tree nut allergies, which tend to develop in childhood, are usually life-long, whereas cow's milk, egg and soy allergies are eventually outgrown. Approximately 3 million people report allergies to peanuts and tree nuts (Sicherer et al., 1999). The number of children living with peanut allergy has tripled between 1997 and 2008. There is no cure for food allergies. Strict avoidance of food allergens and early recognition and management of allergic reactions is the current strategy applied in clinical practices around the world. Unfortunately, even trace amounts of a food allergen can cause a reaction.

Despite the fact that IgE causes so much human suffering in the form of allergic disease, it was not until 1967 before the "reagin" molecule was discovered (Johansson and Bennich, 1967). This is due to its very low serum concentration relative to other antibody isotypes—over one hundred thousand-fold less than IgG in healthy individuals. Only one IgE secreting cell line (U266), or its derivatives (SKO-007), has been available to study—the atypical multiple myeloma described in the original paper (Johansson and Bennich, 1967 and Olsson and Kaplan, 1980). This IgE molecule has been of integral importance, used in thousands of studies as a reagent or for the generation of reagents. However, its target has never been identified, thus forcing investigators who wish to study the naturally-occurring IgE antibody response to use polyclonal serum.

4. Antibodies of the Disclosure

Antibodies according to the present disclosure may be defined, in the first instance, by their binding specificity. Those of skill in the art, by assessing the binding specificity/affinity of a given antibody using techniques well known to those of skill in the art, can determine whether such antibodies fall within the scope of the instant claims. For example, the epitope to which a given antibody bind may consist of a single contiguous sequence of 3 or more (e.g., 3, 4, 5, 6, 7, 8, 9, 10, 11, 12, 13, 14, 15, 16, 17, 18, 19, 20) amino acids located within the antigen molecule (e.g., a linear epitope in a domain). Alternatively, the epitope may consist of a plurality of non-contiguous amino acids (or amino acid sequences) located within the antigen molecule (e.g., a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in Antibodies, Harlow and Lane (Cold Spring Harbor Press, Cold Spring Harbor, N.Y.). Cross-blocking can be measured in various binding assays such as ELISA, biolayer interferometry, or surface plasmon resonance Other methods include alanine scanning mutational analysis, peptide blot analysis (Reineke (2004) Methods Mol. Biol. 248: 443-63), peptide cleavage analysis, high-resolution electron microscopy techniques using single particle reconstruction, cryoEM, or tomography, crystallographic studies and N1R analysis. In addition, methods such as epitope excision, epitope extraction and chemical modification of antigens can be employed (Tomer (2000) Prot. Sci. 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267: 252-259, Engen and Smith (2001) Anal. Chem. 73: 256A-265A. When the antibody neutralizes *A. fumigatus*, antibody escape mutant variant organisms can be isolated by propagating *A. fumigatus* in vitro or in animal models in the presence of high concentrations of the antibody. Sequence analysis of the *A. fumigatus* gene encoding the antigen targeted by the antibody reveals the mutation(s) conferring antibody escape, indicating residues in the epitope or that affect the structure of the epitope allosterically.

The term "epitope" refers to a site on an antigen to which B and/or T cells respond. B-cell epitopes can be formed both from contiguous amino acids or noncontiguous amino acids juxtaposed by tertiary folding of a protein Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

Modification-Assisted Profiling (MAP), also known as Antigen Structure-based Antibody Profiling (ASAP) is a method that categorizes large numbers of monoclonal antibodies (mAbs) directed against the same antigen according to the similarities of the binding profile of each antibody to chemically or enzymatically modified antigen surfaces (see US 2004/0101920, herein specifically incorporated by reference in its entirety). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce mAbs having the desired characteristics. MAP may be used to sort the antibodies of the disclosure into groups of antibodies binding different epitopes.

The present disclosure includes antibodies that may bind to the same epitope, or a portion of the epitope. Likewise, the present disclosure also includes antibodies that compete for binding to a target or a fragment thereof with any of the specific exemplary antibodies described herein. One can easily determine whether an antibody binds to the same epitope as, or competes for binding with, a reference antibody by using routine methods known in the art. For example, to determine if a test antibody binds to the same epitope as a reference, the reference antibody is allowed to bind to target under saturating conditions. Next, the ability of a test antibody to bind to the target molecule is assessed. If the test antibody is able to bind to the target molecule following saturation binding with the reference antibody, it can be concluded that the test antibody binds to a different epitope than the reference antibody. On the other hand, if the test antibody is not able to bind to the target molecule following saturation binding with the reference antibody, then the test antibody may bind to the same epitope as the epitope bound by the reference antibody.

To determine if an antibody competes for binding with a reference anti-*Aspergillus* antibody, the above-described binding methodology is performed in two orientations: In a first orientation, the reference antibody is allowed to bind to the *Aspergillus* antigen under saturating conditions followed by assessment of binding of the test antibody to the *Aspergillus* molecule. In a second orientation, the test antibody is allowed to bind to the *Aspergillus* antigen molecule under saturating conditions followed by assessment of binding of the reference antibody to the *Aspergillus* antigen. If, in both orientations, only the first (saturating) antibody is capable of binding to the *Aspergillus* antigen, then it is concluded that the test antibody and the reference antibody compete for binding to the *Aspergillus* antigen. As will be appreciated by a person of ordinary skill in the art, an antibody that competes for binding with a reference antibody may not necessarily bind to the identical epitope as the reference antibody but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res 1990 50.1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art. Structural studies with EM or crystallography also can demonstrate whether or not two antibodies that compete for binding recognize the same epitope.

In another aspect, there are provided monoclonal antibodies having clone-paired CDRs from the heavy and light chains as illustrated in Tables 3 and 4, respectively. Such antibodies may be produced by the clones discussed below in the Examples section using methods described herein.

In another aspect, the antibodies may be defined by their variable sequence, which include additional "framework"

regions. These are provided in Tables 1 and 2 that encode or represent full variable regions. Furthermore, the antibodies sequences may vary from these sequences, optionally using methods discussed in greater detail below. For example, nucleic acid sequences may vary from those set out above in that (a) the variable regions may be segregated away from the constant domains of the light and heavy chains, (b) the nucleic acids may vary from those set out above while not affecting the residues encoded thereby, (c) the nucleic acids may vary from those set out above by a given percentage, e.g., 70%, 75%, 80%, 85%, 90%, 91%, 92%, 93%, 94%, 95%, 96%, 97%, 98% or 99% homology, (d) the nucleic acids may vary from those set out above by virtue of the ability to hybridize under high stringency conditions, as exemplified by low salt and/or high temperature conditions, such as provided by about 0.02 M to about 0.15 M NaCl at temperatures of about 50° C. to about 70° C., (e) the amino acids may vary from those set out above by a given percentage, e.g., 80%, 85%, 90%, 91%, 92%, 93%, 94%, 95%, 96%, 97%, 98% or 99% homology, or (f) the amino acids may vary from those set out above by permitting conservative substitutions (discussed below). Each of the foregoing applies to the nucleic acid sequences set forth as Table 1 and the amino acid sequences of Table 2.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington D.C. Vol. 5, Suppl. 3, pp. 345-358; Hein J. (1990) Unified Approach to Alignment and Phylogeny pp. 626-645 Methods in Enzymology vol. 183, Academic Press, Inc., San Diego, Calif.; Higgins, D. G. and Sharp, P. M. (1989) CABIOS 5:151-153; Myers, E. W. and Muller W. (1988) CABIOS 4:11-17; Robinson, E. D. (1971) Comb. Theor 11:105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, Calif.; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One particular example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides of the disclosure. Software for performing BLAST analyses is publicly available through the National Center for Biotechnology Information. The rearranged nature of an antibody sequence and the variable length of each gene requires multiple rounds of BLAST searches for a single antibody sequence. Also, manual assembly of different genes is difficult and error-prone. The sequence analysis tool IgBLAST (world-wide-web at ncbi.nlm.nih.gov/igblast/) identifies matches to the germline V, D and J genes, details at rearrangement junctions, the delineation of Ig V domain framework regions and complementarity determining regions. IgBLAST can analyze nucleotide or protein sequences and can process sequences in batches and allows searches against the germline gene databases and other sequence databases simultaneously to minimize the chance of missing possibly the best matching germline V gene.

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=−4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

Yet another way of defining an antibody is as a "derivative" of any of the below-described antibodies and their antigen-binding fragments. The term "derivative" refers to an antibody or antigen-binding fragment thereof that immunospecifically binds to an antigen but which comprises, one, two, three, four, five or more amino acid substitutions, additions, deletions or modifications relative to a "parental" (or wild-type) molecule. Such amino acid substitutions or additions may introduce naturally occurring (i.e., DNA-encoded) or non-naturally occurring amino acid residues. The term "derivative" encompasses, for example, as variants having altered CH1, hinge, CH2, CH3 or CH4 regions, so as to form, for example antibodies, etc., having variant Fc regions that exhibit enhanced or impaired effector or binding characteristics. The term "derivative" additionally encompasses non-amino acid modifications, for example, amino acids that may be glycosylated (e.g., have altered mannose, 2-N-acetylglucosamine, galactose, fucose, glucose, sialic acid, 5-N-acetylneuraminic acid, 5-glycolneuraminic acid, etc. content), acetylated, pegylated, phosphorylated, amidated, derivatized by known protecting/blocking groups, proteolytic cleavage, linked to a cellular ligand or other protein, etc. In some embodiments, the altered carbohydrate modifications modulate one or more of the following: solubilization of the antibody, facilitation of subcellular transport and secretion of the antibody, promotion of antibody assembly, conformational integrity, and antibody-mediated effector function. In a specific embodiment the altered carbohydrate modifications enhance antibody mediated effector function relative to the antibody lacking the carbohydrate modification. Carbohydrate modifications that lead to altered antibody mediated effector function are well known in the art (for example, see Shields, R. L. et al. (2002) "*Lack Of Fucose On Human IgG N-Linked Oligosaccharide Improves Binding To Human Fcgamma Pill And Antibody-Dependent Cellular Toxicity,*" J. Biol. Chem. 277(30): 26733-26740; Davies J. et al. (2001) "*Expression Of GnTIII In A Recombinant Anti-CD20 CHO Production Cell Line: Expression Of Antibodies With Altered Glycoforms Leads To An Increase In ADCC Through Higher Affinity For FC Gamma Pill,*" Biotechnology & Bioengineering 74(4): 288-294). Methods of altering carbohydrate contents are known to those skilled in the art, see, e.g., Wallick, S. C. et al. (1988) "*Glycosylation Of A VH Residue Of A Monoclonal Antibody Against Alpha* (1-6) *Dextran Increases Its Affinity For Antigen,*" J. Exp. Med. 168(3): 1099-1109; Tao, M. H. et al. (1989) "*Studies Of Aglycosylated Chimeric Mouse-Human IgG. Role Of Carbohydrate In The Structure And Effector Functions Mediated By The Human IgG Constant Region,*" J. Immunol. 143(8): 2595-2601; Routledge, E. G. et al. (1995) "*The Effect Of Aglycosylation On The Immunogenicity Of A Humanized Therapeutic CD3 Monoclonal Antibody,*" Transplantation 60(8):847-53; Elliott, S. et al. (2003) "*Enhancement Of Therapeutic Protein In Vivo Activities Through Glycoengineering,*" Nature Biotechnol. 21:414-21; Shields, R. L. et al. (2002) "*Lack Of Fucose On Human IgG N-Linked Oligosaccharide Improves Binding To Human Fcgamma Rill And Antibody-Dependent Cellular Toxicity,*" J. Biol. Chem. 277(30): 26733-26740).

A derivative antibody or antibody fragment can be generated with an engineered sequence or glycosylation state to confer preferred levels of activity in antibody dependent cellular cytotoxicity (ADCC), antibody-dependent cellular phagocytosis (ADCP), antibody-dependent neutrophil phagocytosis (ADNP), or antibody-dependent complement deposition (ADCD) functions as measured by bead-based or cell-based assays or in vivo studies in animal models.

A derivative antibody or antibody fragment may be modified by chemical modifications using techniques known to those of skill in the art, including, but not limited to, specific chemical cleavage, acetylation, formulation, metabolic synthesis of tunicamycin, etc. In one embodiment, an antibody derivative will possess a similar or identical function as the parental antibody. In another embodiment, an antibody derivative will exhibit an altered activity relative to the parental antibody. For example, a derivative antibody (or fragment thereof) can bind to its epitope more tightly or be more resistant to proteolysis than the parental antibody.

C. IgE Antibody Generation Protocols

The following are a series of exemplary protocols for use in practicing the disclosed methods and producing the disclosed compositions.

(i) Hybridoma Process Outline
1. Growth and maintenance of rh-IL-21, CD40L, BAFF-NIH3T3 cells (NIH3T3)
2. Growth and maintenance of HMMAs (HMMA2.5)
3. Isolation of subject PBMCs from blood
4. NIH3T3 activation of B-cells from subject PBMCs (96-well-plates)
5. ELISA screening of NIH3T3 activated B-cell cultures (384-well format)
6. HMMA ctyofusion and plating in growth medium (cells in 384-well-plates)
7. HAT selection medium is added
8. ELISA screening of hybridomas (384-well format)
9. Limiting dilution/enrichment dilution and flow cytometric sorting (384-well format)
10. ELISA screening of limiting dilution products
11. Transfer IgE positive hybridomas to a 48-well plate
12. Freeze back an aliquot then do an ELISA on 48-well plates (96-well format)
13. Transfer IgE positive hybridomas to a 12-well plate
14. Transfer IgE positive hybridomas to a T-75 flask
15. Grow final clonal hybridoma in 1 L SFM in 4×T-225 flasks
16. Grow the residual hybridoma cells in T-75 flask for RNA production (freeze back three aliquot pellets)
17. Harvest SFM and purify mAb by chromatography (ii) Polyclonal Activation of Human B Cells with Rh-IL-21, CD40L, BAFF-NIH3T3 Feeder Cells Materials
1. Subject sample
   a. PBMCs: $1 \times 10^6$ cells per plate
   b. Subject Tonsils/Adenoids: $1 \times 10^6$ cells per plate
2. Medium A (Stemcell Technologies, 03801)
3. Trypan blue (Gibco 15250-061)
4. CpG
   a. Order the oligonucleotide ZOEZOEZZZZZOE-EZOEZZZT (SEQ ID NO: 41) from invitrogen at the 10 μmole scale (desalted)
   b. Dissolve in nuclease free water at a concentration of 2.5 mg/ml
   c. Aliquot and store at −20° C.
5. Irradiated rh-IL-21, CD40L, BAFF-NIH3T3 cell line
   a. rh-IL-21, CD40L, BAFF-NIH3T3 cells grown in Medium A are trypsinized, washed, and resuspended in Medium A
   b. Irradiate cells for 15-20 minutes using Cesium 137 irradiator
6. Filtered conditioned media from rh-IL-21, CD40L, BAFF-NIH3T3 cell line (containing rh-IL-21 and BAFF)

a. Harvest supernatant of nearly confluent rh-IL-21, CD40L, BAFF-NIH3T3 cells grown in Medium A.
b. Centrifuge supernatant at 2500 RPM to pellet cellular debris.
c. Sterile filter supernatant through 0.22 µm filter and store at 4° C.
7. Goat anti-human Kappa unlabeled antibody (Southern Biotech; 1 mg/ml; Cat No: 2060-01)
8. Goat anti-human Lambda unlabeled antibody (Southern Biotech; 1 mg/ml; Cat No: 2070-01)
9. rh-IL-21, CD40L, BAFF-NIH3T3 growth media (prepares enough for one 96 well plate at 300 µl/well)
   a. Add cells to solution containing the following components:
      i. 20 ml of Medium A
      ii. 12 ml of rh-IL-21, CD40L, BAFF-NIH3T3 conditioned media
      iii. 20 µl CpG stock
      iv. 1 µl of Goat anti-human Kappa unlabeled antibody (1 mg/ml)
      v. 1 µl of Goat anti-human Lambda unlabeled antibody (1 mg/ml)
      vi. $5\times10^5$ irradiated rh-IL-21, CD40L, BAFF-NIH3T3 cells
         1. Add 250 µl of Pen/Strep/Glutamine (100×) and 250 µl of Amphotericin B (250 µg/ml) per plate of Tonsil/Adenoids
10. 96-well plates (Corning: 3997)
11. Matrix electronic Pipette 850 µl (Thermo Scientific 2014)
12. Matrix tips (Thermo Scientific 8042)
13. 500 ml Rapid Flow filter unit, 0.22 µm (Fisher 09-741-05)
14. Hyclone Pen/Strep/Glutamine solution (Thermo SV30082.01)
15. Amphotericin B; 250 µg/ml solution (Fisher MT-30-003-CF)

Protocol
1. When using a frozen stock of Subject PBMCs or Tonsils/Adenoids (TAs), thaw samples rapidly in 37° C. water bath. Remove stock from the water bath as soon as it has thawed. When using freshly isolated PBMCs or TAs, skip steps 1-3.
2. Drop wise, add 1 ml of warmed Medium A to the cells
3. Resuspend the cells in 10 ml warmed Medium A
4. Centrifuge the cell suspension at 1,100 RPM for 5 min
5. Discard the supernatant and resuspend cells in 1 ml warmed Medium A
6. Count cells and assess viability with trypan blue staining
7. Add the cells to rh-IL-21, CD40L, BAFF-NIH3T3 growth media and plate them out into a 96-well plate. One plate for every 1 million viable PBMCs. Using an electronic multichannel pipette, dispense 300 µl/well of mixture containing PBMCs/TAs into a 96-well plate
8. Incubate plates at 37° C. with 5% $CO_2$ for 7-8 days
   a. Monitor cells closely as different cells grow at different rates
   b. Fresh TAs grow much more readily than frozen PBMCs or PBMCs from Red Cross filters
9. Screen plates by ELISA (see the Standard Human IgE Fluorescent ELISA protocol) after 7-8 days of incubation; check plates daily for growth of B cells.
10. Wells that are determined by ELISA to be producing desired IgE antibodies then are used for electrical cytofusion with HMMA cells (see B-cell/HMMA fusion protocol).

(iii) Growth and Maintenance of HMMA 2.5 Cells
Materials
1. HMMA 2.5 cells
2. 50 ml conical tubes (Falcon 352070)
3. Medium A (Stemcell Technologies, 03801)
4. Canted-neck tissue culture flasks (Falcon)
   a. T-25 (Falcon 353109)
   b. T-75 (Falcon 353136)
   c. T-150 (Falcon 355001)
   d. T-225 (Falcon 353139)
5. Cell scraper (Falcon 353087) or (Techno Plastic Products 99003)

Protocol
1. If starting with a frozen stock of HMMA cells, thaw an aliquot of the cells rapidly at 37° C. Remove the stock from the water bath as soon as it has thawed
2. Gently transfer the cells to a 50 ml conical tube
3. Drop wise, add 1 ml of warmed Medium A to the cells
4. Resuspend the cells in 10 ml of warmed Medium A
5. Centrifuge the cells for 5 minutes at 1100 RPM in a swinging bucket centrifuge
6. Discard the supernatant
7. Resuspend the cells in 25-30 ml of warmed Medium A and transfer to a T-75 flask
8. Incubate at 37° C. with 5% $CO_2$
9. Split cells just before they become confluent and/or the medium starts to turn yellow
   a. Aspirate off the old media
   b. Add back fresh, warm Medium A
   c. Scrape the cells off the bottom of the flask
   d. Transfer the cells to a bigger flask, or split them amongst flasks of the same size
10. Split cells 3-5 days prior to performing fusions.
11. Cells should be about 80-90% confluent, and as close to 100% viable as possible, prior to harvesting for use in electrofusion. Do not replace culture medium less than 12 hours prior to fusion (iv) B-Cell/HMMA Fusion
Materials
1. BTX cytofusion media [gram amounts are for 500 ml of cytofusion media]
   a. 300 mM Sorbitol (Fisher, #BP439-500) [27.3 g]
   b. 0.1 mM Calcium Acetate (Fisher, #AC21105-2500) [0.008 g or 8 mg]
   c. 0.5 mM Magnesium Acetate (Fisher, #AC42387-0050) [0.0536 g or 53.6 mg]
   d. 1.0 mg/ml BSA (Sigma, #A2153) [0.5 g]
   e. Filter sterilize and store at 4° C.
2. BTX cytofusion cuvettes (BTX620: 2 mm gap width; 400 µl)
3. Cytofusion device:
   a. BTX ECM 2001
   b. BTX cuvette holder (BTX Safety Stand, Model 630B)
4. 384-well cell culture plates (Nunc, #164688)
5. 50×HAT (Sigma, #H0262)
6. Medium A (Stemcell Technologies, #03801)
7. Medium E (Stemcell Technologies, #03805)
8. HAT media
   a. 400 ml Medium A
   b. 100 ml Medium E
   c. One vial 50×HAT
9. Matrix electronic Pipette 850 µl (Thermo Scientific 2014)
10. Matrix tips (Thermo Scientific 8042)
11. Histopaque-1077 (Sigma-Aldrich; REF: 10771-6X100ML)

Protocol
1. Perform Histopaque-1077 gradient on HMMAs as described in Isolation of Peripheral blood mononuclear cells from human blood protocol.
2. Count HMMA cells and resuspend them in warmed BTX cytofusion media at 5 million cells/ml. You will need 120 µl of $5\times10^6$ cells/ml for each fusion; transfer them to a 1.5 ml microcentrifuge tube that contains 1 ml of warmed BTX cytofusion media; you may need several tubes depending on the desired number of fusions.
3. Gently resuspend the contents of an IgE positive B cell culture well (as determined by ELISA, see the Standard Human IgE Fluorescent ELISA protocol) and transfer them to a 1.5 ml microcentrifuge tube that contains 1 ml of warmed BTX cytofusion media.
4. Centrifuge the microcentrifuge tubes containing the HMMA cells and the microcentrifuge tubes containing the IgE positive B-cells (they remain in separate tubes at this point) at 3,000 RPM for 3 min in a tabletop centrifuge
5. Decant the supernatant
6. Resuspend the cell pellets in 1 ml of warmed BTX cytofusion media
7. Repeat the centrifugation, disposal of the supernatant, and resuspension of the pellet in cytofusion media two times (resulting in a total of 3 centrifugations). After the last centrifugation, DO NOT resuspend the pellot. Simply decant the supernatant and wait until step 9 to resuspend the cells
8. Resuspend the HMMA cell pellet in 1 ml of BTX cytofusion media (so that the concentration remains at 5 million cells/ml)
9. Use 120 µl of the HMMA cell solution at 5 million cells/ml to resuspend the positive B-cells in each microcentrifuge tube prior to transfer to a cytofusion cuvette
10. Transfer the mixture of HMMA and B-cells (volume approximately 200-250 µl) to a cytofusion cuvette
11. Place the cuvette(s) (device holds one or two cuvettes) into the cytofusion device, using a BTX cuvette holder. Run the program with the following settings:
    a. Pre: 40 v×30 sec AC current
    b. Pulse: 300 v×0.04 msec DC current
    c. Post: 40 v×7 sec AC current
12. After the fusion, incubate the cuvettes at 37° C. with 5% $CO_2$ for 20-30 minutes
    13. Add the contents of cuvettes to 20 ml of HAT medium.
    14. Use an electronic Matrix pipette to plate the fusion products at 50 µl/well into a 384-well cell culture plate
    15. Incubate the plates at 37° C. with 5% $CO_2$ for 13-15 days prior to screening hybridomas for antibody production (see the Standard Human IgE Fluorescent ELISA protocol)

(v) Subcloning of Hybridomas by Limiting Dilution
Materials
1. Medium E (Stemcell Technologies, #03805)
2. 384-well cell culture plates (Nunc, 164688)
3. 48-well cell culture plates (Corning Inc. 3548)
4. Matrix electronic pipette 850 µl (Thermo Scientific 2014)
5. Matrix tips (Thermo Scientific 8042)
Protocol
1. Enrichment dilution of the ELISA hits (option 1)
    a. Gently resuspend hits from a 384-well plate
    b. Place one drop of the cell suspension into a basin containing 21.5 ml of Medium E. Mix well
    c. Put the remainder of the cell suspension into one well of a 48-well plate containing 1 ml of Medium E
    d. Repeat for up to 5 hits; add the single drop of cells to the same basin and make individual cultures in the 48-well plate
    e. Plate 50 µl per well using an electronic Matrix pipette onto a 384-well plate
2. Enrichment dilution of the ELISA hits (option 2: a more stringent method of limiting dilution)
    a. Gently resuspend hits from a 384-well plate
    b. Place 1 µl of the cell suspension into a basin containing 20 ml of Medium E. Mix well
    c. Place 5 µl of the cell suspension into a separate basin containing 20 ml of Medium E. Mix well
    d. Place 10 µl of the cell suspension into a third basin containing 20 ml of Medium E. Mix well
    e. Plate the contents of each basin onto a separate 384-well plate at 50 µl per well
    f. Put the rest of the cell suspension into one well of a 48-well cell culture plate containing 750 µl of Medium E
3. Incubate the plates for 13-15 days at 37° C. with 5% $CO_2$, then recheck the 48-well plate and 384-well plates by ELISA
4. If no hits are found on the 384-well plate, repeat the enrichment dilution and plating of a 384-well plate if one or more of the 48-well cultures are active (vi) Subcloning Hybridomas by Flow Cytometry
Materials
1. Medium E (Stemcell Technologies, #03805)
2. Flow cytometry tubes (Falcon 352235)
3. 48-well cell culture plates (Corning Inc. 3548)
4. 384-well cell culture plates (Nunc, 164688)
5. Hybridoma culture growing in a 384-well plate
6. Propidium iodide (Molecular Probes P-3566)
Protocol
1. Gently resuspend a hit from a 48-well plate and place into a flow tube containing 1 ml of Medium E
2. Dispense 50 µl/well of Medium E onto on 384-well plate per hybridoma
3. Add 1 µl of propidium iodide to each tube of hybridomas
4. The flow core staff will process the samples, sorting 1 viable cell per well into 384-well plate
5. Incubate the plates at 37° C. with 5% $CO_2$ for 13-15 days
6. Screen the plates by ELISA or functional assay
7. If no hits are found on the 384-well plate, repeat the limiting dilution and plating of the 48-well culture hits or thaw frozen aliquot of that hybridoma line and repeat cloning procedure (vii) Thawing Hybridomas by Limiting Dilution Cloning
Materials
1. 50 ml conical tubes (Falcon, 352070)
2. Medium A (Stemcell Technologies, #03801)
3. 384-well cell culture plates (Nunc, 164688)
4. Matrix electronic Pipette 850 µl (Thermo Scientific 2014)
5. Matrix tips (Thermo Scientific 8042)
Protocol
1. Thaw an aliquot of the cells rapidly at 37° C. Remove stock from the water bath as soon as it has thawed
2. Drop wise, add 1 ml of warmed Medium A to the cells then gently transfer the cells to a 50 ml conical tube containing 10 ml of warmed Medium A 3. Centrifuge the cells for 5 minutes at 1100 RPM in a swinging bucket centrifuge
4. Discard the supernatant
5. Resuspend the cell pellet in 900 μl of Medium A
6. Prepare 5 different basins each containing 20 ml of Medium E
7. Into the 5 basins place 1 μl, 5 μl, 25 μl, 100 μl and the remainder of the washed cells (one for each basin)
5. Plate the contents of each basin onto a separate plate at 50 μl per well using an electronic Matrix pipette (viii) Expanding Hybridomas Materials
1. 12 well cell culture plates (Falcon 353043)
2. Medium E (Stemcell Technologies, #03805)
3. T-75 Flasks (Falcon 353136)
4. T-225 Flasks (Falcon 353139)
5. Hybridoma Serum Free Media (Gibco 12045)
6. DMSO (Sigma D2650)
7. Cryovial tubes (Sarstedt 72.694.996)
8. Cell scrapers (Falcon 353087) or (Techno Plastic Products 99003)

Protocol
1. Grow hybridoma culture in a 48-well plate in an incubator at 37° C. with 5% $CO_2$ until cells are 25% confluent
2. Check antibody production by ELISA (see the *Standard Human IgE Fluorescent ELISA protocol*)
3. Gently resuspend cells, and take an aliquot of cells for freezing (see the Freezing cells protocol)
4. Transfer the remainder of the cells to a 12 well plate containing 2 ml of Medium E
5. Grow 12 well plates in an incubator at 37° C. with 5% $CO_2$ until cells are 25% confluent
6. Check antibody production by ELISA (see Standard Human IgE Fluorescent ELISA protocol)
7. Freeze back an aliquot that represents 25% of the culture (see Freezing cells protocol)
8. Transfer the remainder of the cells in the 12 well plate to a T-75 flask and add Medium E to 30 ml
9. Every 3-5 days, feed the cells by aspirating off the old media and adding back fresh, warm media. Feed the cells every 3-5 days until the cells are 80% confluent
10. Mark 250 ml on four Corning T-225 flasks
11. Scrape cells off of the bottom of the T-75 flask using a cell scraper
12. Add the cell suspension to 1 L of Serum Free Media and divide equally to each of the four T-225 flasks
13. Freeze back an aliquot of the cells (see the Freezing cells protocol)
14. Add 30 ml of Medium E to the cells which remain in the T-75 Flask
15. Grow hybridomas in an incubator at 37° C. with 5% $CO_2$ in T-225 flasks for mAb production (see the chromatographic purification of full-length antibodies protocol) and T-75 flasks for RNA production
16. Freeze back 3 aliquot pellets of cells from the T-75 flasks for RNA production (see the Freezing cells protocol)
17. Grow the hybridomas in an incubator at 37° C. with 5% $CO_2$ in the T-225 flasks until cells are <10% viable using visual inspection
18. Harvest the medium for antibody purification by first centrifuging medium for 10 min at 2500 RPM followed by sterile filtration via 0.22 μm filter. Before purifying, perform an ELISA on the supernatant (ix) Freezing Hybridoma Cells Materials
1. Freezing Media
   a. 90% FBS (Sigma F-2442) or Medium E (Stemcell Technologies, #03805)
   b. 10% DMSO (Sigma D2650)
   c. Filter sterilize
2. 0.45 μm filter (Nalgene 167-0045)
3. Sarstedt cryovial tubes (Sarstedt 72.694.996)
4. Mr. Frosty freezing controlled freezing chamber Protocol
1. Label cryovials
2. Gently pipette the culture to resuspend any cells that have adhered to the bottom. When aspirating the cells, make sure to pipette up and down multiple times in a clockwise fashion around the side of the well, to ensure you really get the cells (even after doing this a few times, there are still some cells in the wells
3. Transfer cells to a cryovial tube and centrifuge in a tabletop centrifuge at 3000 RPM for 5 minutes
4. Discard supernatant and
   a. Option 1: slowly resuspend cells using 1 ml of freezing media
   b. Option 2: resuspend cells in 900 μl of FBS or Medium E and then slowly add 100 μl of DMSO
5. Place in a Mr. Frosty and put in the −80° C. freezer for at least 100 minutes (1 degree cooling per minute)
6. Store in liquid nitrogen (x) Isolation of Peripheral Blood Mononuclear Cells from Human Blood Materials
1. Na heparin green top blood collection tubes (BD Vacutainer 367874)
2. Serum red top blood collection tubes with clot activator (BD Vacutainer 367820)
3. 1× Sterile D-PBS (cellgro, 21-031-CM)
4. 50 ml conical tubes (Falcon, 352070)
5. Ficoll 1077 (Sigma 10771, Histopaque-1077)
6. Medium A (Stemcell Technologies, 03801)
7. Trypan blue (Gibco 15250-061)
8. DMSO (Sigma D2650)
9. Sarstedt cryovial tubes (Sarstedt 72.694.996)
10. Mr. Frosty controlled freezing chambers Protocol
1. Obtain peripheral blood from the subject by venipuncture. Have blood drawn into a Na heparin green top tube. If desired, have another aliquot drawn into a red top tube in order to freeze away an aliquot of subject sera (you may also save subject plasma in step 6). The approximate yield of peripheral blood mononuclear cells (PBMCs) is 1-2E6 cells/ml of peripheral blood
2. Add 15 ml of warmed 1×D-PBS to a 50 ml conical tube. One conical tube is needed for every 10 ml of blood drawn
3. Add 10 ml of blood to each 50 ml conical tube containing 1×D-PBS
4. Underlay the 25 ml of blood and D-PBS with 14 ml of warmed Ficoll
5. Centrifuge in a swinging bucket centrifuge for 25 minutes at 2500 RPM, with the brake and acceleration set to zero, or as low as possible
6. Remove and discard most of the plasma on top, down to about 2-3 mm from the buffy layer. Save 1 ml for testing, if desired (freeze plasma at −80° C.). Alternatively, blood can be collected into a red top tube
7. Remove buffy coat by tilting tube and removing cells until middle of liquid in tube starts to clear then pipette the material into a new 50 ml conical tube. Be sure to move the pipette around the sides of the tube in order to collect all PBMCs.
8. Add up to 50 ml of warmed Medium A to tube containing buffy coat layers
9. Centrifuge at 1800 rpm for 18 min in a swinging bucket centrifuge
10. Remove supernatant and resuspend cells in 2 ml of warmed Medium A for every initial 10 ml of blood
11. Add 10 µl of cells to 390 µl of trypan blue and count 2 quadrants
12. When continuing on to perform B cell cultures from the PBMCs without freezing see the B-cells from subject PBMCs protocol
13. For freezing PBMCs, resuspend cells at 5-10E6 cells per 900 µl in Medium A, then add 1/10 final volume of DMSO
14. Freeze PBMCs in 1 ml aliquots in Cryovial tubes.
15. Place tubes in a Mr. Frosty freezing chamber and put in the −80° C. freezer for at least 100 minutes (1 degree cooling per minute)
16. Move samples to liquid nitrogen for storage (xi) Standard Human IgE Fluorescent ELISA Materials
1. Capture antibodies:
   Omalizumab (Xolair); 2.0 mg/ml
2. Secondary antibody
   Mouse anti-human IgE FC-HRP; Clone B3102E8-HRP; Southern Biotech; Cat No: 9160-05
3. Carbonate buffer
   Dissolve the following in 1 L of distilled water:
      i. 1.59 g $Na_2CO_3$
      ii. 2.93 g NaHCO
      iii. Adjust pH to 9.6
      iv. Filter solution at 0.22 µm
      v. Store at room temperature
4. 384 well; black, w/o lid; non-treated, non-sterile; Thermo Scientific No. 262260
5. ELx405 Plate Washer (Biotek)
6. Matrix Pipette (Thermo)
7. 64-channel multipipette (CappAero C10-64) or standard 12 channel pipette
8. QuantaBlu Fluorogenic Peroxidase Substrate Kits; Thermo Prod #15169
   QuantaBlu Substrate Solution, 250 ml
   QuantaBlu Stable Peroxide Solution, 30 ml
   QuantaBlu Stable Stop Solution, 275 ml
9. PBS 10× Molecular Biology Grade; Cellgro REF 46-013CM
10. Block (1 L)
    100 ml of 10×PBS Molecular Biology Grade (Cellgro REF 46-013-CM)
    12-15 g of powdered milk (Great Value Instant Nonfat Dry Milk from Walmart)
    20 ml goat serum (Gibco 16210-072)
    Fill up to 1 L with $dH_2O$
    Add 500 µl of Tween 20 (Sigma P7949)
    Store at 4° C.
11. 1× Wash buffer (1 L)
    100 ml of 10×PBS Molecular Biology Grade (Cellgro REF 46-013-CM)
    1 ml of Tween 20 (Sigma P7949)
    900 ml water
    Store at room temperature
12. Medium A (Stemcell Technologies, 03801)
13. Molecular Devices Spectramax M3 (or equivalent fluorescence plate reader)

Protocol
1. Dilute capture antibody in carbonate buffer for the number of plates you want to coat (make 10.5 ml per plate; there will be extra).
   a. Omalizumab (2 mg/ml); 1:1000
2. Coat plates overnight at 4° C.:
   a. Use 25 µl/well for a 384-well plate (10.5 ml)
   b. Note: If you forget to coat plates overnight, you can coat plates the same day at 37° C. for 3 hours
3. Wash each plate(s) 5 times with 1× wash buffer (or water) by running program 8 (384-5) on the 405.
   a. Alternatively, you can simply dump the contents into the sink and tap the surface of the ELISA plate on paper towels
4. Fill all wells with block:
   a. Use 115 µl/well for a 384-well plate (49 ml)
   b. Incubate at room temperature for at least 1 hour
      i. Don't shortcut this step
      ii. Block entire plate even if you aren't using every well
      iii. Start block first thing in the morning after the wash step
   c. Wash each plate(s) 5 times with 1× wash buffer (or water) by running program 8 (384-5) on the 405.
   d. Add block to all wells:
      i. Use 25 µl/well for a 384 well plate (10.5 ml)
5. Transfer 25 to 75 µl of rh-IL-21, CD40L, BAFF-NIH3T3 B-cell or hybridoma supernatant using a 12 channel pipette (if source pate is 96-well) or 64-channel multipipette (if source plate is 384-well)
   a. Perform this step in the laminar flow hood.
   b. Be careful not to suck up the rh-IL-21, CD40L, BAFF-NIH3T3 or B-cells using the pipette (don't pull supernatant when in contact with the bottom of the well)
6. Incubate plates for at least 30 minutes and up to one hour
   a. Always be sure to incubate the supernatants longer than the incubation time used for the secondary antibody
7. Wash each plate(s) 5 times with 1× wash buffer (or water) by running program 8 (384-5) on the 405.
8. Dilute the secondary antibody in block solution:
   a. Mouse anti-human IgE FC-HRP; Clone B3102E8-HRP
      i. Use 1:1000 dilution in block (1 µg/ml final)
      ii. Add 25 µl/well for 384 well plate (10.5 ml)
      iii. Add 100 µl/well for 96 well plate (10.5 ml)
   b. Incubate for 30 minutes at room temperature
      i. Note: Secondary antibodies conjugated to HRP are extremely difficult to get rid of
         1. Discard reservoir and tips that have come into contact with 2° HRP
9. Wash each plate(s) 7 times with 1× wash buffer by running program 9 (384-7) on the 405. Flip plate to opposite orientation and repeat for another 7 washes with 1× wash buffer.
10. Prepare fresh QuantaBlu Working Solution (WS) (WS is stable for 24 hrs at room temperature)
    a. Mix 9 parts of QuantaBlu Substrate Solution to 1 part of QuantaBlue Stable Peroxide Solution. Note: To reduce variability, equilibrate WS to RT before adding to the wells
    b. Prepare 10.5 ml of WS per plate:
       i. Add 9.45 ml QuantaBlu Substrate
       ii. Add 1.05 ml of QuantaBlu Stable Peroxide Solution 11. Add QuantaBlu Working Solution (WS) to each well and incubate at room temperature for 20-30 minutes
    a. Add 25 µl/well for 384 well plate (10.5 ml)
    b. Add 100 µl/well for 96 well plate (10.5 ml)
12. Stop peroxidase activity by adding 50 µl of QuantaBlu Stop Solution to each well
    a. Add 25 µl/well for 384 well plate (10.5 ml)
    b. Add 100 µl/well for 96 well plate (10.5 ml)
13. Measure relative fluorescence units (RFU) of each well with Molecular Devices Spectramax M3 (or equivalent fluorescence plate reader)
    a. The excitation and emission maxima for QuantaBlu Substrate are 325 nm and 420 nm respectively.
    b. Select Corning 384 well plate black as plate type
14. Transfer positive wells from the original culture plate to:
    a. If you were screening rh-IL-21, CD40L, BAFF-NIH3T3 activated B-cells, gently resuspend the positives cells and transfer each hit to microcentrifuge tube to prepare for cytofusion (see B-cell/HMMA fusion protocol)
    b. If you were screening hybridomas, transfer each hit to the next biggest well or flask containing Medium E (the order is 384-well plates to 48-well plates to 12-well plates to a T-75 flask to a T-225 flask)

D. Engineering of Antibody Sequences

In various embodiments, one may choose to engineer sequences of the identified antibodies for a variety of reasons, such as improved expression, improved cross-reactivity or diminished off-target binding. Modified antibodies may be made by any technique known to those of skill in the art, including expression through standard molecular biological techniques, or the chemical synthesis of polypeptides. Methods for recombinant expression are addressed elsewhere in this document. The following is a general discussion of relevant goals techniques for antibody engineering.

Hybridomas may be cultured, then cells lysed, and total RNA extracted. Random hexamers may be used with RT to generate cDNA copies of RNA, and then PCR performed using a multiplex mixture of PCR primers expected to amplify all human variable gene sequences. PCR product can be cloned into pGEM-T Easy vector, then sequenced by automated DNA sequencing using standard vector primers. Assay of binding and neutralization may be performed using antibodies collected from hybridoma supernatants and purified by FPLC, using Protein G columns.

Recombinant full-length antibodies can be generated by subcloning heavy and light chain Fv DNAs from the cloning vector into an IgE plasmid vector, transfected into 293 (e.g., Freestyle) cells or CHO cells, and antibodies can be collected and purified from the 293 or CHO cell supernatant. Other appropriate host cells systems include bacteria, such as E. coli, insect cells (S2, Sf9, Sf29, High Five), plant cells (e.g., tobacco, with or without engineering for human-like glycans), algae, or in a variety of non-human transgenic contexts, such as mice, rats, goats or cows.

Expression of nucleic acids encoding antibodies, both for the purpose of subsequent antibody purification, and for immunization of a host, is also contemplated. Antibody coding sequences can be RNA, such as native RNA or modified RNA. Modified RNA contemplates certain chemical modifications that confer increased stability and low immunogenicity to mRNAs, thereby facilitating expression of therapeutically important proteins. For instance, N1-methyl-pseudouridine (N1mΨ) outperforms several other nucleoside modifications and their combinations in terms of translation capacity. In addition to turning off the immune/eIF2α phosphorylation-dependent inhibition of translation, incorporated N1mΨ nucleotides dramatically alter the dynamics of the translation process by increasing ribosome pausing and density on the mRNA. Increased ribosome loading of modified mRNAs renders them more permissive for initiation by favoring either ribosome recycling on the same mRNA or de novo ribosome recruitment. Such modifications could be used to enhance antibody expression in vivo following inoculation with RNA. The RNA, whether native or modified, may be delivered as naked RNA or in a delivery vehicle, such as a lipid nanoparticle.

Alternatively, DNA encoding the antibody may be employed for the same purposes. The DNA is included in an expression cassette comprising a promoter active in the host cell for which it is designed. The expression cassette is advantageously included in a replicable vector, such as a conventional plasmid or minivector. Vectors include viral vectors, such as poxviruses, adenoviruses, herpesviruses, adeno-associated viruses, and lentiviruses are contemplated. Replicons encoding antibody genes such as alphavirus replicons based on VEE virus or Sindbis virus are also contemplated. Delivery of such vectors can be performed by needle through intramuscular, subcutaneous, or intradermal routes, or by transcutaneous electroporation when in vivo expression is desired.

The rapid availability of antibody produced in the same host cell and cell culture process as the final cGMP manufacturing process has the potential to reduce the duration of process development programs. Lonza has developed a generic method using pooled transfectants grown in CDACF medium, for the rapid production of small quantities (up to 50 g) of antibodies in CHO cells. Although slightly slower than a true transient system, the advantages include a higher product concentration and use of the same host and process as the production cell line. Example of growth and productivity of GS-CHO pools, expressing a model antibody, in a disposable bioreactor: in a disposable bag bioreactor culture (5 L working volume) operated in fed-batch mode, a harvest antibody concentration of 2 g/L was achieved within 9 weeks of transfection.

Antibody molecules will comprise fragments (such as F(ab'), F(ab')$_2$) that are produced, for example, by the proteolytic cleavage of the mAbs, or single-chain immunoglobulins producible, for example, via recombinant means. F(ab') antibody derivatives are monovalent, while F(ab')$_2$ antibody derivatives are bivalent. In one embodiment, such fragments can be combined with one another, or with other antibody fragments or receptor ligands to form "chimeric" binding molecules. Significantly, such chimeric molecules may contain substituents capable of binding to different epitopes of the same molecule.

In related embodiments, the antibody is a derivative of the disclosed antibodies, e.g., an antibody comprising the CDR sequences identical to those in the disclosed antibodies (e.g., a chimeric, or CDR-grafted antibody). Alternatively, one may wish to make modifications, such as introducing conservative changes into an antibody molecule. In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. As detailed in U.S. Pat. No. 4,554,101, the following hydrophilicity values have been assigned to amino acid residues: basic amino acids: arginine (+3.0), lysine (+3.0), and histidine (−0.5); acidic amino acids: aspartate (+3.0±1), glutamate (+3.0±1), asparagine (+0.2), and glutamine (+0.2); hydrophilic, nonionic amino acids: serine (+0.3), asparagine (+0.2), glutamine (+0.2), and threonine (−0.4), sulfur containing amino acids: cysteine (−1.0) and methionine (−1.3); hydrophobic, nonaromatic amino acids: valine (−1.5), leucine (−1.8), isoleucine (−1.8), proline (−0.5±1), alanine (−0.5), and glycine (0); hydrophobic, aromatic amino acids: tryptophan (−3.4), phenylalanine (−2.5), and tyrosine (−2.3).

It is understood that an amino acid can be substituted for another having a similar hydrophilicity and produce a biologically or immunologically modified protein. In such changes, the substitution of amino acids whose hydrophilicity values are within ±2 is preferred, those that are within ±1 are particularly preferred, and those within ±0.5 are even more particularly preferred.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known to those of skill in the art and include: arginine and lysine; glutamate and aspartate; serine and threonine; glutamine and asparagine; and valine, leucine and isoleucine.

The present disclosure also contemplates isotype modification. By modifying the Fc region to have a different isotype, different functionalities can be achieved. For example, changing to $IgG_1$ can increase antibody dependent cell cytotoxicity, switching to class A can improve tissue distribution, and switching to class M can improve valency. Modifications in the Fc region can be introduced to extend the in vivo half-life of the antibody, or to alter Fc mediated fucntions such as complement activation, antibody dependent cellular cytotoxicity (ADCC), and FcR-mediated phagocytosis.

Of central importance to the present disclosure is isotype modification involving changing a naturally occurring human IgE isotype variable sequence to an IgG isotype. By making this unnatural modification of the IgE antibody, a pathogenic molecule can be made to possess therapeutic functions. Aside from the theoretical benefit that IgE isotype antibodies may have in control of helminth infections, IgE antibodies are necessary for causing IgE-mediated allergy. The function of an IgE antibody is conveyed through its Fc region, which directs binding of the antibody to specific Fc receptors on various cells. By changing a natural human IgE to an IgG, one completely alters the Fc receptors that can be engaged—this has never been shown to occur naturally in humans since the IgG isotypes are deleted from the B cell DNA when it class-switched to IgE. It is the IgE antibody's ability to bind the Fc receptors, FcεRI and FcεRII, which endow its pathogenic function. By engineering a human IgE variable sequence into an IgG antibody isotype, the pathogenic molecule can no longer perform its harmful functions. Additionally, the engineered IgG antibody can then provide new, therapeutic functions through engagement with various Fcγ receptors, such as those found on the mast cell, including FcγRIIB IgG antibodies that bind FcγRIIB on the surface of mast cells result in inhibitory signaling and inhibition of mediator release. For example, an allergen specific IgE antibody bound to FcεRI on mast cells will signal the release of inflammatory mediators upon binding its specific allergen—resulting in the diseases associated with allergy. However, an IgG made from the allergen-specific IgE variable sequences would bind FcγRIIB on mast cells and inhibit mediator release upon binding the specific disease inciting allergen.

Altered Glycosylation.

A particular embodiment of the present disclosure is an isolated monoclonal antibody, or antigen binding fragment thereof, containing a substantially homogeneous glycan without sialic acid, galactose, or fucose. The monoclonal antibody comprises a heavy chain variable region and a light chain variable region, both of which may be attached to heavy chain or light chain constant regions respectively. The aforementioned substantially homogeneous glycan may be covalently attached to the heavy chain constant region.

Another embodiment of the present disclosure comprises a mAb with a novel Fc glycosylation pattern. The isolated monoclonal antibody, or antigen binding fragment thereof, is present in a substantially homogenous composition represented by the GNGN or G1/G2 glycoform. Fc glycosylation plays a significant role in anti-viral and anti-cancer properties of therapeutic mAbs. The disclosure is in line with a recent study that shows increased anti-lentivirus cell-mediated viral inhibition of a fucose free anti-HIV mAb in vitro. This embodiment of the present disclosure with homogenous glycans lacking a core fucose, showed increased protection against specific viruses by a factor greater than two-fold. Elimination of core fucose dramatically improves the ADCC activity of mAbs mediated by natural killer (NK) cells but appears to have the opposite effect on the ADCC activity of polymorphonuclear cells (PMNs).

The isolated monoclonal antibody, or antigen binding fragment thereof, comprising a substantially homogenous composition represented by the GNGN or G1/G2 glycoform exhibits increased binding affinity for Fc gamma RI and Fc gamma RIII compared to the same antibody without the substantially homogeneous GNGN glycoform and with G0, G1F, G2F, GNF, GNGNF or GNGNFX containing glycoforms. In one embodiment of the present disclosure, the antibody dissociates from Fc gamma RI with a Kd of $1 \times 10^{-8}$ M or less and from Fc gamma RIII with a Kd of $1 \times 10^{-7}$ M or less.

Glycosylation of an Fc region is typically either N-linked or O-linked. N-linked refers to the attachment of the carbohydrate moiety to the side chain of an asparagine residue. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern may be altered, for example, by deleting one or more glycosylation site(s) found in the polypeptide, and/or adding one or more glycosylation site(s) that are not present in the polypeptide. Addition of glycosylation sites to the Fc region of an antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration may also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the antibody is expressed in cells that express beta (1,4)-N-acetylglucosaminyltransferase III (GnT III), such that GnT III adds GlcNAc to the IL-23p19 antibody. Methods for producing antibodies in such a fashion are provided in WO/9954342, WO/03011878, patent publication 20030003097A1, and Umana et al., Nature Biotechnology, 17:176-180, February 1999. Cell lines can be altered to enhance or reduce or eliminate certain post-translational modifications, such as glycosylation, using genome editing technology such as Clustered Regularly Interspaced Short Palindromic Repeats (CRISPR). For example, CRISPR technology can be used to eliminate genes encoding glycosylating enzymes in 293 or CHO cells used to express recombinant monoclonal antibodies.

Elimination of Monoclonal Antibody Protein Sequence Liabilities.

It is possible to engineer the antibody variable gene sequences obtained from human B cells to enhance their manufacturability and safety. Potential protein sequence liabilities can be identified by searching for sequence motifs associated with sites containing:

1) Unpaired Cys residues,
2) N-linked glycosylation,
3) Asn deamidation,
4) Asp isomerization,
5) SYE truncation,
6) Met oxidation,
7) Trp oxidation,
8) N-terminal glutamate,
9) Integrin binding,
10) CD11c/CD18 binding, or
11) Fragmentation Such motifs can be eliminated by altering the synthetic gene for the cDNA encoding recombinant antibodies.

Protein engineering efforts in the field of development of therapeutic antibodies clearly reveal that certain sequences or residues are associated with solubility differences (Fernandez-Escamilla et al., *Nature Biotech.*, 22 (10), 1302-1306, 2004; Chennamsetty et al., *PNAS*, 106 (29), 11937-11942, 2009; Voynov et al., *Biocon. Chem.*, 21 (2), 385-392, 2010) Evidence from solubility-altering mutations in the literature indicate that some hydrophilic residues such as aspartic acid, glutamic acid, and serine contribute significantly more favorably to protein solubility than other hydrophilic residues, such as asparagine, glutamine, threonine, lysine, and arginine.

Stability.

Antibodies can be engineered for enhanced biophysical properties. One can use elevated temperature to unfold antibodies to determine relative stability, using average apparent melting temperatures. Differential Scanning calorimetry (DSC) measures the heat capacity, $C_p$, of a molecule (the heat required to warm it, per degree) as a function of temperature. One can use DSC to study the thermal stability of antibodies. DSC data for mAbs is particularly interesting because it sometimes resolves the unfolding of individual domains within the mAb structure, producing up to three peaks in the thermogram (from unfolding of the Fab, $C_H2$, and $C_H3$ domains). Typically unfolding of the Fab domain produces the strongest peak. The DSC profiles and relative stability of the Fc portion show characteristic differences for the human $IgG_1$, $IgG_2$, $IgG_3$, and $IgG_4$ subclasses (Garber and Demarest, *Biochem. Biophys. Res. Commun.* 355, 751-757, 2007). One also can determine average apparent melting temperature using circular dichroism (CD), performed with a CD spectrometer. Far-UV CD spectra will be measured for antibodies in the range of 200 to 260 nm at increments of 0.5 nm. The final spectra can be determined as averages of 20 accumulations. Residue ellipticity values can be calculated after background subtraction. Thermal unfolding of antibodies (0.1 mg/mL) can be monitored at 235 nm from 25-95° C. and a heating rate of 1° C./min. One can use dynamic light scattering (DLS) to assess for propensity for aggregation. DLS is used to characterize size of various particles including proteins. If the system is not disperse in size, the mean effective diameter of the particles can be determined. This measurement depends on the size of the particle core, the size of surface structures, and particle concentration. Since DLS essentially measures fluctuations in scattered light intensity due to particles, the diffusion coefficient of the particles can be determined. DLS software in commercial DLA instruments displays the particle population at different diameters. Stability studies can be done conveniently using DLS. DLS measurements of a sample can show whether the particles aggregate over time or with temperature variation by determining whether the hydrodynamic radius of the particle increases. If particles aggregate, one can see a larger population of particles with a larger radius. Stability depending on temperature can be analyzed by controlling the temperature in situ. Capillary electrophoresis (CE) techniques include proven methodologies for determining features of antibody stability. One can use an iCE approach to resolve antibody protein charge variants due to deamidation, C-terminal lysines, sialylation, oxidation, glycosylation, and any other change to the protein that can result in a change in pI of the protein. Each of the expressed antibody proteins can be evaluated by high throughput, free solution isoelectric focusing (IEF) in a capillary column (cIEF), using a Protein Simple Maurice instrument. Whole-column UV absorption detection can be performed every 30 seconds for real time monitoring of molecules focusing at the isoelectric points (pIs). This approach combines the high resolution of traditional gel IEF with the advantages of quantitation and automation found in column-based separations while eliminating the need for a mobilization step. The technique yields reproducible, quantitative analysis of identity, purity, and heterogeneity profiles for the expressed antibodies. The results identify charge heterogeneity and molecular sizing on the antibodies, with both absorbance and native fluorescence detection modes and with sensitivity of detection down to 0.7 µg/mL.

Solubility.

One can determine the intrinsic solubility score of antibody sequences. The intrinsic solubility scores can be calculated using CamSol Intrinsic (Sormanni et al., *J Mol Biol* 427, 478-490, 2015). The amino acid sequences for residues 95-102 (Kabat numbering) in HCDR3 of each antibody fragment such as a scFv can be evaluated via the online program to calculate the solubility scores. One also can determine solubility using laboratory techniques. Various techniques exist, including addition of lyophilized protein to a solution until the solution becomes saturated and the solubility limit is reached, or concentration by ultrafiltration in a microconcentrator with a suitable molecular weight cut-off. The most straightforward method is induction of amorphous precipitation, which measures protein solubility using a method involving protein precipitation using ammonium sulfate (Trevino et al., *J Mol Biol*, 366: 449-460, 2007). Ammonium sulfate precipitation gives quick and accurate information on relative solubility values. Ammonium sulfate precipitation produces precipitated solutions with well-defined aqueous and solid phases and requires relatively small amounts of protein. Solubility measurements performed using induction of amorphous precipitation by ammonium sulfate also can be done easily at different pH values. Protein solubility is highly pH dependent, and pH is considered the most important extrinsic factor that affects solubility.

Autoreactivity.

Generally, it is thought that autoreactive clones should be eliminated during ontogeny by negative selection, however it has become clear that many human naturally occurring antibodies with autoreactive properties persist in adult mature repertoires, and the autoreactivity may enhance the antiviral function of many antibodies to pathogens. It has been noted that HCDR3 loops in antibodies during early B cell development are often rich in positive charge and exhibit autoreactive patterns (Wardemann et al., *Science* 301, 1374-1377, 2003). One can test a given antibody for autoreactivity by assessing the level of binding to human origin cells in microscopy (using adherent HeLa or HEp-2 epithelial cells) and flow cytometric cell surface staining (using suspension Jurkat T cells and 293 S human embryonic kidney cells). Autoreactivity also can be surveyed using assessment of binding to tissues in tissue arrays.

Preferred Residues ("Human Likeness").

B cell repertoire deep sequencing of human B cells from blood donors is being performed on a wide scale in many recent studies. Sequence information about a significant portion of the human antibody repertoire facilitates statistical assessment of antibody sequence features common in healthy humans. With knowledge about the antibody sequence features in a human recombined antibody variable gene reference database, the position specific degree of "Human Likeness" (HL) of an antibody sequence can be estimated. HL has been shown to be useful for the development of antibodies in clinical use, like therapeutic antibodies or antibodies as vaccines. The goal is to increase the human likeness of antibodies to reduce potential adverse effects and anti-antibody immune responses that will lead to significantly decreased efficacy of the antibody drug or can induce serious health implications. One can assess antibody characteristics of the combined antibody repertoire of three healthy human blood donors of about 400 million sequences in total and created a novel "relative Human Likeness" (rHL) score that focuses on the hypervariable region of the antibody. The rHL score allows one to easily distinguish between human (positive score) and non-human sequences (negative score). Antibodies can be engineered to eliminate residues that are not common in human repertoires.

E. Single Chain Antibodies

A single chain variable fragment (scFv) is a fusion of the variable regions of the heavy and light chains of immunoglobulins, linked together with a short (usually serine, glycine) linker. This chimeric molecule retains the specificity of the original immunoglobulin, despite removal of the constant regions and the introduction of a linker peptide. This modification usually leaves the specificity unaltered. These molecules were created historically to facilitate phage display where it is highly convenient to express the antigen binding domain as a single peptide. Alternatively, scFv can be created directly from subcloned heavy and light chains derived from a hybridoma or B cell. Single chain variable fragments lack the constant Fc region found in complete antibody molecules, and thus, the common binding sites (e.g., protein A/G) used to purify antibodies. These fragments can often be purified/immobilized using Protein L since Protein L interacts with the variable region of kappa light chains.

Flexible linkers generally are comprised of helix- and turn-promoting amino acid residues such as alanine, serine and glycine. However, other residues can function as well. Tang et al. (1996) used phage display as a means of rapidly selecting tailored linkers for single-chain antibodies (scFvs) from protein linker libraries. A random linker library was constructed in which the genes for the heavy and light chain variable domains were linked by a segment encoding an 18-amino acid polypeptide of variable composition. The scFv repertoire (approx. $5 \times 10^6$ different members) was displayed on filamentous phage and subjected to affinity selection with hapten. The population of selected variants exhibited significant increases in binding activity but retained considerable sequence diversity. Screening 1054 individual variants subsequently yielded a catalytically active scFv that was produced efficiently in soluble form. Sequence analysis revealed a conserved proline in the linker two residues after the $V_H$ C terminus and an abundance of arginines and prolines at other positions as the only common features of the selected tethers.

The recombinant antibodies of the present disclosure may also involve sequences or moieties that permit dimerization or multimerization of the receptors. Such sequences include those derived from IgA, which permit formation of multimers in conjunction with the J-chain. Another multimerization domain is the Gal4 dimerization domain. In other embodiments, the chains may be modified with agents such as biotin/avidin, which permit the combination of two antibodies.

In a separate embodiment, a single-chain antibody can be created by joining receptor light and heavy chains using a non-peptide linker or chemical unit. Generally, the light and heavy chains will be produced in distinct cells, purified, and subsequently linked together in an appropriate fashion (i.e., the N-terminus of the heavy chain being attached to the C-terminus of the light chain via an appropriate chemical bridge).

Cross-linking reagents are used to form molecular bridges that tie functional groups of two different molecules, e.g., a stabilizing and coagulating agent. However, it is contemplated that dimers or multimers of the same analog or heteromeric complexes comprised of different analogs can be created. To link two different compounds in a step-wise manner, hetero-bifunctional cross-linkers can be used that eliminate unwanted homopolymer formation.

An exemplary hetero-bifunctional cross-linker contains two reactive groups: one reacting with primary amine group (e.g., N-hydroxy succinimide) and the other reacting with a thiol group (e.g., pyridyl disulfide, maleimides, halogens, etc.). Through the primary amine reactive group, the cross-linker may react with the lysine residue(s) of one protein (e.g., the selected antibody or fragment) and through the thiol reactive group, the cross-linker, already tied up to the first protein, reacts with the cysteine residue (free sulfhydryl group) of the other protein (e.g., the selective agent).

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo, preventing release of the targeting peptide prior to reaching the site of action. These linkers are thus one group of linking agents.

Another cross-linking reagent is SMPT, which is a bifunctional cross-linker containing a disulfide bond that is "sterically hindered" by an adjacent benzene ring and methyl groups. It is believed that steric hindrance of the disulfide bond serves a function of protecting the bond from attack by thiolate anions such as glutathione which can be present in tissues and blood, and thereby help in preventing decoupling of the conjugate prior to the delivery of the attached agent to the target site.

The SMPT cross-linking reagent, as with many other known cross-linking reagents, lends the ability to cross-link functional groups such as the SH of cysteine or primary amines (e.g., the epsilon amino group of lysine). Another possible type of cross-linker includes the hetero-bifunctional photoreactive phenylazides containing a cleavable disulfide bond such as sulfosuccinimidyl-2-(p-azido salicylamido) ethyl-1,3'-dithiopropionate. The N-hydroxy-succinimidyl group reacts with primary amino groups and the phenylazide (upon photolysis) reacts non-selectively with any amino acid residue.

In addition to hindered cross-linkers, non-hindered linkers also can be employed in accordance herewith. Other useful cross-linkers, not considered to contain or generate a protected disulfide, include SATA, SPDP and 2-iminothiolane (Wawrzynczak & Thorpe, 1987). The use of such cross-linkers is well understood in the art. Another embodiment involves the use of flexible linkers.

U.S. Pat. No. 4,680,338, describes bifunctional linkers useful for producing conjugates of ligands with amine-containing polymers and/or proteins, especially for forming antibody conjugates with chelators, drugs, enzymes, detectable labels and the like. U.S. Pat. Nos. 5,141,648 and 5,563,250 disclose cleavable conjugates containing a labile bond that is cleavable under a variety of mild conditions. This linker is particularly useful in that the agent of interest may be bonded directly to the linker, with cleavage resulting in release of the active agent. Particular uses include adding a free amino or free sulfhydryl group to a protein, such as an antibody, or a drug.

U.S. Pat. No. 5,856,456 provides peptide linkers for use in connecting polypeptide constituents to make fusion proteins, e.g., single chain antibodies. The linker is up to about 50 amino acids in length, contains at least one occurrence of a charged amino acid (preferably arginine or lysine) followed by a proline, and is characterized by greater stability and reduced aggregation. U.S. Pat. No. 5,880,270 discloses aminooxy-containing linkers useful in a variety of immunodiagnostic and separative techniques.

F. Multispecific Antibodies

In certain embodiments, antibodies of the present disclosure are bispecific or multispecific. Bispecific antibodies are antibodies that have binding specificities for at least two different epitopes. Exemplary bispecific antibodies may bind to two different epitopes of a single antigen. Other such antibodies may combine a first antigen binding site with a binding site for a second antigen. Alternatively, an anti-pathogen arm may be combined with an arm that binds to a triggering molecule on a leukocyte, such as a T-cell receptor molecule (e.g., CD3), or Fc receptors for IgG (FcγR), such as FcγRI (CD64), FcγRII (CD32) and Fc gamma RIII (CD16), so as to focus and localize cellular defense mechanisms to the infected cell. Bispecific antibodies may also be used to localize cytotoxic agents to infected cells. These antibodies possess a pathogen-binding arm and an arm that binds the cytotoxic agent (e.g., saporin, anti-interferon-α, vinca alkaloid, ricin A chain, methotrexate or radioactive isotope hapten). Bispecific antibodies can be prepared as full length antibodies or antibody fragments (e.g., F(ab').sub.2 bispecific antibodies). WO 96/16673 describes a bispecific anti-ErbB2/anti-Fc gamma RIII antibody and U.S. Pat. No. 5,837,234 discloses a bispecific anti-ErbB2/anti-Fc gamma RI antibody. A bispecific anti-ErbB2/Fc alpha antibody is shown in WO98/02463. U.S. Pat. No. 5,821,337 teaches a bispecific anti-ErbB2/anti-CD3 antibody.

Methods for making bispecific antibodies are known in the art. Traditional production of full length bispecific antibodies is based on the co-expression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of ten different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable regions with the desired binding specificities (antibody-antigen combining sites) are fused to immunoglobulin constant domain sequences. Preferably, the fusion is with an Ig heavy chain constant domain, comprising at least part of the hinge, $C_{H2}$, and $C_{H3}$ regions. It is preferred to have the first heavy-chain constant region ($C_{H1}$) containing the site necessary for light chain bonding, present in at least one of the fusions. DNAs encoding the immunoglobulin heavy chain fusions and, if desired, the immunoglobulin light chain, are inserted into separate expression vectors, and are co-transfected into a suitable host cell. This provides for greater flexibility in adjusting the mutual proportions of the three polypeptide fragments in embodiments when unequal ratios of the three polypeptide chains used in the construction provide the optimum yield of the desired bispecific antibody. It is, however, possible to insert the coding sequences for two or all three polypeptide chains into a single expression vector when the expression of at least two polypeptide chains in equal ratios results in high yields or when the ratios have no significant effect on the yield of the desired chain combination.

In a particular embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986).

According to another approach described in U.S. Pat. No. 5,731,168, the interface between a pair of antibody molecules can be engineered to maximize the percentage of heterodimers that are recovered from recombinant cell culture. The preferred interface comprises at least a part of the $C_{H3}$ domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., Science, 229: 81 (1985) describe a procedure wherein intact antibodies are proteolytically cleaved to generate $F(ab')_2$ fragments. These fragments are reduced in the presence of the dithiol complexing agent, sodium arsenite, to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Techniques exist that facilitate the direct recovery of Fab'-SH fragments from *E. coli*, which can be chemically coupled to form bispecific antibodies. Shalaby et al., J. Exp. Med., 175: 217-225 (1992) describe the production of a humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described (Merchant et al., *Nat. Biotechnol*, 16, 677-681 (1998). doi:10.1038/nbt0798-677pmid: 9661204). For example, bispecific antibodies have been produced using leucine zippers (Kostelny et al., J. Immunol., 148(5):1547-1553, 1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA, 90:6444-6448 (1993) has provided an alternative mechanism for making bispecific antibody fragments. The fragments comprise a $V_H$ connected to a $V_L$ by a linker that is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., J. Immunol., 152:5368 (1994).

In a particular embodiment, a bispecific or multispecific antibody may be formed as a DOCK-AND-LOCK™ (DNL™) complex (see, e.g., U.S. Pat. Nos. 7,521,056; 7,527,787; 7,534,866; 7,550,143 and 7,666,400, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie eta., *FEBS Letters*. 2005; 579:3264; Wong and Scott, *Nat. Rev. Mol. Cell Biol.* 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Antibodies with more than two valencies are contemplated. For example, trispecific antibodies can be prepared (Tutt et al., J. Immunol. 147: 60, 1991; Xu et al., *Science*, 358(6359):85-90, 2017). A multivalent antibody may be internalized (and/or catabolized) faster than a bivalent antibody by a cell expressing an antigen to which the antibodies bind. The antibodies of the present disclosure can be multivalent antibodies with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable regions. For instance, the polypeptide chain(s) may comprise VD1-(X1).sub.n-VD2-(X2)$_n$-Fc, wherein VD1 is a first variable region, VD2 is a second variable region, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable region polypeptides. The multivalent antibody herein may, for instance, comprise from about two to about eight light chain variable region polypeptides. The light chain variable region polypeptides contemplated here comprise a light chain variable region and, optionally, further comprise a CL domain.

Charge modifications are particularly useful in the context of a multispecific antibody, where amino acid substitutions in Fab molecules result in reducing the mispairing of light chains with non-matching heavy chains (Bence-Jones-type side products), which can occur in the production of Fab-based bi-/multispecific antigen binding molecules with a VH/VL exchange in one (or more, in case of molecules comprising more than two antigen-binding Fab molecules) of their binding arms (see also PCT publication no. WO 2015/150447, particularly the examples therein, incorporated herein by reference in its entirety).

Accordingly, in particular embodiments, an antibody comprised in the therapeutic agent comprises
  (a) a first Fab molecule which specifically binds to a first antigen
  (b) a second Fab molecule which specifically binds to a second antigen, and wherein the variable domains VL and VH of the Fab light chain and the Fab heavy chain are replaced by each other,
  wherein the first antigen is an activating T cell antigen and the second antigen is a target cell antigen, or the first antigen is a target cell antigen and the second antigen is an activating T cell antigen; and
  wherein
    i) in the constant domain CL of the first Fab molecule under a) the amino acid at position 124 is substituted by a positively charged amino acid (numbering according to Kabat), and wherein in the constant domain CH1 of the first Fab molecule under a) the amino acid at position 147 or the amino acid at position 213 is substituted by a negatively charged amino acid (numbering according to Kabat EU index); or
    ii) in the constant domain CL of the second Fab molecule under b) the amino acid at position 124 is substituted by a positively charged amino acid (numbering according to Kabat), and wherein in the constant domain CH1 of the second Fab molecule under b) the amino acid at position 147 or the amino acid at position 213 is substituted by a negatively charged amino acid (numbering according to Kabat EU index).

The antibody may not comprise both modifications mentioned under i) and ii). The constant domains CL and CH1 of the second Fab molecule are not replaced by each other (i.e., remain unexchanged).

In another embodiment of the antibody, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 or the amino acid at position 213 is substituted independently by glutamic acid (E), or aspartic acid (D) (numbering according to Kabat EU index).

In a further embodiment, in the constant domain CL of the first Fab molecule under a) the amino acid at position 124 is substituted independently by lysine (K), arginine (R) or histidine (H) (numbering according to Kabat), and in the constant domain CH1 of the first Fab molecule under a) the amino acid at position 147 is substituted independently by glutamic acid (E), or aspartic acid (D) (numbering according to Kabat EU index).

In a particular embodiment, in the constant domain CL of the first Fab molecule under a) the amino acid at position 124 is substituted independently by lysine (K), arginine (R) or histidine (H) (numbering according to Kabat) (in one preferred embodiment independently by lysine (K) or arginine (R)) and the amino acid at position 123 is substituted independently by lysine (K), arginine (R) or histidine (H) (numbering according to Kabat) (in one preferred embodiment independently by lysine (K) or arginine (R)), and in the constant domain CH1 of the first Fab molecule under a) the amino acid at position 147 is substituted independently by glutamic acid (E), or aspartic acid (D) (numbering according to Kabat EU index) and the amino acid at position 213 is substituted independently by glutamic acid (E), or aspartic acid (D) (numbering according to Kabat EU index).

In a more particular embodiment, in the constant domain CL of the first Fab molecule under a) the amino acid at position 124 is substituted by lysine (K) (numbering according to Kabat) and the amino acid at position 123 is substituted by lysine (K) or arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

In an even more particular embodiment, in the constant domain CL of the first Fab molecule under a) the amino acid at position 124 is substituted by lysine (K) (numbering according to Kabat) and the amino acid at position 123 is substituted by arginine (R) (numbering according to Kabat), and in the constant domain CH1 of the first Fab molecule under a) the amino acid at position 147 is substituted by glutamic acid (E) (numbering according to Kabat EU index) and the amino acid at position 213 is substituted by glutamic acid (E) (numbering according to Kabat EU index).

G. Chimeric Antigen Receptors

Artificial T cell receptors (also known as chimeric T cell receptors, chimeric immunoreceptors, chimeric antigen receptors (CARs)) are engineered receptors, which graft an arbitrary specificity onto an immune effector cell. Typically, these receptors are used to graft the specificity of a monoclonal antibody onto a T cell, with transfer of their coding sequence facilitated by retroviral vectors. In this way, a large number of target-specific T cells can be generated for adoptive cell transfer. Phase I clinical studies of this approach show efficacy.

The most common form of these molecules are fusions of single-chain variable fragments (scFv) derived from monoclonal antibodies, fused to CD3-zeta transmembrane and endodomain. Such molecules result in the transmission of a zeta signal in response to recognition by the scFv of its target. An example of such a construct is 14g2a-Zeta, which is a fusion of a scFv derived from hybridoma 14g2a (which recognizes disialoganglioside GD2). When T cells express this molecule (usually achieved by oncoretroviral vector transduction), they recognize and kill target cells that express GD2 (e.g., neuroblastoma cells). To target malignant B cells, investigators have redirected the specificity of T cells using a chimeric immunoreceptor specific for the B-lineage molecule, CD19.

The variable portions of an immunoglobulin heavy and light chain are fused by a flexible linker to form a scFv. This scFv is preceded by a signal peptide to direct the nascent protein to the endoplasmic reticulum and subsequent surface expression (this is cleaved). A flexible spacer allows to the scFv to orient in different directions to enable antigen binding. The transmembrane domain is a typical hydrophobic alpha helix usually derived from the original molecule of the signaling endodomain which protrudes into the cell and transmits the desired signal.

Type I proteins are in fact two protein domains linked by a transmembrane alpha helix in between. The cell membrane lipid bilayer, through which the transmembrane domain passes, acts to isolate the inside portion (endodomain) from the external portion (ectodomain). It is not so surprising that attaching an ectodomain from one protein to an endodomain of another protein results in a molecule that combines the recognition of the former to the signal of the latter.

Ectodomain.

A signal peptide directs the nascent protein into the endoplasmic reticulum. This is essential if the receptor is to be glycosylated and anchored in the cell membrane. Any eukaryotic signal peptide sequence usually works fine. Generally, the signal peptide natively attached to the amino-terminal most component is used (e.g., in a scFv with orientation light chain-linker-heavy chain, the native signal of the light-chain is used The antigen recognition domain is usually an scFv. There are however many alternatives. An antigen recognition domain from native T-cell receptor (TCR) alpha and beta single chains have been described, as have simple ectodomains (e.g., CD4 ectodomain to recognize HIV infected cells) and more exotic recognition components such as a linked cytokine (which leads to recognition of cells bearing the cytokine receptor). In fact, almost anything that binds a given target with high affinity can be used as an antigen recognition region.

A spacer region links the antigen binding domain to the transmembrane domain. It should be flexible enough to allow the antigen binding domain to orient in different directions to facilitate antigen recognition. The simplest form is the hinge region from $IgG_1$. Alternatives include the $CH_2CH_3$ region of immunoglobulin and portions of CD3. For most scFv based constructs, the IgG1 hinge suffices. However, the best spacer often has to be determined empirically.

Transmembrane Domain.

The transmembrane domain is a hydrophobic alpha helix that spans the membrane. Generally, the transmembrane domain from the most membrane proximal component of the endodomain is used. Interestingly, using the CD3-zeta transmembrane domain may result in incorporation of the artificial TCR into the native TCR a factor that is dependent on the presence of the native CD3-zeta transmembrane charged aspartic acid residue. Different transmembrane domains result in different receptor stability. The CD28 transmembrane domain results in a brightly expressed, stable receptor.

Endodomain.

This is the "business-end" of the receptor. After antigen recognition, receptors cluster and a signal is transmitted to the cell. The most commonly used endodomain component is CD3-zeta which contains 3 ITAMs. This transmits an activation signal to the T cell after antigen is bound. CD3-zeta may not provide a fully competent activation signal and additional co-stimulatory signaling is needed.

"First-generation" CARs typically had the intracellular domain from the CD3 chain, which is the primary transmitter of signals from endogenous TCRs. "Second-generation" CARs add intracellular signaling domains from various costimulatory protein receptors (e.g., CD28, 41BB, ICOS) to the cytoplasmic tail of the CAR to provide additional signals to the T cell. Preclinical studies have indicated that the second generation of CAR designs improves the antitumor activity of T cells. More recent, "third-generation" CARs combine multiple signaling domains, such as CD3z-CD28-41BB or CD3z-CD28-OX40, to further augment potency.

H. ADCs

Antibody Drug Conjugates or ADCs are a new class of highly potent biopharmaceutical drugs designed as a targeted therapy for the treatment of people with infectious disease. ADCs are complex molecules composed of an antibody (a whole mAb or an antibody fragment such as a single-chain variable fragment, or scFv) linked, via a stable chemical linker with labile bonds, to a biological active cytotoxic/anti-viral payload or drug. Antibody Drug Conjugates are examples of bioconjugates and immunoconjugates.

By combining the unique targeting capabilities of monoclonal antibodies with the cancer-killing ability of cytotoxic drugs, antibody-drug conjugates allow sensitive discrimination between healthy and diseased tissue. This means that, in contrast to traditional systemic approaches, antibody-drug conjugates target and attack the infected cell so that healthy cells are less severely affected.

In the development ADC-based anti-tumor therapies, an anticancer drug (e.g., a cell toxin or cytotoxin) is coupled to an antibody that specifically targets a certain cell marker (e.g., a protein that, ideally, is only to be found in or on infected cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cell or impairs fungal replication. Due to this targeting, ideally the drug has lower side effects and gives a wider therapeutic window than other agents.

A stable link between the antibody and cytotoxic/anti-viral agent is a crucial aspect of an ADC. Linkers are based on chemical motifs including disulfides, hydrazones or peptides (cleavable), or thioethers (noncleavable) and control the distribution and delivery of the cytotoxic agent to the target cell. Cleavable and noncleavable types of linkers have been proven to be safe in preclinical and clinical trials. Brentuximab vedotin includes an enzyme-sensitive cleavable linker that delivers the potent and highly toxic antimicrotubule agent Monomethyl auristatin E or MMAE, a synthetic antineoplastic agent, to human specific CD30-positive malignant cells. Because of its high toxicity MMAE, which inhibits cell division by blocking the polymerization of tubulin, cannot be used as a single-agent chemotherapeutic drug. However, the combination of MMAE linked to an anti-CD30 monoclonal antibody (cAC10, a cell membrane protein of the tumor necrosis factor or TNF receptor) proved to be stable in extracellular fluid, cleavable by cathepsin and safe for therapy. Trastuzumab emtansine, the other approved ADC, is a combination of the microtubule-formation inhibitor mertansine (DM-1), a derivative of the Maytansine, and antibody trastuzumab (Herceptin®/Genentech/Roche) attached by a stable, non-cleavable linker. The availability of better and more stable linkers has changed the function of the chemical bond. The type of linker, cleavable or noncleavable, lends specific properties to the cytotoxic (anti-cancer) drug. For example, a non-cleavable linker keeps the drug within the cell. As a result, the entire antibody, linker and cytotoxic agent enter the targeted cancer cell where the antibody is degraded to the level of an amino acid. The resulting complex—amino acid, linker and cytotoxic agent—now becomes the active drug. In contrast, cleavable linkers are catalyzed by enzymes in the host cell where it releases the cytotoxic agent.

Another type of cleavable linker, currently in development, adds an extra molecule between the cytotoxic/anti-viral drug and the cleavage site. This linker technology allows researchers to create ADCs with more flexibility without worrying about changing cleavage kinetics. Researchers are also developing a new method of peptide cleavage based on Edman degradation, a method of sequencing amino acids in a peptide. Future direction in the development of ADCs also include the development of site-specific conjugation (TDCs) to further improve stability and therapeutic index and a emitting immunoconjugates and antibody-conjugated nanoparticles.

I. BiTES

Bi-specific T-cell engagers (BiTEs) are a class of artificial bispecific monoclonal antibodies that are investigated for the use as anti-cancer drugs. They direct a host's immune system, more specifically the T cells' cytotoxic activity, against infected cells. BiTE is a registered trademark of Micromet AG.

BiTEs are fusion proteins consisting of two single-chain variable fragments (scFvs) of different antibodies, or amino acid sequences from four different genes, on a single peptide chain of about 55 kilodaltons. One of the scFvs binds to T cells via the CD3 receptor, and the other to an infected cell via a specific molecule.

Like other bispecific antibodies, and unlike ordinary monoclonal antibodies, BiTEs form a link between T cells and target cells. This causes T cells to exert cytotoxic/anti-viral activity on infected cells by producing proteins like perforin and granzymes, independently of the presence of MHC I or co-stimulatory molecules. These proteins enter infected cells and initiate the cell's apoptosis. This action mimics physiological processes observed during T cell attacks against infected cells.

J. Intrabodies

In a particular embodiment, the antibody is a recombinant antibody that is suitable for action inside of a cell—such antibodies are known as "intrabodies." These antibodies may interfere with target function by a variety of mechanism, such as by altering intracellular protein trafficking, interfering with enzymatic function, and blocking protein-protein or protein-DNA interactions. In many ways, their structures mimic or parallel those of single chain and single domain antibodies, discussed above. Indeed, single-transcript/single-chain is an important feature that permits intracellular expression in a target cell, and also makes protein transit across cell membranes more feasible. However, additional features are required.

The two major issues impacting the implementation of intrabody therapeutic are delivery, including cell/tissue targeting, and stability. With respect to delivery, a variety of approaches have been employed, such as tissue-directed delivery, use of cell-type specific promoters, viral-based delivery and use of cell-permeability/membrane translocating peptides. With respect to the stability, the approach is generally to either screen by brute force, including methods that involve phage display and may include sequence maturation or development of consensus sequences, or more directed modifications such as insertion stabilizing sequences (e.g., Fc regions, chaperone protein sequences, leucine zippers) and disulfide replacement/modification.

An additional feature that intrabodies may require is a signal for intracellular targeting. Vectors that can target intrabodies (or other proteins) to subcellular regions such as the cytoplasm, nucleus, mitochondria and ER have been designed and are commercially available (Invitrogen Corp.; Persic et al., 1997).

By virtue of their ability to enter cells, intrabodies have additional uses that other types of antibodies may not achieve. In the case of the present antibodies, the ability to interact with the MUC1 cytoplasmic domain in a living cell may interfere with functions associated with the MUC1 CD, such as signaling functions (binding to other molecules) or oligomer formation. In particular, it is contemplated that such antibodies can be used to inhibit MUC1 dimer formation.

K. Purification

In certain embodiments, the antibodies of the present disclosure may be purified. The term "purified," as used herein, is intended to refer to a composition, isolatable from other components, wherein the protein is purified to any degree relative to its naturally-obtainable state. A purified protein therefore also refers to a protein, free from the environment in which it may naturally occur. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. Other methods for protein purification include, precipitation with ammonium sulfate, PEG, antibodies and the like or by heat denaturation, followed by centrifugation; gel filtration, reverse phase, hydroxylapatite and affinity chromatography; and combinations of such and other techniques.

In purifying an antibody of the present disclosure, it may be desirable to express the polypeptide in a prokaryotic or eukaryotic expression system and extract the protein using denaturing conditions. The polypeptide may be purified from other cellular components using an affinity column, which binds to a tagged portion of the polypeptide. As is generally known in the art, it is believed that the order of conducting the various purification steps may be changed, or that certain steps may be omitted, and still result in a suitable method for the preparation of a substantially purified protein or peptide.

Commonly, complete antibodies are fractionated utilizing agents (i.e., protein A) that bind the Fc portion of the antibody. Alternatively, antigens may be used to simultaneously purify and select appropriate antibodies. Such methods often utilize the selection agent bound to a support, such as a column, filter or bead. The antibodies are bound to a support, contaminants removed (e.g., washed away), and the antibodies released by applying conditions (salt, heat, etc.).

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. Another method for assessing the purity of a fraction is to calculate the specific activity of the fraction, to compare it to the specific activity of the initial extract, and to thus calculate the degree of purity. The actual units used to represent the amount of activity will, of course, be dependent upon the particular assay technique chosen to follow the purification and whether or not the expressed protein or peptide exhibits a detectable activity.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

III. ACTIVE/PASSIVE IMMUNIZATION AND TREATMENT/PREVENTION OF *ASPERGILLUS* INFECTION

A. Formulation and Administration

The present disclosure provides pharmaceutical compositions comprising anti-*A. fumigatus* antibodies and antigens for generating the same. Such compositions comprise a prophylactically or therapeutically effective amount of an antibody or a fragment thereof, or a peptide immunogen, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a particular carrier when the pharmaceutical composition is administered intravenously. Saline solutions and aqueous dextrose and glycerol solutions can also be employed as liquid carriers, particularly for injectable solutions. Other suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The composition, if desired, can also contain minor amounts of wetting or emulsifying agents, or pH buffering agents. These compositions can take the form of solutions, suspensions, emulsion, tablets, pills, capsules, powders, sustained-release formulations and the like. Oral formulations can include standard carriers such as pharmaceutical grades of mannitol, lactose, starch, magnesium stearate, sodium saccharine, cellulose, magnesium carbonate, etc. Examples of suitable pharmaceutical agents are described in "Remington's Pharmaceutical Sciences." Such compositions will contain a prophylactically or therapeutically effective amount of the antibody or fragment thereof, preferably in purified form, together with a suitable amount of carrier so as to provide the form for proper administration to the patient. The formulation should suit the mode of administration, which can be oral, intravenous, intraarterial, intrabuccal, intranasal, nebulized, bronchial inhalation, intrarectal, vaginal, topical or delivered by mechanical ventilation.

Active vaccines are also envisioned where antibodies like those disclosed are produced in vivo in a subject at risk of *A. fumigatus* infection. Such vaccines can be formulated for parenteral administration, e.g., formulated for injection via the intradermal, intravenous, intramuscular, subcutaneous, or even intraperitoneal routes. Administration by intradermal and intramuscular routes are contemplated. The vaccine could alternatively be administered by a topical route directly to the mucosa, for example by nasal drops, inhalation, by nebulizer, or via intrarectal or vaginal delivery. Pharmaceutically acceptable salts, include the acid salts and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Passive transfer of antibodies, known as artificially acquired passive immunity, generally will involve the use of intravenous or intramuscular injections. The forms of antibody can be human or animal blood plasma or serum, as pooled human immunoglobulin for intravenous (IVIG) or intramuscular (IG) use, as high-titer human IVIG or IG from immunized or from donors recovering from disease, and as monoclonal antibodies (MAb). Such immunity generally lasts for only a short period of time, and there is also a potential risk for hypersensitivity reactions, and serum sickness, especially from gamma globulin of non-human origin. However, passive immunity provides immediate protection. The antibodies will be formulated in a carrier suitable for injection, i.e., sterile and syringeable.

Generally, the ingredients of compositions of the disclosure are supplied either separately or mixed together in unit dosage form, for example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the disclosure can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

2. ADCC

Antibody-dependent cell-mediated cytotoxicity (ADCC) is an immune mechanism leading to the lysis of antibody-coated target cells by immune effector cells. The target cells are cells to which antibodies or fragments thereof comprising an Fc region specifically bind, generally via the protein part that is N-terminal to the Fc region. By "antibody having increased/reduced antibody dependent cell-mediated cytotoxicity (ADCC)" is meant an antibody having increased/reduced ADCC as determined by any suitable method known to those of ordinary skill in the art.

As used herein, the term "increased/reduced ADCC" is defined as either an increase/reduction in the number of target cells that are lysed in a given time, at a given concentration of antibody in the medium surrounding the target cells, by the mechanism of ADCC defined above, and/or a reduction/increase in the concentration of antibody, in the medium surrounding the target cells, required to achieve the lysis of a given number of target cells in a given time, by the mechanism of ADCC. The increase/reduction in ADCC is relative to the ADCC mediated by the same antibody produced by the same type of host cells, using the same standard production, purification, formulation and storage methods (which are known to those skilled in the art), but that has not been engineered. For example the increase in ADCC mediated by an antibody produced by host cells engineered to have an altered pattern of glycosylation (e.g., to express the glycosyltransferase, GnTIII, or other glycosyltransferases) by the methods described herein, is relative to the ADCC mediated by the same antibody produced by the same type of non-engineered host cells.

3. CDC

Complement-dependent cytotoxicity (CDC) is a function of the complement system. It is the processes in the immune system that kill pathogens by damaging their membranes without the involvement of antibodies or cells of the immune system. There are three main processes. All three insert one or more membrane attack complexes (MAC) into the pathogen which cause lethal colloid-osmotic swelling, i.e., CDC. It is one of the mechanisms by which antibodies or antibody fragments have an anti-viral effect.

IV. ANTIBODY CONJUGATES

Antibodies of the present disclosure may be linked to at least one agent to form an antibody conjugate. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules which have been attached to antibodies include toxins, anti-tumor agents, therapeutic enzymes, radionuclides, antiviral agents, chelating agents, cytokines, growth factors, and oligo- or polynucleotides. By contrast, a reporter molecule is defined as any moiety which may be detected using an assay. Non-limiting examples of reporter molecules which have been conjugated to antibodies include enzymes, radiolabels, haptens, fluorescent labels, phosphorescent molecules, chemiluminescent molecules, chromophores, photoaffinity molecules, colored particles or ligands, such as biotin.

Antibody conjugates are generally preferred for use as diagnostic agents. Antibody diagnostics generally fall within two classes, those for use in in vitro diagnostics, such as in a variety of immunoassays, and those for use in vivo diagnostic protocols, generally known as "antibody-directed imaging." Many appropriate imaging agents are known in the art, as are methods for their attachment to antibodies (see, for e.g., U.S. Pat. Nos. 5,021,236, 4,938,948, and 4,472,509). The imaging moieties used can be paramagnetic ions, radioactive isotopes, fluorochromes, NMR-detectable substances, and X-ray imaging agents.

In the case of paramagnetic ions, one might mention by way of example ions such as chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and/or erbium (III), with gadolinium being particularly preferred. Ions useful in other contexts, such as X-ray imaging, include but are not limited to lanthanum (III), gold (III), lead (II), and especially bismuth (III).

In the case of radioactive isotopes for therapeutic and/or diagnostic application, one might mention astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, indium$^{111}$, $^{59}$iron, $^{32}$phosphorus, rhenium$^{186}$, rhenium$^{188}$, $^{75}$selenium, $^{35}$sulphur, technicium$^{99m}$ and/or yttrium$^{90}$. $^{125}$I is often being preferred for use in certain embodiments, and technicium$^{99m}$ and/or indium$^{111}$ are also often preferred due to their low energy and suitability for long range detection. Radioactively labeled monoclonal antibodies of the present disclosure may be produced according to well-known methods in the art. For instance, monoclonal antibodies can be iodinated by contact with sodium and/or potassium iodide and a chemical oxidizing agent such as sodium hypochlorite, or an enzymatic oxidizing agent, such as lactoperoxidase.

Monoclonal antibodies according to the disclosure may be labeled with technetium$^{99m}$ by ligand exchange process, for example, by reducing pertechnate with stannous solution, chelating the reduced technetium onto a Sephadex column and applying the antibody to this column. Alternatively, direct labeling techniques may be used, e.g., by incubating pertechnate, a reducing agent such as $SNCl_2$, a buffer solution such as sodium-potassium phthalate solution, and the antibody. Intermediary functional groups which are often used to bind radioisotopes which exist as metallic ions to antibody are diethylenetriaminepentaacetic acid (DTPA) or ethylene diaminetetracetic acid (EDTA).

Among the fluorescent labels contemplated for use as conjugates include Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5,6-FAM, Fluorescein Isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, Tetramethylrhodamine, and/or Texas Red.

Additional types of antibodies contemplated in the present disclosure are those intended primarily for use in vitro, where the antibody is linked to a secondary binding ligand and/or to an enzyme (an enzyme tag) that will generate a colored product upon contact with a chromogenic substrate. Examples of suitable enzymes include urease, alkaline phosphatase, (horseradish) hydrogen peroxidase or glucose oxidase. Preferred secondary binding ligands are biotin and avidin and streptavidin compounds. The use of such labels is well known to those of skill in the art and are described, for example, in U.S. Pat. Nos. 3,817,837, 3,850,752, 3,939, 350, 3,996,345, 4,277,437, 4,275,149 and 4,366,241.

Yet another known method of site-specific attachment of molecules to antibodies comprises the reaction of antibodies with hapten-based affinity labels. Essentially, hapten-based affinity labels react with amino acids in the antigen binding site, thereby destroying this site and blocking specific antigen reaction. However, this may not be advantageous since it results in loss of antigen binding by the antibody conjugate.

Molecules containing azido groups may also be used to form covalent bonds to proteins through reactive nitrene intermediates that are generated by low intensity ultraviolet light (Potter and Haley, 1983). In particular, 2- and 8-azido analogues of purine nucleotides have been used as site-directed photoprobes to identify nucleotide binding proteins in crude cell extracts (Owens & Haley, 1987; Atherton et al., 1985). The 2- and 8-azido nucleotides have also been used to map nucleotide binding domains of purified proteins (Khatoon et al., 1989; King et al., 1989; Dholakia et al., 1989) and may be used as antibody binding agents.

Several methods are known in the art for the attachment or conjugation of an antibody to its conjugate moiety. Some attachment methods involve the use of a metal chelate complex employing, for example, an organic chelating agent such a diethylenetriaminepentaacetic acid anhydride (DTPA); ethylenetriaminetetraacetic acid; N-chloro-p-toluenesulfonamide; and/or tetrachloro-3α-6α-diphenylglycouril-3 attached to the antibody (U.S. Pat. Nos. 4,472,509 and 4,938,948). Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate. In U.S. Pat. No. 4,938,948, imaging of breast tumors is achieved using monoclonal antibodies and the detectable imaging moieties are bound to the antibody using linkers such as methyl-p-hydroxybenzimidate or N-succinimidyl-3-(4-hydroxyphenyl)propionate.

In other embodiments, derivatization of immunoglobulins by selectively introducing sulfhydryl groups in the Fc region of an immunoglobulin, using reaction conditions that do not alter the antibody combining site are contemplated. Antibody conjugates produced according to this methodology are disclosed to exhibit improved longevity, specificity and sensitivity (U.S. Pat. No. 5,196,066, incorporated herein by reference). Site-specific attachment of effector or reporter molecules, wherein the reporter or effector molecule is conjugated to a carbohydrate residue in the Fc region have also been disclosed in the literature (O'Shannessy et al., 1987). This approach has been reported to produce diagnostically and therapeutically promising antibodies which are currently in clinical evaluation.

V. IMMUNODETECTION METHODS

In still further embodiments, the present disclosure concerns immunodetection methods for binding, purifying, removing, quantifying and otherwise generally detecting *A. fumigatus* and its associated antigens. While such methods can be applied in a traditional sense, another use will be in quality control and monitoring of vaccine and other *A. fumigatus* stocks, where antibodies according to the present disclosure can be used to assess the amount or integrity (i.e., long term stability) of antigens in viruses. Alternatively, the methods may be used to screen various antibodies for appropriate/desired reactivity profiles.

Other immunodetection methods include specific assays for determining the presence of *A. fumigatus* in a subject. A wide variety of assay formats are contemplated, but specifically those that would be used to detect *A. fumigatus* in a fluid obtained from a subject, such as saliva, blood, plasma, sputum, semen or urine. In particular, semen has been demonstrated as a viable sample for detecting *A. fumigatus* (Purpura et al., 2016; Mansuy et al., 2016; Barzon et al., 2016; Gornet et al., 2016; Duffy et al., 2009; CDC, 2016; Halfon et al., 2010; Elder et al. 2005). The assays may be advantageously formatted for non-healthcare (home) use, including lateral flow assays (see below) analogous to home pregnancy tests. These assays may be packaged in the form of a kit with appropriate reagents and instructions to permit use by the subject of a family member.

Some immunodetection methods include enzyme linked immunosorbent assay (ELISA), radioimmunoassay (RIA), immunoradiometric assay, fluoroimmunoassay, chemiluminescent assay, bioluminescent assay, and Western blot to mention a few. In particular, a competitive assay for the detection and quantitation of *A. fumigatus* antibodies directed to specific epitopes in samples also is provided. The steps of various useful immunodetection methods have been described in the scientific literature, such as, e.g., Doolittle and Ben-Zeev (1999), Gulbis and Galand (1993), De Jager et al. (1993), and Nakamura et al. (1987). In general, the immunobinding methods include obtaining a sample suspected of containing *A. fumigatus*, and contacting the sample with a first antibody in accordance with the present disclosure, as the case may be, under conditions effective to allow the formation of immunocomplexes.

These methods include methods for purifying *A. fumigatus* or related antigens from a sample. The antibody will preferably be linked to a solid support, such as in the form of a column matrix, and the sample suspected of containing the *A. fumigatus* or antigenic component will be applied to the immobilized antibody. The unwanted components will be washed from the column, leaving the *A. fumigatus* antigen immunocomplexed to the immobilized antibody, which is then collected by removing the organism or antigen from the column.

The immunobinding methods also include methods for detecting and quantifying the amount of *A. fumigatus* or related components in a sample and the detection and quantification of any immune complexes formed during the binding process. Here, one would obtain a sample suspected of containing *A. fumigatus* or its antigens and contact the sample with an antibody that binds *A. fumigatus* or components thereof, followed by detecting and quantifying the amount of immune complexes formed under the specific conditions. In terms of antigen detection, the biological sample analyzed may be any sample that is suspected of containing *A. fumigatus* or *A. fumigatus* antigen, such as a tissue section or specimen, a homogenized tissue extract, a biological fluid, including blood and serum, or a secretion, such as feces or urine.

Contacting the chosen biological sample with the antibody under effective conditions and for a period of time sufficient to allow the formation of immune complexes (primary immune complexes) is generally a matter of simply adding the antibody composition to the sample and incubating the mixture for a period of time long enough for the antibodies to form immune complexes with, i.e., to bind to *A. fumigatus* or antigens present. After this time, the sample-antibody composition, such as a tissue section, ELISA plate, dot blot or Western blot, will generally be washed to remove any non-specifically bound antibody species, allowing only those antibodies specifically bound within the primary immune complexes to be detected.

In general, the detection of immunocomplex formation is well known in the art and may be achieved through the application of numerous approaches. These methods are generally based upon the detection of a label or marker, such as any of those radioactive, fluorescent, biological and enzymatic tags. Patents concerning the use of such labels include U.S. Pat. Nos. 3,817,837, 3,850,752, 3,939,350, 3,996,345, 4,277,437, 4,275,149 and 4,366,241. Of course, one may find additional advantages through the use of a secondary binding ligand such as a second antibody and/or a biotin/avidin ligand binding arrangement, as is known in the art.

The antibody employed in the detection may itself be linked to a detectable label, wherein one would then simply detect this label, thereby allowing the amount of the primary immune complexes in the composition to be determined. Alternatively, the first antibody that becomes bound within the primary immune complexes may be detected by means of a second binding ligand that has binding affinity for the antibody. In these cases, the second binding ligand may be linked to a detectable label. The second binding ligand is itself often an antibody, which may thus be termed a "secondary" antibody. The primary immune complexes are contacted with the labeled, secondary binding ligand, or antibody, under effective conditions and for a period of time sufficient to allow the formation of secondary immune complexes. The secondary immune complexes are then generally washed to remove any non-specifically bound labeled secondary antibodies or ligands, and the remaining label in the secondary immune complexes is then detected.

Further methods include the detection of primary immune complexes by a two-step approach. A second binding ligand, such as an antibody that has binding affinity for the antibody, is used to form secondary immune complexes, as described above. After washing, the secondary immune complexes are contacted with a third binding ligand or antibody that has binding affinity for the second antibody, again under effective conditions and for a period of time sufficient to allow the formation of immune complexes (tertiary immune complexes). The third ligand or antibody is linked to a detectable label, allowing detection of the tertiary immune complexes thus formed. This system may provide for signal amplification if this is desired.

One method of immunodetection uses two different antibodies. A first biotinylated antibody is used to detect the target antigen, and a second antibody is then used to detect the biotin attached to the complexed biotin. In that method, the sample to be tested is first incubated in a solution containing the first step antibody. If the target antigen is present, some of the antibody binds to the antigen to form a biotinylated antibody/antigen complex. The antibody/antigen complex is then amplified by incubation in successive solutions of streptavidin (or avidin), biotinylated DNA, and/or complementary biotinylated DNA, with each step adding additional biotin sites to the antibody/antigen complex. The amplification steps are repeated until a suitable level of amplification is achieved, at which point the sample is incubated in a solution containing the second step antibody against biotin. This second step antibody is labeled, as for example with an enzyme that can be used to detect the presence of the antibody/antigen complex by histoenzymology using a chromogen substrate. With suitable amplification, a conjugate can be produced which is macroscopically visible.

Another known method of immunodetection takes advantage of the immuno-PCR (Polymerase Chain Reaction) methodology. The PCR method is similar to the Cantor method up to the incubation with biotinylated DNA, however, instead of using multiple rounds of streptavidin and biotinylated DNA incubation, the DNA/biotin/streptavidin/antibody complex is washed out with a low pH or high salt buffer that releases the antibody. The resulting wash solution is then used to carry out a PCR reaction with suitable primers with appropriate controls. At least in theory, the enormous amplification capability and specificity of PCR can be utilized to detect a single antigen molecule.

A. ELISAs

Immunoassays, in their most simple and direct sense, are binding assays. Certain preferred immunoassays are the various types of enzyme linked immunosorbent assays (ELISAs) and radioimmunoassays (MA) known in the art. Immunohistochemical detection using tissue sections is also particularly useful. However, it will be readily appreciated that detection is not limited to such techniques, and western blotting, dot blotting, FACS analyses, and the like may also be used.

In one exemplary ELISA, the antibodies of the disclosure are immobilized onto a selected surface exhibiting protein affinity, such as a well in a polystyrene microtiter plate. Then, a test composition suspected of containing the *A. fumigatus* or *A. fumigatus* antigen is added to the wells. After binding and washing to remove non-specifically bound immune complexes, the bound antigen may be detected. Detection may be achieved by the addition of another anti-*A. fumigatus* antibody that is linked to a detectable label. This type of ELISA is a simple "sandwich ELISA." Detection may also be achieved by the addition of a second anti-*A. fumigatus* antibody, followed by the addition of a third antibody that has binding affinity for the second antibody, with the third antibody being linked to a detectable label.

In another exemplary ELISA, the samples suspected of containing the *A. fumigatus* or *A. fumigatus* antigen are immobilized onto the well surface and then contacted with the anti-*A. fumigatus* antibodies of the disclosure. After binding and washing to remove non-specifically bound immune complexes, the bound anti-*A. fumigatus* antibodies are detected. Where the initial anti-*A. fumigatus* antibodies are linked to a detectable label, the immune complexes may be detected directly. Again, the immune complexes may be detected using a second antibody that has binding affinity for the first anti-*A. fumigatus* antibody, with the second antibody being linked to a detectable label.

Irrespective of the format employed, ELISAs have certain features in common, such as coating, incubating and binding, washing to remove non-specifically bound species, and detecting the bound immune complexes. These are described below.

In coating a plate with either antigen or antibody, one will generally incubate the wells of the plate with a solution of the antigen or antibody, either overnight or for a specified period of hours. The wells of the plate will then be washed to remove incompletely adsorbed material. Any remaining available surfaces of the wells are then "coated" with a nonspecific protein that is antigenically neutral with regard to the test antisera. These include bovine serum albumin (BSA), casein or solutions of milk powder. The coating allows for blocking of nonspecific adsorption sites on the immobilizing surface and thus reduces the background caused by nonspecific binding of antisera onto the surface.

In ELISAs, it is probably more customary to use a secondary or tertiary detection means rather than a direct procedure. Thus, after binding of a protein or antibody to the well, coating with a non-reactive material to reduce background, and washing to remove unbound material, the immobilizing surface is contacted with the biological sample to be tested under conditions effective to allow immune complex (antigen/antibody) formation. Detection of the immune complex then requires a labeled secondary binding ligand or antibody, and a secondary binding ligand or antibody in conjunction with a labeled tertiary antibody or a third binding ligand.

"Under conditions effective to allow immune complex (antigen/antibody) formation" means that the conditions preferably include diluting the antigens and/or antibodies with solutions such as BSA, bovine gamma globulin (BGG) or phosphate buffered saline (PBS)/Tween. These added agents also tend to assist in the reduction of nonspecific background.

The "suitable" conditions also mean that the incubation is at a temperature or for a period of time sufficient to allow effective binding. Incubation steps are typically from about 1 to 2 to 4 hours or so, at temperatures preferably on the order of 25° C. to 27° C., or may be overnight at about 4° C. or so.

Following all incubation steps in an ELISA, the contacted surface is washed so as to remove non-complexed material. A preferred washing procedure includes washing with a solution such as PBS/Tween, or borate buffer. Following the formation of specific immune complexes between the test sample and the originally bound material, and subsequent washing, the occurrence of even minute amounts of immune complexes may be determined.

To provide a detecting means, the second or third antibody will have an associated label to allow detection. Preferably, this will be an enzyme that will generate color development upon incubating with an appropriate chromogenic substrate. Thus, for example, one will desire to contact or incubate the first and second immune complex with a urease, glucose oxidase, alkaline phosphatase or hydrogen peroxidase-conjugated antibody for a period of time and under conditions that favor the development of further immune complex formation (e.g., incubation for 2 hours at room temperature in a PBS-containing solution such as PBS-Tween).

After incubation with the labeled antibody, and subsequent to washing to remove unbound material, the amount of label is quantified, e.g., by incubation with a chromogenic substrate such as urea, or bromocresol purple, or 2,2'-azino-di-(3-ethyl-benzthiazoline-6-sulfonic acid (ABTS), or $H_2O_2$, in the case of peroxidase as the enzyme label. Quantification is then achieved by measuring the degree of color generated, e.g., using a visible spectra spectrophotometer.

In another embodiment, the present disclosure contemplates the use of competitive formats. This is particularly useful in the detection of *A. fumigatus* antibodies in sample. In competition-based assays, an unknown amount of analyte or antibody is determined by its ability to displace a known amount of labeled antibody or analyte. Thus, the quantifiable loss of a signal is an indication of the amount of unknown antibody or analyte in a sample.

Here, the inventor proposes the use of labeled *A. fumigatus* monoclonal antibodies to determine the amount of *A. fumigatus* antibodies in a sample. The basic format would include contacting a known amount of *A. fumigatus* monoclonal antibody (linked to a detectable label) with *A. fumigatus* antigen or particle. The *A. fumigatus* antigen or organism is preferably attached to a support. After binding of the labeled monoclonal antibody to the support, the sample is added and incubated under conditions permitting any unlabeled antibody in the sample to compete with, and hence displace, the labeled monoclonal antibody. By measuring either the lost label or the label remaining (and subtracting that from the original amount of bound label), one can determine how much non-labeled antibody is bound to the support, and thus how much antibody was present in the sample.

B. Western Blot

The Western blot (alternatively, protein immunoblot) is an analytical technique used to detect specific proteins or antibodies in a given sample of tissue homogenate or extract or other sample. It uses gel electrophoresis to separate native or denatured proteins by the length of the polypeptide (denaturing conditions) or by the 3-D structure of the protein (native/non-denaturing conditions). The proteins are then transferred to a membrane (typically nitrocellulose or PVDF), where they are probed (detected) using antibodies specific to the target protein.

Samples may be taken from whole tissue or from cell culture. In most cases, solid tissues are first broken down mechanically using a blender (for larger sample volumes), using a homogenizer (smaller volumes), or by sonication. Cells may also be broken open by one of the above mechanical methods. However, it should be noted that mold or environmental samples can be the source of protein and thus Western blotting is not restricted to cellular studies only. Assorted detergents, salts, and buffers may be employed to encourage lysis of cells and to solubilize proteins. Protease and phosphatase inhibitors are often added to prevent the digestion of the sample by its own enzymes. Tissue preparation is often done at cold temperatures to avoid protein denaturing.

The proteins of the sample are separated using gel electrophoresis. Separation of proteins may be by isoelectric point (pI), molecular weight, electric charge, or a combination of these factors. The nature of the separation depends on the treatment of the sample and the nature of the gel. This is a very useful way to determine a protein. It is also possible to use a two-dimensional (2-D) gel which spreads the proteins from a single sample out in two dimensions. Proteins are separated according to isoelectric point (pH at which they have neutral net charge) in the first dimension, and according to their molecular weight in the second dimension.

In order to make the proteins accessible to antibody detection, they are moved from within the gel onto a membrane made of nitrocellulose or polyvinylidene difluoride (PVDF). The membrane is placed on top of the gel, and a stack of filter papers placed on top of that. The entire stack is placed in a buffer solution which moves up the paper by capillary action, bringing the proteins with it. Another method for transferring the proteins is called electroblotting and uses an electric current to pull proteins from the gel into the PVDF or nitrocellulose membrane. The proteins move from within the gel onto the membrane while maintaining the organization they had within the gel. As a result of this blotting process, the proteins are exposed on a thin surface layer for detection (see below). Both varieties of membrane are chosen for their non-specific protein binding properties (i.e., binds all proteins equally well). Protein binding is based upon hydrophobic interactions, as well as charged interactions between the membrane and protein. Nitrocellulose membranes are cheaper than PVDF but are far more fragile and do not stand up well to repeated probings. The uniformity and overall effectiveness of transfer of protein from the gel to the membrane can be checked by staining the membrane with Coomassie Brilliant Blue or Ponceau S dyes. Once transferred, proteins are detected using labeled primary antibodies, or unlabeled primary antibodies followed by indirect detection using labeled protein A or secondary labeled antibodies binding to the Fc region of the primary antibodies.

C. Lateral Flow Assays

Lateral flow assays, also known as lateral flow immunochromatographic assays, are simple devices intended to detect the presence (or absence) of a target analyte in sample (matrix) without the need for specialized and costly equipment, though many laboratory-based applications exist that are supported by reading equipment. Typically, these tests are used as low resources medical diagnostics, either for home testing, point of care testing, or laboratory use. A widely spread and well-known application is the home pregnancy test.

The technology is based on a series of capillary beds, such as pieces of porous paper or sintered polymer. Each of these elements has the capacity to transport fluid (e.g., urine) spontaneously. The first element (the sample pad) acts as a sponge and holds an excess of sample fluid. Once soaked, the fluid migrates to the second element (conjugate pad) in which the manufacturer has stored the so-called conjugate, a dried format of bio-active particles (see below) in a salt-sugar matrix that contains everything to guarantee an optimized chemical reaction between the target molecule (e.g., an antigen) and its chemical partner (e.g., antibody) that has been immobilized on the particle's surface. While the sample fluid dissolves the salt-sugar matrix, it also dissolves the particles and in one combined transport action the sample and conjugate mix while flowing through the porous structure. In this way, the analyte binds to the particles while migrating further through the third capillary bed. This material has one or more areas (often called stripes) where a third molecule has been immobilized by the manufacturer. By the time the sample-conjugate mix reaches these strips, analyte has been bound on the particle and the third 'capture' molecule binds the complex. After a while, when more and more fluid has passed the stripes, particles accumulate and the stripe-area changes color. Typically there are at least two stripes: one (the control) that captures any particle and thereby shows that reaction conditions and technology worked fine, the second contains a specific capture molecule and only captures those particles onto which an analyte molecule has been immobilized. After passing these reaction zones, the fluid enters the final porous material—the wick—that simply acts as a waste container. Lateral Flow Tests can operate as either competitive or sandwich assays. Lateral flow assays are disclosed in U.S. Pat. No. 6,485,982.

D. Immunohistochemistry

The antibodies of the present disclosure may also be used in conjunction with both fresh-frozen and/or formalin-fixed, paraffin-embedded tissue blocks prepared for study by immunohistochemistry (IHC). The method of preparing tissue blocks from these particulate specimens has been successfully used in previous IHC studies of various prognostic factors and is well known to those of skill in the art (Brown et al., 1990; Abbondanzo et al., 1990; Allred et al., 1990).

Briefly, frozen-sections may be prepared by rehydrating 50 ng of frozen "pulverized" tissue at room temperature in phosphate buffered saline (PBS) in small plastic capsules; pelleting the particles by centrifugation; resuspending them in a viscous embedding medium (OCT); inverting the capsule and/or pelleting again by centrifugation; snap-freezing in −70° C. isopentane; cutting the plastic capsule and/or removing the frozen cylinder of tissue; securing the tissue cylinder on a cryostat microtome chuck; and/or cutting 25-50 serial sections from the capsule. Alternatively, whole frozen tissue samples may be used for serial section cuttings.

Permanent-sections may be prepared by a similar method involving rehydration of the 50 mg sample in a plastic microfuge tube; pelleting; resuspending in 10% formalin for 4 hours fixation; washing/pelleting; resuspending in warm 2.5% agar; pelleting; cooling in ice water to harden the agar; removing the tissue/agar block from the tube; infiltrating and/or embedding the block in paraffin; and/or cutting up to 50 serial permanent sections. Again, whole tissue samples may be substituted.

E. Immunodetection Kits

In still further embodiments, the present disclosure concerns immunodetection kits for use with the immunodetection methods described above. As the antibodies may be used to detect *A. fumigatus* or *A. fumigatus* antigens, the antibodies may be included in the kit. The immunodetection kits will thus comprise, in suitable container means, a first antibody that binds to *A. fumigatus* or *A. fumigatus* antigen, and optionally an immunodetection reagent.

In certain embodiments, the *A. fumigatus* antibody may be pre-bound to a solid support, such as a column matrix and/or well of a microtiter plate. The immunodetection reagents of the kit may take any one of a variety of forms, including those detectable labels that are associated with or linked to the given antibody. Detectable labels that are associated with or attached to a secondary binding ligand are also contemplated. Exemplary secondary ligands are those secondary antibodies that have binding affinity for the first antibody.

Further suitable immunodetection reagents for use in the present kits include the two-component reagent that comprises a secondary antibody that has binding affinity for the first antibody, along with a third antibody that has binding affinity for the second antibody, the third antibody being linked to a detectable label. As noted above, a number of exemplary labels are known in the art and all such labels may be employed in connection with the present disclosure.

The kits may further comprise a suitably aliquoted composition of the *A. fumigatus* or *A. fumigatus* antigens, whether labeled or unlabeled, as may be used to prepare a standard curve for a detection assay. The kits may contain antibody-label conjugates either in fully conjugated form, in the form of intermediates, or as separate moieties to be conjugated by the user of the kit. The components of the kits may be packaged either in aqueous media or in lyophilized form.

The container means of the kits will generally include at least one vial, test tube, flask, bottle, syringe or other container means, into which the antibody may be placed, or preferably, suitably aliquoted. The kits of the present disclosure will also typically include a means for containing the antibody, antigen, and any other reagent containers in close confinement for commercial sale. Such containers may include injection or blow-molded plastic containers into which the desired vials are retained.

F. Vaccine and Antigen Quality Control Assays

The present disclosure also contemplates the use of antibodies and antibody fragments as described herein for use in assessing the antigenic integrity of an allergen/antigen in a sample. Biological medicinal products like vaccines differ from chemical drugs in that they cannot normally be characterized molecularly; antibodies are large molecules of significant complexity and have the capacity to vary widely from preparation to preparation. They are also administered to healthy individuals, including children at the start of their lives, and thus a strong emphasis must be placed on their quality to ensure, to the greatest extent possible, that they are efficacious in preventing or treating life-threatening disease, without themselves causing harm.

The increasing globalization in the production and distribution of vaccines has opened new possibilities to better manage public health concerns but has also raised questions about the equivalence and interchangeability of vaccines procured across a variety of sources. International standardization of starting materials, of production and quality control testing, and the setting of high expectations for regulatory oversight on the way these products are manufactured and used, have thus been the cornerstone for continued success. But it remains a field in constant change, and continuous technical advances in the field offer a promise of developing potent new weapons against the oldest public health threats, as well as new ones—malaria, pandemic influenza, and HIV, to name a few—but also put a great pressure on manufacturers, regulatory authorities, and the wider medical community to ensure that products continue to meet the highest standards of quality attainable.

Thus, one may obtain an antigen/allergen or vaccine from any source or at any point during a manufacturing process. The quality control processes may therefore begin with preparing a sample for an immunoassay that identifies binding of an antibody or fragment disclosed herein to an antigen/allergen. Such immunoassays are disclosed elsewhere in this document, and any of these may be used to assess the structural/antigenic integrity of the antigen/allergen. Standards for finding the sample to contain acceptable amounts of antigenically correct and intact antigen may be established by regulatory agencies.

Another important embodiment where antigen integrity is assessed is in determining shelf-life and storage stability.

Most medicines, including vaccines, can deteriorate over time. Therefore, it is critical to determine whether, over time, the degree to which an antigen/allergen, such as in a vaccine, degrades or destabilizes such that is it no longer antigenic and/or capable of generating an immune response when administered to a subject. Again, standards for finding the sample to contain acceptable amounts of antigenically intact antigen/allergen may be established by regulatory agencies.

In certain embodiments, antigens/allergens may contain more than one epitope. In these cases, it may prove useful to employ assays that look at the binding of more than one antibody, such as 2, 3, 4, 5 or even more antibodies. These antibodies bind to closely related epitopes, such that they are adjacent or even overlap each other. On the other hand, they may represent distinct epitopes from disparate parts of the antigen/allergen. By examining the integrity of multiple epitopes, a more complete picture of the antigen's/allergen's overall integrity, and hence ability to generate a protective immune response, may be determined.

Antibodies and fragments thereof as described in the present disclosure may also be used in a kit for monitoring vaccination procedures by detecting the presence of *A. fumigatus* antibodies. Antibodies, antibody fragment, or variants and derivatives thereof, as described in the present disclosure may also be used in a kit for monitoring vaccine manufacture with the desired immunogenicity.

VI. EXAMPLES

The following examples are included to demonstrate preferred embodiments. It should be appreciated by those of skill in the art that the techniques disclosed in the examples that follow represent techniques discovered by the inventor to function well in the practice of embodiments, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1—Materials and Methods

Characteristics of Subjects with ABPM.

Evidence of mold hypersensitivity based on skin testing was as follows: Patient 1 (P1): *Aspergillus, Cephalsporium*, Mold mix #1 (GREER), Mold mix #2 (GREER); patient 2 (P2): *Alternaria, Aspergillus, Helminthosporium, Cladosporium, Eppicoccum, Penicillium*; patient 3 (P3): *Aspergillus*, Epicoccum, Hormodendrum, Penicillium, Alternaria.

The first patient (P1) is an adolescent male with history of cystic fibrosis. He has significantly elevated total serum IgE as well as evidence of *Aspergillus* precipitins, in the setting of recurrent exacerbations that improved with steroids. Of note, while he has evidence of a IgE sensitization to multiple molds, his skin testing to other common aeroallergens was negative. His surveillance sputum cultures grew *Aspergillus fumigatus* at least 5 times, but, to date, no other fungal species were isolated.

The second patient (P2) is an adult male with cystic fibrosis. The diagnosis of ABPM was made based on markedly elevated serum IgE and evidence of mold sensitization by skin test, including *Apergillus* spp. Interestingly, serum testing for *Aspergillus precipitans* was negative. This patient repeatedly grew a number of *Aspergillus* spp, including *Aspergillus* fumigatus, *Aspergillus terreus*, and *Aspergillus nidulans* from surveillance sputum cultures.

The third patient (P3) is an elderly man with long-standing history of asthma, without evident bronchiectasis. He has had markedly elevated total IgE and evidence of *Aspergillus* sensitization based on significantly elevated *Aspergillus*-specific IgE in ImmunoCAP. He had a broad pattern of allergic sensitization including animal dander, grasses, weeds, and trees in addition to mold sensitization. He was not evaluated for the presence of *Aspergillus* precipitins. He grew *Aspergillus fumigatus* a single time from sputum culture.

Human Hybridoma Generation.

IgE secreting human hybridomas were generated with using an overall scheme similar to that the inventors have published previously for making IgG mAbs, but with many modifications (Dombrowicz et al., 1996; Gautam et al., 2007). Previously cryopreserved samples were thawed rapidly in a 37° C. water bath and washed in 10 ml of prefusion medium (ClonaCell-HY 03801; Stemcell Technologies). The cells were counted and viability was assessed with trypan blue staining (Gibco 15250-061) before plating. For every 2 million viable cells, the following was then added: 30 ml of warmed prefusion medium, 20 µl of CpG stock (2.5 mg/ml; ODN 2006), 1 µl each of mouse anti-human kappa (Southern Biotech; 9230-01) and mouse anti-human lambda (Southern Biotech; 9180-01), and 1 million gamma irradiated NIH3T3 fibroblast line genetically engineered to constitutively express cell-surface human CD154 (CD40 ligand), secreted human B-cell activating factor (BAFF) and human IL-21 (kindly provided by Dr. Deepta Bhattacharya; Washington University in St. Louis). The mixture then was plated into 96-well flat bottom plate (Falcon, 353072) at 300 µl/well, and plates were incubated at 37° C. with 5% CO2 for 6 days, prior to screening for IgE secretion using an ELISA.

IgE Screening ELISA.

Omalizumab was used as a capture antibody, coating 384-well black ELISA plates (Greiner, 781076) at a concentration of 10 µg/ml in carbonate binding buffer overnight at 4° C. The plates then were blocked with 100 µl of blocking solution/well and incubated at room temperature for 1 h. Blocking solution was prepared with 10 g of powdered milk, 20 ml of goat serum, and 100 ml of 10× phosphate-buffered saline (PBS), mixed to a 1 liter final volume with distilled $H_2O$. Plates were washed five times with PBS, and 100 µl of supernatant was transferred from one well of a 96-well plate containing B-cell lines, using an VIAFLO-384 electronic pipetting device (Integra Biosciences). The plates were incubated at room temperature for 1 h prior to five washes with PBS. Secondary antibody (mouse anti-human IgE Fc; Southern biotech, 9160-05) was applied at a 1:1,000 dilution in blocking solution using 25 µl/well, and the plates were again incubated at room temperature for 1 h. After 10 washes with PBS, fluorogenic peroxidase substrate solution (QuantaBlu; Thermo Scientific 15162) was added at 25 µl/well, as per manufacturer instructions, and the plates were incubated at room temperature for 30 min before addition of stop solution. Relative fluorescence intensity was determination on a Molecular Devices plate reader set for excitation and emission maxima of 325 nm and 420 nm, respectively.

Electrofusion of B-Cells with Myeloma Fusion Partner.

HMMA2.5 non-secreting myeloma cells (kindly provided by Marshall Posner) were counted and suspended as 10 million cells/ml in warmed cytofusion medium composed of 300 mM sorbitol (Fisher, BP439-500), 0.1 mM calcium acetate (Fisher, AC21105-2500), 0.5 mM magnesium acetate (Fisher, AC42387-0050), and 1.0 mg/ml of bovine serum albumin (Sigma, A2153). After 8 days in 96-well plates, cells were pipetted gently into microcentrifuge tubes containing 1 ml of warmed cytofusion medium. B-cells and HMMA2.5 cells were centrifuged at 900 g for 3 min, the supernatants were decanted, and the pellets were suspended in 1 ml of cytofusion medium; this process was repeated three times to ensure equilibration to the cytofusion medium. The cytofusion medium then was decanted gently from each sample tube such that 100 µl remained and the pellet was retained. HMMA2.5 cells were then suspended in cytofusion medium to achieve a concentration of 10 million cells/ml. Then, 125 µl of HMMA2.5 cell suspension was added to each sample tube and the mixture was pipetted into cytofusion cuvettes (BTX, 450125), and the cuvette placed in a BTX cuvette holder (BTX Safety stand, model 630B). Cytofusion was performed using a BTX ECM 2001 generator (BTX; 45-0080) with the electrical discharge programed to run with following settings: a prefusion AC current of 70 V for 40 s, followed by a DC current pulse of 360 V for 0.04 ms and then a postfusion AC current of 40 V for 9 s. After fusion, the cuvettes were incubated at 37° C. for 30 min. The content of each cuvette was then added to 20 ml of hypoxanthine-aminopterin-thymidine (HAT) medium containing ouabain, composed of the following: 500 ml of post-fusion medium (Stemcell Technologies, 03805), one vial 50 HAT (Sigma, H0262), and 150 µl of a 1 mg/ml stock of ouabain (Sigma, 013K0750). Fusion products then were plated at 50 µl/well into 384-well plates (Nunc, 164688), followed by incubation at 37° C. for 14 days before screening hybridomas for IgE antibody production by ELISA.

MAb Production and Purification.

Wells containing hybridomas producing IgE antibodies were cloned biologically by indexed single cell flow cytometric sorting into 384-well culture plates. Once clonality was achieved, each hybridoma was expanded in postfusion medium (Stemcell Technologies, 03805) until 50% confluent in 75-cm$^2$ flasks (Corning, 430641). MAb was expressed by large-scale growth of the hybridoma in serum free medium (Gibco Hybridoma-SFM; Invitrogen, 12045084). After harvesting cells in 75-cm$^2$ flasks with cell scraper, the hybridomas were washed in serum-free medium and split equally among four 225-cm$^2$ flasks (Corning, 431082) containing 250 ml of serum-free medium. IgE antibody was then purified by immunoaffinity chromatography (Omalizumab covalently coupled to GE Healthcare NHS activated HiTRAP; 17-0717-01) and visualized by SDS-PAGE for purity ImmunoCAP and Western Blot Analysis.

An antibody was considered positive if it bound to *A. fumigatus* in ImmunoCAP (>1.0 kUA/L) and/or one or more *A. fumigatus* extracts in ELISA (RFU>5× background). It should be noted that the inventors chose a much higher cutoff for defining ImmunoCAP positivity than the standard cutoff for serum analysis. Since they were using IgE mAbs at a known concentration, the inventors were screening for allergen presence in the assay, not measuring IgE antibody. For each positive mAb, Western blot analysis was performed against all four extracts. Immunoprecipitation followed by mass spectrometry analysis was attempted for each mAb which bound to one or more extracts in ELISA and/or in Western blot.

Mold extracts obtained from GREER, Hollister-Stier, ALKB, and Allergy Laboratories were mixed with loading buffer, separated by SDS-PAGE under nonreducing/nondenaturing conditions and transferred to PVDL membrane. After blocking overnight at 4° C., monoclonal IgE containing supernatant from hybridoma cultures was added for 1 hour at room temperature. After washing in PBS, HRP conjugated mouse anti-human IgE secondary antibody was added at 1:1,000 dilution in blocking solution and the blot incubated for 1 hour at room temperature. Blots were visualized using chemiluminescent substrate (Supersignal Pico; Thermo Scientific 34577) on a GE Healthcare ImageQuant LAS 4000 Imager.

Example 2—Results

*Aspergillus*-Reactive IgE Secreting Human Hybridomas can be Generated from PBMCs of Subjects with ABPM.

The inventors selected three subjects with ABPM who had high levels of circulating *Aspergillus*-specific IgE. The inventors' hope was that their mold hypersensitivity would be reflected in their memory B-cell population from which the inventors developed panels of IgE mAbs directed against *Aspergillus*. They expanded B-cells in culture as described in the methods section and calculated minimum IgE B-cell frequencies based on isotype-specific ELISA results (see Table A). They observed an IgE-encoding B-cell frequency of 58.3, 38.3, 24.2 per 10 million peripheral blood mononuclear cells (PBMCs) from each subject respectively and established 70 stable human hybridomas from B-cell lines secreting IgE antibodies. Of note, none of the human IgE mAbs were screened for reactivity toward *Aspergillus*, or any other specificity, prior to their generation. Thus, no antigen-specific bias was introduced. All mAbs were selected only based on the B-cell's production of the IgE isotype. Purified human IgE mAb used for characterizations was produced by large scale hybridoma growth in serum free culture medium.

Allergen Extracts and IgE Binding Analysis.

*Aspergillus* reactivity was identified by the presence of specific activity to *Aspergillus* using the ImmunoCAP (Thermofisher Scientific) or by specific binding to one or more of the *A. fumigatus* extracts commercially available for human use in the US [GREER, Hollister-Stier (HS), ALK-Abelló (ALKB), and Allergy Laboratories (AlrgyL)]. Specific binding to *A. fumigatus* extract was evaluated both by indirect fluorescence ELISA and Western blot—all 70 human mAbs were screened. It should be noted that some of these antibodies may be reactive toward *Aspergillus* components which are not present in any of the commercially available materials, resulting in an underestimation of the response. Of the 70 mAbs (see Table E for full list), 26 bound to the well-characterized *Aspergillus* allergosorbents in the ImmunoCAP and/or one or more allergenic extracts in ELISA (see Table B). All 26 *Aspergillus*-reactive IgE mAbs were then tested for their ability to bind to purified recombinant Asp f 1 protein. Three mAbs, two from patient 1 (P1) (17A5 and 4F8) and one from patient 2 (P2) (14H4) were Asp f 1-specific—see Table C for genetic features of Asp f 1-specific mAbs. Notably, only two of the three Asp f 1 antibodies were detected by ImmunoCAP, and those were weak reactors, while the third was undetected (Table B). FIGS. 1A-B show Asp f 1-specific IgE binding by ELISA and Western blot using the four manufacturers' extracts. Only ALKB extract possessed detectable levels of Asp f 1. Additionally, reactivity for ALKB extract was very high, in several cases reaching the upper maximum limit of this particular ELISA.

As shown in Table B, reactivity varied extensively among the mAbs and extracts. ImmunoCAP was the most consistent in detecting binding of 22 of the 26 antibodies. Binding to the four manufacturers' extracts was highly variable. The number of antibodies that reacted to the extracts, either in ELISA or Western blot analysis, were as follows: GREER, 6 mAbs; AlrgyL, 8 mAbs; HS, 12 mAbs; ALKB, 16 mAbs. Of the 26 antibodies, only 8 reacted to more than one allergenic extract. Only four antibodies bound targets in each of the manufacturers' extracts. ELISA and Western blot analysis showed variability of human *Aspergillus*-reactive IgE mAbs binding to extracts (data not shown).

Immunoprecipitation and Mass Spectroscopy.

Since the inventors' panel of IgE mAbs were generated from subjects with ABPM without bias towards any given allergen, the targets of these antibodies likely represent a stochastic sampling of the mold proteins generating the immune response during the development of the disease. They next set out to define the target proteins of the 26 *Aspergillus*-reactive IgE mAbs using immunoaffinity purification and mass spectrometry and the commercially available allergen extracts as source material. As shown in Table C, the inventors were able to identify 14 IgE mAb target proteins. The majority of *Aspergillus* proteins identified contain intrinsic enzymatic activity associated with fungal metabolism. Interestingly, they identified an endochitosanase, which is secreted in high amounts by growing fungus. A previous study using proteomic screening with serum from patients with ABPM also suggested that this protein may be a target of IgE antibodies (Gautam et al., 2007). The enzyme pectate lyase was the target protein of two mAbs, 3D4 and 21E2. Proteins with potential as virulence factors such as Asp f 1 (the ribotoxin mitogillin) were identified by three antibodies that bound recombinant Asp f 1 (17A5, 4F8 and 14H4). The target of 10C4 is a mannoprotein, whose ortholog in *Talaromyces* is a virulence factor associated with sequestration of host arachidonic acid (Sze et al., 2017). While both Asp f 1 and Asp f 9 were targets of these mAbs, the majority of the characterized targets are not proteins with recognized allergenic potential.

Human Transgenic Mouse Anaphylaxis.

Figure 2:
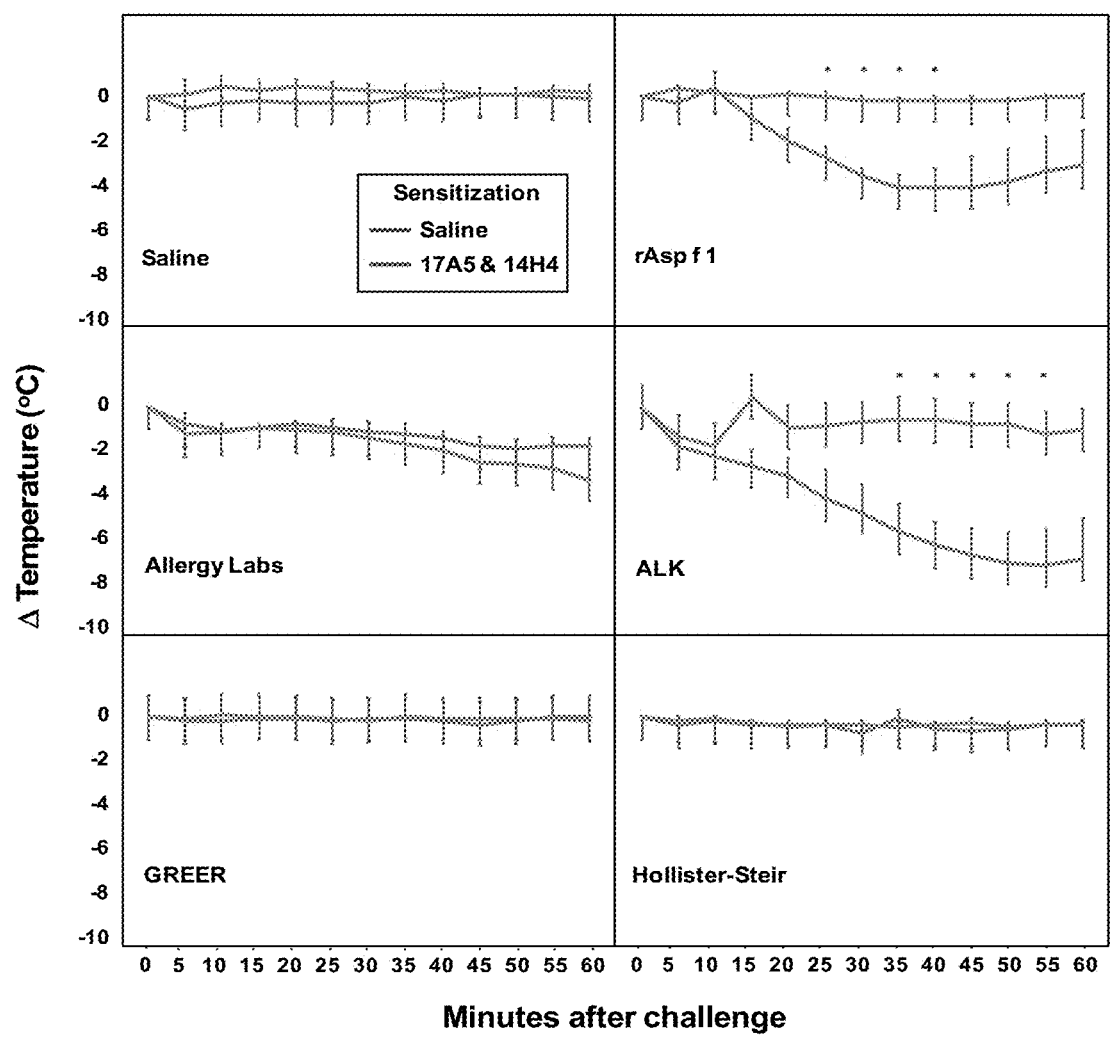

To evaluate commercial extracts for functional levels of the major *Aspergillus* allergen Asp f 1, the inventors employed a transgenic mouse model of anaphylaxis (see FIG. 2). Mice expressing the human FcεRIα were sensitized with injections of 17A5 and 14H4, two Asp f 1-specific IgE mAbs, or sham sensitized with saline injections. Human mAbs 17A5 and 14H4 were selected because they bind distinct, non-competing, epitopes on Asp f 1 and are able to function together to trigger mast cell degranulation. Mice sensitized with mAbs and sham sensitized mice were then challenged by via an intraperitoneal injection with each of the commercially prepared extracts, recombinant Asp f 1 or a saline control. Mice undergoing anaphylaxis develop marked cutaneous vasodilation, which produced to a fall in mouse's core body temperature. Only those mice injected with the recombinant Asp f 1 and the ALKB *Aspergillus fumigatus* extract containing Asp f 1 elicited a significant fall in temperature when compared to the sham sensitized animals.

Example 3—Discussion

This study provides the first description of a novel method to generate naturally-occurring human allergen-specific IgE mAbs. Until now, attempts to clone human IgE antibodies from peripheral blood cells by flow cytometry has proven difficult to impossible, due to their low frequency and poor B-cell receptor expression. Human monoclonal IgE act as tools to evaluate both the quantity and specificity of allergenic components in *Aspergillus fumigatus* extracts. Only allergen proteins that are present in the manufacturing process, appropriately folded, and not proteolytically degraded can be detected by these antibodies. The inventors have used a large panel of human IgE mAbs, generated in an unbiased manner from patients with ABPM, to identify the presence of relevant allergenic proteins in both the four commercial allergenic extracts and the *Aspergillus fumigatus* allergosorbent used for IgE antibody serology worldwide in the state of the art ImmunoCAP autoanalyzer. Significant variability in allergen content was found among extracts, which in the case of Asp f 1 is shown to be functionally significant. Also, nine potential new allergens were identified that are produced by *Aspergillus* and that elicit a human IgE antibody response.

Respiratory disease involving type I hypersensitivity following mold exposure is common and associated with significant morbidity. Evaluation for sensitization to mold is largely dependent on either skin testing with commercially available extracts or the use of in vitro testing for allergen specific IgE. Additionally, mold allergen extracts are used in routine clinical practice for immunotherapy. Despite their common usage in clinical practice, no mechanism for standardizing mold extracts currently exists and available commercial mold allergen extracts are not standardized for their allergen content or even their starting source materials used in their manufacture. Production of panels of monoclonal IgE from patients with type I hypersensitivity as shown in this study provides a unique tool, with de facto biological relevance to human disease. It allows more accurate assessment of the allergen content which is vital in better understanding the results of their diagnostic and therapeutic use. Previous attempts to standardize mold extracts using heterogeneous polyclonal IgE antibodies derived from human serum have been complicated as a result of the inherent variability of the allergen-specific IgE among humans. Moreover, the absolute and relative levels of allergen-specific IgE in individuals are constantly changing over time. The polyclonal nature of serum derived IgE as a mixture of many antibodies with distinct specificities and affinities, directed toward many different epitopes limits the ability to identify specific protein targets that elicit humoral IgE responses against these allergens. The ability to study the molecular interaction of IgE with its target allergen proteins by this method is thus greatly limited. The development of naturally-occurring human monoclonal IgE from patients with *Aspergillus* allergy represents a significant new tool for evaluating the biological relevance of the components of allergen extracts, and for understanding the development of allergic pathology.

The inventors selected three subjects with ABPM, having high circulating *Aspergillus*-specific IgE levels with the hope that their mold hypersensitivity would be reflected in their memory B cell population from which they would develop panels of monoclonal IgE antibodies directed against *Aspergillus*. These subjects possessed high circulating frequencies of B cells encoding IgE antibodies, averaging 14.5 cells per 10 million PBMCs. In the inventors' experience, this is 2-5 fold higher than subjects with allergies to common aeroallergens or foods. The inventors generated a total of 70 IgE mAbs. Consistent with the primacy of *Aspergillus* sensitization in the development of ABPM, one third of the monoclonal antibodies showed detectable activity against *Aspergillus fumigatus*. As these monoclonal IgEs were isolated in an unbiased manner, these antibodies represent a stochastic sampling of the patients total IgE repertoire. This data confirms that patients with ABPM mount a dramatic allergic response directed against the mold. It should be noted that some of these antibodies may be reactive toward *Aspergillus* components which are not present in any of the commercially available materials, resulting in an underestimation of the response.

Of the 26 *Aspergillus*-reactive human IgE mAbs generated, only 4 showed (one each from P1 & P3, two from P2) evidence of binding to all four manufacturer's extracts and the *Aspergillus* antigens on the ImmunoCAP allergosorbent. This demonstrates the tremendous variability of relevant *Aspergillus* antigens in these extracts. The absence of secreted proteins such as Asp f 1, glycanosyltransferase and endochitosanase in all the tested extracts except ALKB suggests that some of the heterogeneity seen is likely due to the inclusion of secreted proteins in the final preparation of the extract that varies with the media to grow the fungus. The target protein of 1D3, acetylhexosaminidase, however, is present in all extracts except for ALKB. A significant number of antibodies bind the allergen extracts, but do not have target proteins that could be detected by mass spectrometry. These antibodies may be directed against glycan derivatives from the fungal cell wall or other non-proteanaceous components of the allergen extract. The World Health Organization and International Union of Immunological Societies (WHO/IUIS) Allergen Nomenclature database lists 23 allergens (world-wide-web at allergen.org), from which only 2 (Asp f 1 and Asp f 9) were recognized by 4 of the 14 IgE mAbs with identifiable targets. The remaining 10 IgE mAbs allowed the identification of potentially new *Aspergillus* allergens. While additional characterization of the IgE antibody response to the newly identified proteins remains to be undertaken, this study suggests the response to *Aspergillus* in ABPM is broader than previously realized, and it raises the question of whether a similarly unremarked diversity of allergenic response to mold in asthma or atopic dermatitis may also be present.

This study raises significant questions about the reliability of diagnostic and therapeutic use of the currently available commercial *Aspergillus* allergen extracts. The biological relevance of the variability in extract content is highlighted by the inability of 75% of the commercially produced allergen extracts to induce anaphylaxis in a humanized mouse model that is ideally sensitized to Asp f 1. Development of human monoclonal IgE provides a new and biologically relevant tool to to investigate these widely used extracts for their content of allergenic proteins. Given the diversity of potentially novel allergens seen in this study, prior to attempting standardization of the existing mold extracts, significant additional work needs to be undertaken to clarify the patterns of allergic sensitization in patients with diverse expressions of mold allergy, including ABPM, asthma with fungal sensitization, and atopic dermatitis. Understanding the patterns of specific IgE response to these allergenic proteins in these diverse disease states may allow us to move forward towards an effective and reliable standardized *Aspergillus* extracts.

TABLE A

Subject demographics and hybridoma yield

| Subject code | Age | Allergic disease | Total serum IgE (kU IgE/L) | *A. fumigatus* ImmunoCAP (kUA/L) | IgE B-cell frequency (per $10^7$ PBMCs) | IgE hybridomas generated |
|---|---|---|---|---|---|---|
| P1 | 17 | CF/ABPM | 11,840 | 58.3 | 16.0 | 15 |
| P2 | 22 | CF/ABPM | 13,391 | 38.3 | 13.0 | 38 |
| P3 | 89 | Asthma/ABPM | 11,146 | 24.2 | 14.5 | 17 |

Subject age, total serum IgE. and *Aspergillus fumigatus* serum quantification are shown. IgE B-cell frequencies is expressed as the number of IgE positive cells per 10 million PBMCs. The total IgE expressing human hybridomas generated for each subject is listed.

TABLE B

IgE hybridoma reactivities

| Subject code | IgE Hybridoma | *A fumigatus* ImmunoCAP (kUA/L) | *A. fumigatus* extract reactivity ELISA | | | | *A. fumigatus* extract reactivity WB | | | | Immuno-precipitation |
|---|---|---|---|---|---|---|---|---|---|---|---|
| | | | GREER | HS | ALKB | AlrgyL | GREER | HS | ALKB | AlrgyL | |
| P1 | 17A5 | 1.84 | − | − | + | − | − | − | + | − | + |
| | 10C4 | 10.2 | − | + | − | + | − | + | − | + | + |
| | 4F8 | 0.16 | − | − | + | − | − | − | + | − | + |
| | 15C12 | 2.55 | − | − | − | − | − | − | − | − | − |
| | 1C9 | 9.39 | + | + | + | + | + | + | + | + | + |
| | 7C7 | 0.18 | − | + | + | − | − | − | − | − | − |
| P2 | 1D3 | 6.51 | + | + | − | + | + | + | − | + | + |
| | 12C8 | 5.63 | − | − | − | − | − | − | − | − | − |
| | 8D6 | 8.68 | − | − | − | − | − | − | − | − | − |
| | 16C5 | 0.16 | − | + | + | − | − | − | − | − | − |
| | 4E12 | 36.2 | + | + | + | + | + | + | − | − | + |
| | 2C8 | 16.2 | − | − | + | − | − | − | − | − | + |
| | 5C6 | >100 | − | − | + | − | − | + | − | + | + |
| | 14H4 | 2.99 | − | − | + | − | − | − | + | − | + |
| | 2G11 | 0.79 | − | − | + | − | − | − | − | − | − |
| | 21E2 | 6.34 | − | − | + | − | − | + | − | − | + |
| | 3H5 | 44.7 | − | − | − | − | − | − | − | − | − |
| | 22H5 | 7.51 | − | − | − | − | − | − | − | − | − |
| | 3D4 | 5.88 | − | − | + | − | − | + | − | − | + |
| | 3F3 | 61.6 | − | − | + | − | − | − | + | − | + |
| | 5B5 | >100 | + | + | + | + | − | − | − | − | + |

TABLE B-continued

IgE hybridoma reactivities

| Subject code | IgE Hybridoma | *A fumigatus* ImmunoCAP (kUA/L) | *A. fumigatus* extract reactivity ELISA | | | | *A. fumigatus* extract reactivity WB | | | | Immuno-precipitation |
|---|---|---|---|---|---|---|---|---|---|---|---|
| | | | GREER | HS | ALKB | AlrgyL | GREER | HS | ALKB | AlrgyL | |
| | 9C3 | >100 | − | + | + | + | − | − | − | − | + |
| | 3F8 | 1.92 | − | − | − | − | − | − | − | − | − |
| P3 | 9E1 | 1.63 | − | − | − | − | − | − | − | − | − |
| | 14G1 | 1.51 | − | − | − | − | − | − | − | − | − |
| | 11E3 | 1.26 | + | + | + | + | − | − | − | − | − |

All human IgE mAbs with detectable binding in ImmunoCAP or to commercial extract in ELISA and/or Western blot. *Aspergillus fumigatus* ImmunoCAP was considered positive if >1.0 kUA/L. IgE mAb binding to *Aspergillus fumigatus* extracts in ELISA: (−) no binding detected, (+) binding >5 times background; assays were performed in triplicate. MAb binding to *Aspergillus fumigatus* allergenic extracts in Western blot: (−) no binding detected, (+) binding detected. If binding was detected by any method, immunoprecipitation was attempted: (−) no target protein identified, (+) target protein identified by mass spectrometry at >10 times control.

TABLE C

Genetic features of Asp f 1-specific human IgE mAbs

| IgE MAb | Light Chain | Germline Gene Segments | | | | | | CDR3 Length | Variable Gene Mutations | | | |
|---|---|---|---|---|---|---|---|---|---|---|---|---|
| | | VH | D | JH | VL | JL | AA Junction | | VH NT | VH AA | VL NT | VL AA |
| 17A5 | λ | 3-11 | 3-10 | 6 | 1-51 | 2 | CARDAGYYHGSGNNAIYHGMDVW (SEQ ID NO: 132) | 21 | 28 | 13 | 27 | 12 |
| 14H4 | λ | 5-51 | 3-22 | 3 | 3-1 | 1 | CARVSRYYYDSRSYYPDAFDIW (SEQ ID NO: 133) | 20 | 22 | 11 | 12 | 8 |
| 4F8 | κ | 4-34 | 3-9 | 3 | 1-6 | 1 | CARIGEKTGDYTIW (SEQ ID NO: 134) | 11 | 13 | 6 | 12 | 6 |

Asp f 1-specific IgE mAbs from subjects P1 and P2 are shown. Antibody germline gene segment usages are shown for variable (V), diverse (D), and joining (J) regions of both light and heavy chains based on ImMunoGeneTics, IMGT database. The length and sequence of the CDR3 region and number of nucleotide and amino acid mutations are shown.

TABLE D

*Aspergillus*-reactive human IgG mAh target proteins

| IgE mAb | Subject Code | ImmunoCAP Reactivity (kUA/L) | Binding to *Aspergillus* Extract | | | Allergen name | Sequence ID |
|---|---|---|---|---|---|---|---|
| | | | ELISA | Western Blot | Mass Spectrometry | | |
| 17A5 | P1 | 1.84 PAU/L | + | 18 kDa band | Ribotoxin, Mitogillin | Asp f 1 | XP_001266297.1 |
| 4F8 | P1 | 0.16 PAU/L | + | 18 kDa band | Ribotoxin, Mitogillin | Asp f 1 | XP_001266297.1 |
| 10C4 | P1 | 10.2 PAU/L | + | 20 kDa band | Galactomannoprotein | ? | XP_746510.1 |
| 1C9 | P1 | 9.39 PAU/L | + | 75 kDa band | Glycosyltransferase | ? | OXN24808.1 |
| 1D3 | P2 | 6.51 PAU/L | + | 140 kDa band | Acetylhexosaminidase | ? | XP_747307.1 |
| 14H4 | P2 | 2.99 PAU/L | + | 18 kDa band | Ribotoxin, Mitogillin | Asp f 1 | XP_001266297.1 |
| 21E2 | P2 | 6.34 PAU/L | + | 27 kDa band | Pectate lyase | ? | XP_747393.1 |
| 2C8 | P2 | 16.20 PAU/L | + | — | Endochitosanase | ? | ABZ88800.1 |
| 5C6 | P2 | >100 PAU/L | + | 35 kDa band | Glucanase | Asp f 9 | XP_752985.1 |
| 4E12 | P2 | 36.2 PAU/L | + | — | Lactonase | ? | XP_749654.1 |
| 9C3 | P2 | >100 PAU/L | + | — | Peptidase | ? | XP_750573.1 |
| 3F3 | P2 | 61.6 PAU/L | + | 55 kDa band | Glycanosyltransferase | ? | XP_749664.1 |
| 3D4 | P2 | 5.88 PAU/L | + | 27 kDa band | Pectate lyase | ? | XP_747393.1 |
| 5B5 | P2 | >100 PAU/L | + | — | Endoglucanase | ? | XP_748349.1 |

Human IgE mAbs for which an *Aspergillus* protein was identified using immunoprecipitation and mass spectrometry are shown. The ImmunoCAP measurements are shown for each IgE mAb along with the approximate protein size if detectable in Western blot. If the protein target has an allergen designation it is listed with the sequence ID.

TABLE E

| | | | IgE hybridoma reactivity | | | | | | | | |
|---|---|---|---|---|---|---|---|---|---|---|---|
| Subject code | IgE Hybridoma | *A. fumigatus* ImmunoCAP (kUA/L) | *A. fumigatus* extract reactivity ELISA | | | | *A. fumigatus* extract reactivity WB | | | | Immuno-precipitation |
| | | | GREER | HS | ALKB | AlrgyL | GREER | HS | ALKB | AlrgyL | |
| P1 | 18F12 | 0.46 | − | − | − | − | − | − | − | − | N/A |
| | 17A5 | 1.84 | − | − | + | − | − | − | + | − | + |
| | 10C4 | 10.2 | − | + | − | + | − | + | − | + | + |
| | 4F8 | 0.16 | − | − | + | − | − | − | + | − | + |
| | 8G2 | 0.28 | − | − | − | − | − | − | − | − | N/A |
| | 20F7 | <0.1 | − | − | − | − | − | − | − | − | N/A |
| | 5E2 | 0.31 | − | − | − | − | − | − | − | − | N/A |
| | 10E8 | 0.36 | − | − | − | − | − | − | − | − | N/A |
| | 5A3 | 0.30 | − | − | − | − | − | − | − | − | N/A |
| | 6G9 | 0.37 | − | − | − | − | − | − | − | − | N/A |
| | 2B3 | <0.1 | − | − | − | − | − | − | − | − | N/A |
| | 15C12 | 2.55 | − | − | − | − | − | − | − | − | ND |
| | 1C9 | 9.39 | + | + | + | + | + | + | + | + | + |
| | 5B7 | 0.16 | − | − | − | − | − | − | − | − | N/A |
| | 7C7 | 0.18 | − | + | + | − | − | − | − | − | N/A |
| P2 | 4D3 | 0.19 | − | − | − | − | − | − | − | − | N/A |
| | 1D3 | 6.51 | + | + | − | + | + | + | − | + | + |
| | 21H12 | 0.21 | − | − | − | − | − | − | − | − | N/A |
| | 12C8 | 5.63 | − | − | − | − | − | − | − | − | ND |
| | 5H12 | 0.50 | − | − | − | − | − | − | − | − | Sorrel |
| | 8D6 | 8.68 | − | − | − | − | − | − | − | − | ND |
| | 16C5 | 0.16 | − | + | + | − | − | − | − | − | ND |
| | 4E12 | 36.2 | + | + | + | + | + | + | − | − | + |
| | 7E9 | 0.12 | − | − | − | − | − | − | − | − | N/A |
| | 1C1 | <0.1 | − | − | − | − | − | − | − | − | N/A |
| | 2C8 | 16.2 | − | − | + | − | − | − | − | − | + |
| | 5C6 | >100 | − | − | + | − | − | + | − | + | + |
| | 12G3 | 0.36 | − | − | − | − | − | − | − | − | N/A |
| | 12G11 | 0.18 | − | − | − | − | − | − | − | − | N/A |
| | 14H4 | 2.99 | − | − | + | − | − | − | + | − | + |
| | 9G9 | 0.33 | − | − | − | − | − | − | − | − | N/A |
| | 13A1 | 0.37 | − | − | − | − | − | − | − | − | N/A |
| | 2G11 | 0.79 | − | − | + | − | − | − | − | − | ND |
| | 18B7 | <0.1 | − | − | − | − | − | − | − | − | N/A |
| | 3H5 | 44.7 | − | − | − | − | − | − | − | − | ND |
| | 24F3 | 0.53 | − | − | − | − | − | − | − | − | N/A |
| | 22H5 | 7.51 | − | − | − | − | − | − | − | − | ND |
| | 21E2 | 6.34 | − | − | + | − | − | + | − | − | + |
| | 15D8 | 0.16 | − | − | − | − | − | − | − | − | N/A |
| | 1C6 | <0.1 | − | − | − | − | − | − | − | − | N/A |
| | 4H4 | 0.30 | − | − | − | − | − | − | − | − | N/A |
| | 19A4 | <0.1 | − | − | − | − | − | − | − | − | N/A |
| | 3D4 | 5.88 | − | − | + | − | − | + | − | − | + |
| | 3F3 | 61.6 | − | − | + | − | − | + | − | − | + |
| | 20H10 | 0.32 | − | − | − | − | − | − | − | − | N/A |
| | 12D6 | 0.30 | − | − | − | − | − | − | − | − | N/A |
| | 5B5 | >100 | + | + | + | + | − | − | − | − | + |
| | 13H5 | 0.38 | − | − | − | − | − | − | − | − | N/A |
| | 8F5 | 0.13 | − | − | − | − | − | − | − | − | N/A |
| | 7B4 | 0.18 | − | − | − | − | − | − | − | − | N/A |
| | 9C3 | >100 | − | + | + | + | − | − | − | − | + |
| | 3F8 | 1.92 | − | − | − | − | − | − | − | − | ND |
| | 13B5 | 0.76 | − | − | − | − | − | − | − | − | N/A |
| P3 | BH1 | 0.42 | − | − | − | − | − | − | − | − | N/A |
| | 10H2 | 0.19 | − | − | − | − | − | − | − | − | N/A |
| | 23H7 | 0.29 | − | − | − | − | − | − | − | − | N/A |
| | 9E1 | 1.63 | − | − | − | − | − | − | − | − | ND |
| | 3B1 | 0.12 | − | − | − | − | − | − | − | − | N/A |
| | 7D4 | 0.44 | − | − | − | − | − | − | − | − | N/A |
| | 21D12 | 0.14 | − | − | − | − | − | − | − | − | N/A |
| | 2H4 | 0.21 | − | − | − | − | − | − | − | − | N/A |
| | 11B1 | 0.45 | − | − | − | − | − | − | − | − | N/A |
| | 5E3 | 0.23 | − | − | − | − | − | − | − | − | N/A |
| | 4C7 | 0.24 | − | − | − | − | − | − | − | − | N/A |
| | 5A9 | 0.22 | − | − | − | − | − | − | − | − | N/A |
| | 19E9 | 0.16 | − | − | − | − | − | − | − | − | N/A |
| | 14G1 | 1.51 | − | − | − | − | − | − | − | − | ND |
| | 11E3 | 1.26 | + | + | + | + | − | − | − | − | ND |

TABLE E-continued

IgE hybridoma reactivity

| Subject code | IgE Hybridoma | A. fumigatus ImmunoCAP (kUA/L) | A. fumigatus extract reactivity ELISA | | | | A. fumigatus extract reactivity WB | | | | Immuno-precipitation |
|---|---|---|---|---|---|---|---|---|---|---|---|
| | | | GREER | HS | ALKB | AlrgyL | GREER | HS | ALKB | AlrgyL | |
| | 14B10 | 0.45 | − | − | − | − | − | − | − | − | N/A |
| | 12F1 | <0.1 | − | − | − | − | − | − | − | − | N/A |

All human IgE mAbs with detectable binding in ImmunoCAP or to commercial extract in ELISA or Western blot are shown for each subject.
*Aspergillus fumigatus* ImmunoCAP was considered positive if >1.0 kUA/L.
IgE mAb binding to *Aspergillus fumigatus* allergenic extracts in ELISA are shown: (−) no binding detected, (+) binding >5 times background.
MAb binding to *Aspergillus fumigatus* allergenic extracts in Western blot are shown: (−) no binding detected, (+) binding detected.
If binding was detected by any method, immunoprecipitation was attempted, listed are the target proteins identified by mass spectrometry.
ND. not determined; N/A. not attempted.

TABLE 1

NUCLEOTIDE SEQUENCES FOR ANTIBODY VARIABLE REGIONS

| Clone | Variable Sequence Region | SEQ ID NO: |
|---|---|---|
| 17A5 heavy | CAGGTGCAGCTGGTGGAGTCTGGGGGAGGCTTGGTCAAGCCTGGGGGGTCCCT GAGACTCTCCTGTGCAGCCTCTGGATTCCCCTTCAGTGATTATCACATGACCTGGA TCCGCCAGGCTCCGGGGAAGGGGCTGGAATGGATTTCACACATCAGTAGTGCTG GCAATAAGATACATTACGCAGAGTCTGTGAAGGGCCGGTTCACCATATCCAGGG ACAACGCCAAGAATTCTCTGTTTCTGCACATGAACAGCCTGAGAGCCGAGGACA CGGCCATGTATTACTGTGCCAGAGATGCGGGATATTATCATGGTTCGGGGAATA ATGCAATTTATCACGGTATGGACGTCTGGGGCCAGGGGACCACGGTCACCGTCT CCTCA | 1 |
| 17A5 light | CAGTCTGTGTTGACGCAGCCGCCCTCAGTGTCTGCGGCCCCAGGACAGAGGGTC ACCATCTCCTGCTCTGGCGGCAGTTCCAACATTGGTTATAATTATGTGGCCTGGTA CCAGCAATTCCCAGGAACAGCCCCCAAACTCCTCCTCTATGACGATGATGAGCGG CCCTCTGGCATTCCTGACCGATTCTCTGGCTCCAGGTCTGGCACGTCAGCCACCCT GGTCATCACCGGACTCCAGACTGGGGACGAGGCCGACTACTACTGCGGAACTTG GGATAGTAGCCTGTCTGTTGTGGTGTTCGGCGGGGGGACCAGGCTGACCGTCCT AG | 2 |
| 14H4 heavy | GAGGTGCAGCTGGTGCAGTCTGGAGCAGAGGTGAAGAGGGCCGGGGAGTCTCT GAAGATCTCCTGTAAGGGTTCTGGATACCCCTTTGCCACCTACTGGGTCGGCTGG GTGCGCCAGATGCCCGGAAAAGGCCTGGAATGGATGACTATCATCTATCCTGAG GACTCCGACACCAGATACAGCCCGTCCTTCCAAGACCATGTCACCATCTCAGCCG ACAAGTCCCTCAGCACCGCCTACCTGCAGTGGAGCAGCCTAAAGGCCTCGGACA CAGCCATGTATTACTGTGCGAGAGTGTCCCGGTATTATTATGATAGTAGAAGTTA TTACCCTGATGCTTTTGACATCTGGGGCCAAGGGACAATGGTCACCGTCTCCTCA G | 3 |
| 14H4 light | TCCTATGAGCTGACTCAGCCACCCTCAGTGTCCGTGTCCCAGGACAGACAGCCA GCATCACCTGCTCTGGAGATAAATTGGGGGATAAATATGTTTGCTGGTATCAACA GAAGCCAGGCCGGTCCCCTGTGTTGGTCGTCCATCAAGATACCAAGCGGCCCTC AGGGATCCCTGAGCGATTCTCTGGCTCCAATTCTGGGGACACAGCCACTCTGACC ATCAGCGGGACCCAGGCTATGGATGAGGCTGACTATTACTGTCAGGCGTGGGAC AGTACCATTGGGTCTTCGGGCCTGGGACCAGGGTCACCGTCCTAG | 4 |
| 4F8 heavy | CAGGTGCAGCTACAGGAGTGGGGCGCAGGACTGTTGAAGCCCTCGGAGACCCT GTCCCTCACCTGCGCTGTCTATGGTGGGTCCTTCAGTGATTACTACTGGAACTGG ATCCGCCAGCCCCCAGGGAAGGGGCTGGAGTGGATTGGAGACATCACTCACAGT GGAGCCACCAACTACAACCCGTCCCTCACGAGTCGAGTCACCTTCTCAGTAGACA TTTCTAAGAACCACTTTTCCTTGAAGCTGACCTCTGTGACCGCCGCGGACACGGC TATGTACTACTGTGCGAGAATAGGAGAAAAAACTGGTGATTATACAATCTGGGG CCAAGGGACAATGGTCACCGTCTCCTCAG | 5 |
| 4F8 light | GCCATCCAGATGACCCAGTCTCCATCGTCCCTGTCTGCATCTATAGGAGACAGAG TCACCATCACTTGCCGGGCAAGTCAGGGCATTAGAAATAATTTAGGCTGGTATCA GCAGGCACCAGGGAAAGCCCCTAGGCTCCTGATCTATGCTGCATCCAGTTTACAA AGTGACGTCCCATCAAGGTTCAGCGGCAGTGGGTCTGGCACAGATTTCACTCTCA CCATCAGCGCCCTGCAGCCTGAAGATTTTGCAACTTATTACTGTCTACAAGACTAC AATTACCCTCGGACGTTCGGCCAAGGGACCAAGGTGGAAATCAAAC | 6 |
| 12C8 heavy | GAGGTGCAGCTGGTGGAGTCTGGGGGAGGCTTGGTCCAGCCGGGGGGGTCCCT GAAACTCTCCTGTGCAGTCTCTGGGTTCAGCGTCAGTGACTCTGCTATACACTGG GTCCGCCAGGCTTCCGGGAAAGGACTGGAGTGGGTAGGCCACATGCGAAGTCA GGCGAACAGTTACGCGACAGCCTATGGTGCGTCGGTGAGAGGCAGGTTCAACAT CTCCAGAGATGACTCAAAGAACACGGCATATCTGCAAATGAACAGCCTGAACAT | 7 |

TABLE 1-continued

NUCLEOTIDE SEQUENCES FOR ANTIBODY VARIABLE REGIONS

| Clone | Variable Sequence Region | SEQ ID NO: |
|---|---|---|
| | CGATGACACGGCCGTATATTATTGTACTAGAAAGGTGGATAATCGACACGGAAT<br>GGACGTCTGGGGCCAAGGGACCACGGTCACCGTCTCCTCA | |
| 12C8 light | TCCTATGTGTTGACGCAGCCTCCCTCTGTGTCAGTGGCCCCAGGACAGACGGCCA<br>GGATTCCCTGTGGGGGAAACAGCATTGGGAGTAGAAGTGTGCACTGGTACCAG<br>CAGAAGCCAGGCCGGGCCCCTGTGTTGGTCATCTATTATGATAGGGACCGGCCC<br>TCGGGGATCCCTGAGCGATTCTCTGGCTCCAACTCTGGGAACACGGCCACCCTGA<br>CCATCGACAGGGTCGAGGCCGGGGATGAGGCCGACTACTACTGTCAGGTGTGG<br>GATGGTAGTAGCGACCAATATGTCTTCGGAATTGGGACCAAGGTCACCGTCCTA | 8 |
| 1C9H | CAGGTGCAGCTGGTGGAGTCTGGGGGAGGCGTGGTCCAGCCTGGGAGGTCCCT<br>GAGACTCTCCTGCGCAGCCTCTGGATTCACCTTCAGCAATTATGCCATGCACTGG<br>GTCCGCCAGGCTCCAGGCAAGGGGCTGGAGTGGGTGGCAGTTATTTCATATGAT<br>GGAAGGAGTGAATTCTATGAAGACTCCGTGAAGGGCCGATTCTCCATCTCCAGA<br>GACAATTCCAAAAGCACGCTGTATCTGCAAATGAACAGCCTGAGAGGTGAGGAC<br>ACCGCTATGTATTACTGTGCGAAACCCGACTCAGCTCTGAACCAATATAGCAGCA<br>GCTGGACCCCTGACTACTGGGGCCAGGGAACCCTGGTCACCGTCTCCTCAG | 42 |
| 1C9L | GATGTTGTGATGACTCAGTCTCCACTCTCCCTGCCCGTCACCCTTGGACAGCCGG<br>CCTCCATCTCCTGCAGGTCTAGTCAGAACCTCGTACACAGTGATGGAAACACCTA<br>CTTGAATTGGTTTCAGCAGAGGCCAGGCCAATCTCCAAGGCGCCTAATTTATAAG<br>TTTTCTAACCGGGACTCTGGGGTCCCAGACAGATTCAGCGGCAGTGGGTCAGGC<br>ACTGATTTCACACTGAAAATCAGCAGGGTGGAGGCTGAGGATGTTGGGGTTTAT<br>TACTGCATGCAAGGTACACACTGGCCTCCGACGTTCGGCCAAGGGACCAAGGTG<br>GAAATCAAAC | 43 |
| 1D3H | CAGGTGCAGCTGGTGGAGTCTGGGGGAGGCGTGGTCCAGCCTGGGAGGTCCGT<br>GAGACTCTCCTGTGAAGCCTCTGGGTTCATGTTCAGAAGTCATGTTCTGCACTGG<br>GTCCGCCAGTCTCCAGGCAAGGGGCTGGAGTGGGTGGCAGTAATTTCATATGAT<br>GGAACAAGTCAATATGTCGCAGACTCCGTGAAGGGCCGGGTCACCGTCTCCAGA<br>GACAATTCCAGGAGCATGATGTTTCTGCAAATGAACAGCCTCAAAAGTGAAGAT<br>ACGGCTGTGTATTACTGTGCAAGAGGGAGGAACGGCTATGGAGGATTTGCTGAC<br>CAGTGGGGCCAGGGAACCCTGGTCACCGTCTCCTCAG | 44 |
| 1D3L | GACATCCAGATGACCCAGTCTCCATCCTCCCTGTCTGCATCTGTGGGAGACAGAG<br>TCACCATCACTTGCCGGCCAAGTCAGAATATTCGCAATTTTTTACATTGGTATCAG<br>CAGAAACCCGGGAAAGCCCCGAGTCTCCTGATTATTCTACATCCAATTTAGAAA<br>GTGGGGTCCCCTCAAGGTTCAGTGGCCGTGGATCTGGGACAGATTTCTCTCTCAC<br>CATCGACGGTCTGCAGCCGGAAGATCTTGCAACTTACTACTGTCAACAGAGTTAC<br>AGTGAATCGTGGACATTCGGCCAAGGGACCAGGGTGGAAATGAAAC | 45 |
| 2C8H | CAGGTGCAGCTGCAGGAGTCGGGCCCAGGACTGGTGAAGCCTTCGGAGACCCT<br>GTCCCTCATTTGCACTGTCTCTGGTGGCTCCCTCAGTAATCACTACTGGAGCTGGA<br>TCCGGCAAACCCCAGGGAAGAAACTGGAGTGGATTGGCTATATCTATTACAGTG<br>GGAGCACCAATTACAACCCTCCCTCAAGAGTCGAGTCACCATGTCAGTAGACAC<br>GTCGCAGAACCAGGTCTCCCTGAACCTGACCTCTGTGACCGCTGCGGACACGGC<br>CATGTATTTCTGTGCGAGAGATAGGGGGAGTGGTTTTGATATCTGGGGCCAGGG<br>GACAGTGGTCACCGTCTCCTCAG | 46 |
| 2C8L | GCCATCCGGATGACCCAGTCTCCATCCTCATTCTCTGCATCTACAGGAGACAGAG<br>TCACCATCACTTGTCGGGCGAGTCAGGATATTAGCTATTTTTTAGCCTGGTATCAG<br>CAAAAACCAGGGAAAGCCCCTGAGTTCCTGATGCATGCTGCATCCACTTTGCAAA<br>GTGGGGTCCCATCAAGGTTCAGCGGCAGTGGCTCTGGGACAGATTTCACTCTCA<br>CCATCAGTAGTCTGCAGTCTGAAGATTCTGCAACTTATTACTGTCAACAGTATTAT<br>ACTTACCCTCCTACGTTCGGCCAAGGGACCAAGGTGGAAATCAAAC | 47 |
| 3D4H | CAGGTGCAGCTGCAGGAGTCGGGCCCAGGACTGGTGAAGCCTTCGGGGACCCT<br>GTCCCTCACCTGCACTGTCTCTGGTGGCTCCATCAGTCATCACTACTGGAGTTGGA<br>TCCGGCAGCCCCCAGGGAGGGGACTGGAGTGGATTGGTTATATCTCTAACAATG<br>AGAGCACCCACTACAGTCCCCCCCTCAAGAGTCGAGTCACCATATCAATTGACGC<br>GTCCAAGAGCCAGTTCTCCCTGAAGCTGACCTCTGTGACCGTTGCTGACACGGCC<br>CTGTATTTCTGTGCGAGAGGCATCCACCTCGACTACATTTCCGTTTTGATGTTTGA<br>CTCCTGGGGCCAGGGAACCCTCGTCACCGTCTCCTCAG | 48 |
| 3D4L | TCCTATGAGCTGACTCAGCCACCCTCAGTGTCCGTGTCCCCAGGACAGACAGCCA<br>GCATCACCTGCTCTGGAGATAGATTGGGGGATAAATATCCTGGTATCAGC<br>AGAAGTCAGGCCAGTCCCTGTCCTGGTCATGTATACGATACCAAGCGGCCCTC<br>TGGGATCCCTGAGCGATTCTCTGGCTCCAACTCTGGGAACACAGCCACTCTGACC<br>ATCAGCGGGACCCAGACTGTGGATGAGGCTGATTATTACTGTCAGGCGTGGGAC<br>AGCAGCACTGAAGTCTTCGGGACTGGGACCAAGGTCTCCGTCCTTG | 49 |
| 3F3H | CAGGTGCAGCTGCAGGAGTCGGGCCCAGGACTGGTGAGGTCTTCAGAGACCCT<br>GTCCCTCACCTGCTCTGTCTCTGGCGCTCCCCATCCGCAGTGGAGATTACTACTGGA<br>ATTGGATGCGCCAGTCCCCCGGGAAGGGCCTGGAATGGATTGGGTACATCTATT<br>ACAGTGGGAGTACCTCCTACACCCCGTCACTCAAGAGTCGACTTTCAATGTCAAT | 50 |

TABLE 1-continued

NUCLEOTIDE SEQUENCES FOR ANTIBODY VARIABLE REGIONS

| Clone | Variable Sequence Region | SEQ ID NO: |
|---|---|---|
| | AGACACGTCCAAGAACCAATTCTCCCTGGAGATGACTTCTGTGACTGCCGCAGAC<br>ACGGCCGTCTATTACTGTGCCAGAGTGGCTTTAAGCGGGTACTTTCTTGACAATT<br>GGGGCCAGGGTGCCCTGGTCACCGTCTCCTCAG | |
| 3F3L | CAGTCTGTGCTGACTCAGCCACCCTCAGTGTCTGGGACCCCCGGGCAGAGGGTC<br>ACTATCTCTTGTTCTGGAAGCAGCTCCAACATCGGAAGAAATTATGTATATTGGT<br>ACTACCAGCTCCCAGGAACGGCCCCCAAGGTCCTCATGTATAAGAATAATCAGCG<br>GCCCTCAGGGGTCCCTGACCGATTCTCTGGCTCCAAGTCTGGCACTTCAGCCTCC<br>CTGGCCATCAGCGGGCTCCGGTCCGAAGATGAGGCTGATTATTACTGTGCAGCG<br>TGGGATGACAGCCTGAGTGGTCATGTCTTCGGAAGTGGGACCAAGGTCACCGTC<br>CTAG | 51 |
| 4E12H | CAGGTGCAGCTGGTGGAGTCTGGGGGAGGCGTGGTCCAGCCTGGGAGGTCCTT<br>GAGACTCTCTTGTGGAGCGTCTGGATTCACCTTCAGACAATATGGCATGCACTGG<br>GTCCGCCAGGCTCCAGGCAAGGGGCTGGAGTGGGTGGCAGTTATTTGGTTCGAC<br>GGAAGTAAGGAATATTATGTCGACTCCGTGAAGGGCCGTTTCACCATCTCCAGA<br>GACAACTCCAAGAATACGCTCTTTTTGCAAATGAACAGCCTGAGAGCCGAGGAC<br>ACGGCTGTGTATTTTTGTGTGAGAGATGGTCCTCTCGGCGACAGCAGTGGGACC<br>TCTTTGGACGTCTGGGGCCAAGGGACCACGGTCACCGTCTCCTCAG | 52 |
| 4E12L | TCTTCTGAGCTGACTCAGGACCCTGCTGTGTCTGTGGCCTTGGGACAGACAGTCA<br>GGATTACATGCCGAGGAGACAGCCTCAGATACTATTATGCAAGCTGGTACCAGC<br>AGAAGCCAGGACAGGCCCCTCTTCTTGTCGTCTATGGTAAAAACAACCGGCCCTC<br>AGGAATCCCAGACCGGTTCTCTGGCTCCACCTCAGGAAACACAGCTTCCTTGACC<br>ATCACTGGGGCTCAGGCGGAAGATGAGGCTGACTATTACTGTGACTCCCGGGAC<br>AGTAGTGGTTTCCATCACGATGTTTTCTTCGGCGGAGGGACCAGATTGACCGTCC<br>TAG | 53 |
| 5B5H | CAGGTGCAGCTGCAGGAGTCGGGCCCAGGACTGGTGAAGCCTTCGCAGACCCT<br>GTCCCTCACCTGCTCTGTCTCTGGTGGCGCCATTAGAAGTGATGGCAACGACTGC<br>AGGTGGACCTGGATCCGGCAGCCCGCCGGGAAGGGACTGGAGTGGCTTGGGCG<br>TGTCTCTTCCAGTGGGAGCACCAGCTACAACCCCTCCCTCAAGAGTCGACTCACC<br>ATGTCGATAGACTCGTCCAAGAACCTCCTCTCCCTGAGGCTGACCTCTGTGACCG<br>CCGCAGACACGGCCGTCTATTACTGTGCGAGAGAGGACGACTTTAATGCTAGTG<br>ATTTTTACCGTAGGAATTACTTCCCCGCTCTGGACGTCTGGGGCCGGGGGACTAT<br>GGTCACCGTCTCCTCA | 54 |
| 5B5L | GACATCCAGATGACCCAGTCTCCATCGTCGCTGTCTGCATCTGTAGGGGACAGTG<br>TCACCATCACTTGTCGGGCAAGCCAGAGAATCGGCAATTATTTAAATTGGTATCA<br>GCACAAGCCAGGGAAAGCCCCTAAACTCCTGATATATGCTACATCCCGTTTGCAC<br>CGTGGGGTCCCATCCAGGTTCAGTGGCGGTGGATCTGGGACAGAATTCACTCTC<br>ACTATCAAGACTCTCTTGCCTGAAGATTTTGCAACTTATTTCTGTCAACAGACTTTC<br>GGTGCCCCTCCGTGGACGTTCGGCCAGGGGACCAAGGTTGAAGCCCGAC | 55 |
| 5C6H | CAGGTGCAGCTGCAGGAGTCGGGCCCAAGATTGGTGAGGCCTTCAGAGACCCT<br>GTCCCTCACCTGCACTGTCTCTGGTGGCTCGATCAGCGATACCAATTACCATTGG<br>AGTTGGGTCCGCCAGCCCCCGGGGAAGGGCCTGGAGTGGATTGGATACATCTAT<br>TACAGCGGGGTTCTCATACTCCACCCCGTCCCTCAAGGGTCGAGTTACCATATCAAT<br>AGACATGTCCAAGAACCAGTTCTCCTTGAAGCTGACCTCTGTGTCGGCCGCAGAC<br>ACGGCCGTCTATTTCTGTGCCAGAGACCCCATCTCTTACGCTAATGGTGTCTTTGA<br>CTTCTGGGGCCAGGGAGCCCTGGTCACCGTCTCCTCAG | 56 |
| 5C6L | GACATCCAGATGACCCAGTCTCCATCCTCCCTGTCTGCATCTGTCGGAGACAGAG<br>TCACCATCACTTGCCGGGCAAGTCAGGGCCTTAGAAATAATTTAGGCTGGTATCA<br>GCAGAAGCAGGGCAAGCCCCTAAGCGCCTGATCTATGCTGCTTCCAAGTTACA<br>AGATGGGGTCCCATTGAGGTTCAGCGGCAATGGATCTGGGACAGAATTCACTCT<br>CACGATCCACAGCCTGCAGCCTGAGGATTTTGCAACTTACTACTGTCTACAGCAT<br>AATAGTTTTCCTCGCACGTTCGGCCAAGGGACCCAGGTGGAAGTCAAAC | 57 |
| 9C3H | CAGCTGCAGCTGCAGGAGTCGGGCCCAGGACTGGTGAAGCCTTCGGAGACCCT<br>GTCCCTCACCTGCACTGTCTCTGGTGGCTCTTTCACCAGCACCAGTTACTACTGGG<br>ACTGGATCCGCCAGCCCCAGGGAAGGGGCTGGAGTGGATTGGAGTATCTATT<br>ATAGTGGGAGCACCTACTATAACCCGTCCCTCAAGAGTCGACTCACCATATCCGT<br>AGACAGTTCCAAGAACCAGTTCTCCCTGAAGCTGACCTCTGTGACCGCCGCAGAC<br>ACGGCTGTCTATTACTGTGCGAGACATGAGAAGCAGTTGGACAGACTTGACTCCT<br>GGGGCCAGGGAACCCTGGTAACCGTCTCCTCAG | 58 |
| 9C3L | GACATCCAGATGACCCAGTCTCCATCCTCCCTGTCTGCATCTGTAGGAGACAGAG<br>TCACCATCACTTGCCGGGCAAGTCAGAGCATCTCCACCTATTTACATTGGTATCAG<br>CAGAAACCAGGAAAGCCCCTGAGCTCCTGATCTATGCTGCATCCACTTTGCAAA<br>GTGGGGTCCCATCAAGGTTCAGTGGCAGTGGATCTCGGACAGATTTCACTCTCAC<br>CATCAGCAGTCTGCAACCTGAAGATTTTGCAACTTACTACTGTCAACAGAGTTAC<br>AGTACCGTCCTCACTTTCGGCGGAGGGACCAAGGTGGAGATCAAGC | 59 |

TABLE 1-continued

NUCLEOTIDE SEQUENCES FOR ANTIBODY VARIABLE REGIONS

| Clone | Variable Sequence Region | SEQ ID NO: |
|---|---|---|
| 10C4H | GAGGTGCAGCTGGTGCAGTCTGGAGCAGAGGTGAAAAAGCCGGGGGAGTCTCT GAAGATTTCCTGTAAGGCTTCTGGATACACCTTTACCAACTACTGGATCGGCTGG GTGCGCCAGATGCCCGGGAAAGGCCTGGAGTGGATGGGAATCGTCTATGGTGG TGGTTCTGCGACCACCTACAACCCGTCCTTCCAAGGCCGGGTCACCATCTCCGCC GACAAGTCCATCAGCACCGCCTACTTGGAGTGGAGCAGCCTGGAGGCCTCGGAC ACCGCCATGTATTACTGTGCGCGACATGTAGGTGGAGGATATAGTGGCTCCGGA TACTACTACTTCTATAGTCTGGATGTCTGGGGCCAAGGGACCACGGTCACCGTCT CCTCA | 60 |
| 10C4L | GAAATTGTGTTGACACAGTCTCCGGGCACCCTGTCTTTGTCTCCAGGGGACAGCG CCACCCTCTCCTGCAGGGCCAGTCAGGGTCTTACCAGCAACTACTTAGCCTGGTA CCAGCAGAGACCTGGCCAGGCTCCCAGGCTCCTCATCTATGGTGCATCCAGAAG GGCCACTGGCATCCCAGACAGGTTCAGTGGCAGTGGGTCTGGGACAGACTTCAC TGTCACCATCAGTCGACTGGAGCCTGAAGATTTTGCAGTGTATTATTGTCAGTAC TATGGTACCTCACCTCCGCCTTTCGGCGGAGGGACCAAGGTGGAGATCAAAC | 61 |

TABLE 2

PROTEIN SEQUENCES FOR ANTIBODY VARIABLE REGIONS

| Clone | Variable Sequence | SEQ ID NO. |
|---|---|---|
| 17A5 heavy | QVQLVESGGGLVKPGGSLRLSCAASGFPFSDYHMTWIRQAPGKGLEWISHISSAGN KIHYAESVKGRFTISRDNAKNSLFLHMNSLRAEDTAMYYCARDAGYYHGSGNNAIY HGMDVWGQGTTVTVSS | 9 |
| 17A5 light | QSVLTQPPSVSAAPGQRVTISCSGGSSNIGYNYVAWYQQFPGTAPKLLLYDDDERPS GIPDRFSGSRSGTSATLVITGLQTGDEADYYCGTWDSSLSVVVFGGGTRLTVL | 10 |
| 14H4 heavy | EVQLVQSGAEVKRAGESLKISCKGSGYPFATYWVGWVRQMPGKGLEWMTIIYPED SDTRYSPSFQDHVTISADKSLSTAYLQWSSLKASDTAMYYCARVSRYYYDSRSYYPDA FDIWGQGTMVTVSS | 11 |
| 14H4 light | SYELTQPPSVSVSPGQTASITCSGDKLGDKYVCWYQQKPGRSPVLVVHQDTKRPSGI PERFSGSNSGDTATLTISGTQAMDEADYYCQAWDSTIGVFGPGTRVTVL | 12 |
| 4F8 heavy | QVQLQEWGAGLLKPSETLSLTCAVYGGSFSDYYWNWIRQPPGKGLEWIGDITHSG ATNYNPSLTSRVTFSVDISKNHFSLKLTSVTAADTAMYYCARIGEKTGDYTIWGQGT MVTVSS | 13 |
| 4F8 light | AIQMTQSPSSLSASIGDRVTITCRASQGIRNNLGWYQQAPGKAPRLLIYAASSLQSDV PSRFSGSGSGTDFTLTISALQPEDFATYYCLQDYNYPRTFGQGTKVEIK | 14 |
| 12C8 heavy | EVQLVESGGGLVQPGGSLKLSCAVSGFSVSDSAIHWVRQASGKGLEWVGHMRSQA NSYATAYGASVRGRFNISRDDSKNTAYLQMNSLNIDDTAVYYCTR | 15 |
| 12C8 light | SYVLTQPPSVSVAPGQTARIPCGGNSIGSRSVHWYQQKPGRAPVLVIYYDRDRPSGI PERFSGSNSGNTATLTIDRVEAGDEADYYCQVWDGSSD | 16 |
| 1C9H | QVQLVESGGGVVQPGRSLRLSCAASGFTFSNYAMHWVRQAPGKGLEWVAVISYDGRSEF YEDSVKGRFSISRDNSKSTLYLQMNSLRGEDTAMYYCA | 62 |
| 1C9L | DVVMTQSPLSLPVTLGQPASISCRSSQNLVHSDGNTYLNWFQQRPGQSPRRLIYKFSNRDS GVPDRFSGSGSGTDFTLKISRVEAEDVGVYYCMQGTHWP | 63 |
| 1D3H | QVQLVESGGGVVQPGRSVRLSCEASGFMFRSHVLHWVRQSPGKGLEWVAVISYDGTSQY VADSVKGRVTVSRDNSRSMMFLQMNSLKSEDTAVYYCAR | 64 |
| 1D3L | DIQMTQSPSSLSASVGDRVTITCRPSCINIRNFLHWYQQKPGKAPSLLIYSTSNLESGVPSRFS GRGSGTDFSLTIDGLOPEDLATYYCQQSYS | 65 |
| 2C8H | QVQLQESGPGLVKPSETLSLICTVSGGSLSNHYWSWIRQTPGKKLEWIGYIYYSGSTNYNPS LKSRVTMSVDTSQNQVSLNLTSVTAADTAMYFCAR | 66 |
| 2C8L | AIRMTQSPSSFSASTGDRVTITCRASQDISYFLAWYQQKPGKAPEFLMHAASTLQSGVPSR FSGSGSGTDFTLTISSLQSEDSATYYCQQYYTYP | 67 |
| 3D4H | QVQLQESGPGLVKPSGTLSLTCTVSGGSISHHYWSWIRQPPGRGLEWIGYISNNESTHYSP PLKSRVTISIDASKSQFSLKLTSVTVADTALYFCAR | 68 |

TABLE 2-continued

PROTEIN SEQUENCES FOR ANTIBODY VARIABLE REGIONS

| Clone | Variable Sequence | SEQ ID NO. |
|---|---|---|
| 3D4L | SYELTQPPSVSVSPGQTASITCSGDRLGDKYTSWYQQKSGQSPVLVMYHDTKRPSGIPERF SGSNSGNTATLTISGTQTVDEADYYCQAWDSST | 69 |
| 3F3H | QVQLQESGPGLVRSSETLSLTCSVSGVPIRSGDYYWNWMRQSPGKGLEWIGYIYYSGSTSY TPSLKSRLSMSIDTSKNQFSLEMTSVTAADTAVYYCAR | 70 |
| 3F3L | QSVLTQPPSVSGTPGQRVTISCSGSSSNIGRNYVYWYYQLPGTAPKVLMYKNNQRPSGVP DRFSGSKSGTSASLAISGLRSEDEADYYCAAWDDSLSG | 71 |
| 4E12H | QVQLVESGGGVVQPGRSLRLSCGASGFTFRQYGMHWVRQAPGKGLEWVAVIWFDGSKE YYVDSVKGRFTISRDNSKNTLFLQMNSLRAEDTAVYFCVR | 72 |
| 4E12L | SSELTQDPAVSVALGQTVRITCRGDSLRYYYASWYQQKPGQAPLLVVYGKNNRPSGIPDRF SGSTSGNTASLTITGAQAEDEADYYCDSRDSSGFH | 73 |
| 5B5H | QESGPGLVKPSQTLSLTCSVSGGAIRSDGNDCRWTWIRQPAGKGLEWLGRVSSSGSTSYN PSLKSRLTMSIDSSKNLLSLRLTSVTAADTAVYYCAR | 74 |
| 5B5L | DIQMTQSPSSLSASVGDSVTITCRASQRIGNYLNWYQHKPGKAPKLLIYATSRLHRGVPSRF SGGGSGTEFTLTIKTLLPEDFATYFCQQTFGAP | 75 |
| 5C6H | QVQLQESGPRLVRPSETLSLTCTVSGGSISDTNYHWSWVRQPPGKGLEWIGYIYYSGFSYST PSLKGRVTISIDMSKNQFSLKLTSVSAADTAVYFCAR | 76 |
| 5C6L | DIQMTQSPSSLSASVGDRVTITCRASQGLRNNLGWYQQKPGQAPKRLIYAASKLQDGVPL RFSGNGSGTEFTLTIHSLQPEDFATYYCLQHNSFP | 77 |
| 9C3H | QLQLQESGPGLVKPSETLSLTCTVSGGSFTSTSYYWDWIRQPPGKGLEWIGSIYYSGSTYYN PSLKSRLTISVDSSKNQFSLKLTSVTAADTAVYYCAR | 78 |
| 9C3L | DIQMTQSPSSLSASVGDRVTITCRASQSISTYLHWYQQKPGKAPELLIYAASTLQSGVPSRFS GSGSRTDFTLTISSLQPEDFATYYCQQSYST | 79 |
| 10C4H | EVQLVQSGAEVKKPGESLKISCKASGYTFTNYWIGWVRQMPGKGLEWMGIVYGGGSATT YNPSFQGRVTISADKSISTAYLEWSSLEASDTAMYYCAR | 80 |
| 10C4L | EIVLTQSPGTLSLSPGDSATLSCRASQGLTSNYLAWYQQRPGQAPRLLIYGASRRATGIPDRF SGSGSGTDFTVTISRLEPEDFAVYYCQYYGTSP | 81 |

TABLE 3

CDR HEAVY CHAIN SEQUENCES

| Antibody Clone | CDRH1 (SEQ ID NO:) | CDRH2 (SEQID NO:) | CDRH3 (SEQ ID NO:) |
|---|---|---|---|
| 17A5 | GFPFSDYH (17) | ISSAGNKI (18) | ARDAGYYHGSGNNAIYHGMDV (19) |
| 14H4 | GYPFATYW (20) | IYPEDSDT (21) | ARVSRYYYDSRSYYPDAFDI (22) |
| 4F8 | GGSFSDYY (23) | ITHSGAT (24) | ARIGEKTGDYTI (25) |
| 12C8 | GFSVSDSA (26) | MRSCIANSYAT (27) | TRKVDNRHGMDV (28) |
| 1C9 | GFTFSNYA (82) | ISYDGRSE (83) | AKPDSALNQYSSSVVTPDY (84) |
| 1D3 | GFMFRSHV (85) | ISYDGTSQ (86) | ARGRNGYGGFADQ (87) |
| 2C8 | GGSLSNHY (88) | IYYSGST (89) | ARDRGSGFDI (90) |
| 3D4 | GGSISHHY (91) | ISNNEST (92) | ARGIHLDYISVLMFDS (93) |

TABLE 3-continued

CDR HEAVY CHAIN SEQUENCES

| Antibody | CDRH1 (SEQ ID NO: ) | CDRH2 (SEQID NO: ) | CDRH3 (SEQ ID NO: ) |
|---|---|---|---|
| 3F3 | GVPIRSGDYY (94) | IYYSGST (95) | ARVALSGYFLDN (96) |
| 4E12 | GFTFRQYG (97) | IWFDGSKE (98) | VRDGPLGDSSGTSLDV (99) |
| 5B5 | RSDGNDCR (100) | VSSSGST (101) | AREDDFNASDFYRRNYFPALDV (102) |
| 5C6 | GGSISDTNYH (103) | IYYSGFS (104) | ARDPISYANGVFDF (105) |
| 9C3 | GGSFTSTSYY (106) | IYYSGST (107) | ARHEKQLDRLDS (108) |
| 10C4 | GYTFTNYW (109) | VYGGGSAT (110) | ARHVGGYSGSGYYYFYSLDV (111) |

TABLE 4

CDR LIGHT CHAIN SEQUENCES

| Antibody | CDRH1 (SEQ ID NO: ) | CDRH2 (SEQ ID NO:) | CDRH3 (SEQ ID NO: ) |
|---|---|---|---|
| Clone | | | |
| 17A5 | SSNIGYNY (29) | GTWDSSLSVVV (30) | [Not available] (31) |
| 14H4 | KLGDKY (32) | QAWDSTIGV (33) | [Not available] (34) |
| 4F8 | QGIRNN (35) | LQDYNYPRT (36) | [Not available] (37) |
| 12C8 | SIGSRS (38) | YDR | QVWDGSSDQYV (39) |
| 1C9 | QNLVHSDGNTY (112) | KFS | MQGTHWPPT (113) |
| 1D3 | QNIRNF (114) | STS | QQSYSESWT (115) |
| 2C8 | QDISYF (116) | AAS | QQYYTYPPT (117) |
| 3D4 | RLGDKY (118) | HDT | QAWDSSTEV (119) |
| 3F3 | SSNIGRNY (120) | KNN | AAWDDSLSGHV (121) |
| 4E12 | SLRYYY (122) | GKN | DSRDSSGFHHDVF (123) |
| 5B5 | QRIGNY (124) | ATS | QQTFGAPPWT (125) |
| 5C6 | QGLRNN (126) | AAS | LQHNSFPRT (127) |
| 9C3 | QSISTY (128) | AAS | QQSYSTVLT (129) |
| 10C4 | QGLTSNY (130) | GAS | QYYGTSPPP (131) |

All of the compositions and methods disclosed and claimed herein can be made and executed without undue experimentation in light of the present disclosure. While the compositions and methods of this disclosure have been described in terms of preferred embodiments, it will be apparent to those of skill in the art that variations may be applied to the compositions and methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

VII. REFERENCES

The following references, to the extent that they provide exemplary procedural or other details supplementary to those set forth herein, are specifically incorporated herein by reference.

U.S. Pat. No. 3,817,837
U.S. Pat. No. 3,850,752
U.S. Pat. No. 3,939,350
U.S. Pat. No. 3,996,345
U.S. Pat. No. 4,196,265
U.S. Pat. No. 4,275,149
U.S. Pat. No. 4,277,437
U.S. Pat. No. 4,366,241
U.S. Pat. No. 4,472,509
U.S. Pat. No. 4,554,101
U.S. Pat. No. 4,680,338
U.S. Pat. No. 4,816,567
U.S. Pat. No. 4,867,973
U.S. Pat. No. 4,938,948
U.S. Pat. No. 5,021,236
U.S. Pat. No. 5,141,648
U.S. Pat. No. 5,196,066
U.S. Pat. No. 5,563,250
U.S. Pat. No. 5,565,332
U.S. Pat. No. 5,856,456
U.S. Pat. No. 5,880,270
U.S. Pat. No. 6,485,982
"Antibodies: A Laboratory Manual," Cold Spring Harbor Press, Cold Spring Harbor, N.Y., 1988.
Abbondanzo et al., *Am. J. Pediatr. Hematol. Oncol.*, 12(4), 480-489, 1990.
Allred et al., *Arch. Surg.*, 125(1), 107-113, 1990.
Atherton et al., *Biol. of Reproduction*, 32, 155-171, 1985.
Barzon et al., *Euro Surveill.* 2016 Aug. 11; 21(32).
Beltramello et al., *Cell Host Microbe* 8, 271-283, 2010.
Brown et al., *J. Immunol. Meth.*, 12; 130(1): 111-121, 1990.
Campbell, In: *Monoclonal Antibody Technology, Laboratory Techniques in Biochemistry and Molecular Biology*, Vol. 13, Burden and Von Knippenberg, Eds. pp. 75-83, Amsterdam, Elsevier, 1984.
Capaldi et al., *Biochem. Biophys. Res. Comm.*, 74(2):425-433, 1977.
De Jager et al., *Semin. Nucl. Med.* 23(2), 165-179, 1993.
Dholakia et al., *J. Biol. Chem.*, 264, 20638-20642, 1989.
Diamond et al., *J Virol* 77, 2578-2586, 2003.
Doolittle and Ben-Zeev, *Methods Mol. Biol.*, 109: 215-237, 1999.
Duffy et al., *N. Engl. J. Med.* 360, 2536-2543, 2009.
Elder et al. Infections, infertility and assisted reproduction. Part II: Infections in reproductive medicine & Part III: Infections and the assisted reproductive laboratory. Cambridge UK: Cambridge University Press; 2005.
Gefter et al., *Somatic Cell Genet.*, 3:231-236, 1977.
Gornet et al., *Semin Reprod Med.* 2016 September; 34(5): 285-292. Epub 2016 Sep. 14.
Gulbis and Galand, *Hum. Pathol.* 24(12), 1271-1285, 1993.
Halfon et al., *PLoS ONE* 2010; 5 (5) e10569
Hessell et al., *Nature* 449, 101-4, 2007.
Khatoon et al., *Ann. of Neurology*, 26, 210-219, 1989.
King et al., *J. Biol. Chem.*, 269, 10210-10218, 1989.
Kohler and Milstein, *Eur. J. Immunol.*, 6, 511-519, 1976.
Kohler and Milstein, *Nature*, 256, 495-497, 1975.
Kyte and Doolittle, *J. Mol. Biol.*, 157(1):105-132, 1982.
Mansuy et al., *Lancet Infect Dis.* 2016 October; 16(10): 1106-7.
Nakamura et al., In: *Enzyme Immunoassays: Heterogeneous and Homogeneous Systems*, Chapter 27, 1987.
O'Shannessy et al., *J. Immun. Meth.*, 99, 153-161, 1987.
Persic et al., *Gene* 187:1, 1997
Potter and Haley, *Meth. Enzymol.*, 91, 613-633, 1983.
Purpura et al., *Lancet Infect Dis.* 2016 Oct.; 16(10):1107-8. Epub 2016 Sep. 19.
Remington's Pharmaceutical Sciences, 15th Ed., 3:624-652, 1990.
Tang et al., *J. Biol. Chem.*, 271:28324-28330, 1996.
Wawrzynczak & Thorpe, In: *Immunoconjugates, Antibody Conjugates In Radioimaging And Therapy Of Cancer*, Vogel (Ed.), NY, Oxford University Press, 28, 1987.
Yu et al., *J Immunol Methods* 336, 142-151, doi:10.1016/j.jim.2008.04.008, 2008.
Abraham et al., *Infect Immun.*; 72:810-7, 2004.
Acevedo et al., *Allergy*, 64(11):1635-43, 2009.
American Academy of Allergy Asthma and Immunology: Food allergy. World-wide-web at aaaai.org/conditions-and-treatments/allergies/food-allergies.aspx
Casaulta C, Fluckiger S, Crameri R, Blaser K, Schoeni M H. *Pediatr Allergy Immunol.* 2005; 16(3):217-225.
Chapa-Ruiz et al., *Parasite;* 8: S163-7, 2001.
Chowdhary et al., *Crit Rev Microbiol.* 2014; 40(1):30-48.
Cooper et al., *J Allergy Clin Immunol.*, 111:995-1000, 2003.
Cruz et al., *Clin Exp Allergy;* 37:197-207, 2007.
Dombrowicz et al., *J Immunol.* 1996; 157(4):1645-1651.
Dreborg et al., *Allergy.* 1986; 41(2):131-140.
Emiralioglu et al., *Ann Pharmacother.* 2016; 50(3):188-193.
Esch R E, Codina R. *Ann Allergy Asthma Immunol.* 2017; 118(4):399-405.
Esch R E. *J Allergy Clin Immunol.* 2004; 113(2):210-215.
Finkelman, et al., *Immunol. Rev.;* 201:139-155, 2004.
Gautam et al., *Clin Exp Allergy.* 2007; 37(8):1239-1249.
Greenberger et al., *J Allergy Clin Immunol Pract.* 2014; 2(6):703-708.
Gurish et al., *J Immunol.;* 172:1139-45, 2004.
Hagan et al., *Nature*, 349:243-245, 1991.
Hagel et al., *Acta Trop.*, 103:231-241, 2007.
Herbert et al., *Immunity;* 20:623-635, 2004.
Horst M, Hejjaoui A, Horst V, Michel F B, Bousquet J. *J Allergy Clin Immunol.* 1990; 85(2):460-472.
Johansson and Bennich, *Immunology;* 13(4):381-94, 1967.
King et al., *J Immunol;* 158:294-300, 1997.
Lee et al., *J Infect Dis.*, 162:529-33, 1990.
Leonardi-Bee et al., *Am J Respir Crit Care Med.*, 174:514-523, 2006.
Liu and Leung, *J Allergy Clin Immunol.*, 117:1063-1066, 2006.
Lobos et al., *Mol Med.*, 2(6):712-24, 1996.

McCarthy et al., *J Infect Dis.*, 170:736-41, 1994.
McSharry et al., *Infect Immun;* 67:484-489, 1999.
Nikolaizik W H, Weichel M, Blaser K, Crameri R. *Am J Respir Crit Care Med.* 2002; 165(7):916-921.
Nutman et al., *J. Infect. Dis.;* 160:1042-1050, 1989.
Olsson and Kaplan, *Proc Natl Acad Sci USA;* 77(9):5429-31, 1980.
Oettgen H C, Burton O T. *Curr Opin Immunol.* 2015; 36:109-114.
Rodrigues et al., *Clin Exp Allergy;* 38:1769-1777, 2008.
Santiago et al., *J Immunol.*, 194(1):93-100, 2015.
Santiago et al., *J Allergy Clin Immunol.*, 130(1):248-56, 2012.
Santiago et al., *PLoS One,* 7(7):e40552, 2012.
Sicherer et al., *J Allergy Clin Immunol.*, April; 103(4):559-62, 1999.
Smith et al., *J Virol.* 2012; 86(5):2665-2675.
Smith S A and Crowe J E Jr. *Microbiol Spectr.* 2015; 3(1):AID-0027-2014.
Strachan, *BMJ,* 299:1259-1260, 1989.
Sze et al., *Cell Chem Biol.* 2017; 24(2):182-194.
Turner et al., *J Infect Dis.*, 188:1768-1775, 2003.
Turner et al., *Microbes Infect.*, 7:990-996, 2005.
Vailes et al., *J Allergy Clin Immunol.* 2001; 107(4):641-646.
van den Biggelaar et al., Lancet.; 356:1723-1727, 2000.
Voskamp et al., *J Allergy Clin Immunol Pract.* 2015; 3(2): 192-199.
Voehringer et al., J. Exp. Med., 203:1435-1446, 2006.
Wordemann et al., Trop Med Int Health.; 13:180-186, 2008.

What is claimed is:

1. A monoclonal antibody, wherein the antibody or antibody fragment is characterized by heavy and light chain CDR1, CDR2 and CDR3 sequences of SEQ ID NOS: 17, 18 and 19 and SEQ ID NOS: 29, 30 and 31, respectively.

2. The monoclonal antibody of claim 1, wherein said antibody or antibody fragment is encoded by light and heavy chain variable sequences SEQ ID NO: 2 and SEQ ID NO: 1, respectively.

3. The monoclonal antibody of claim 1, wherein said antibody or antibody fragment is encoded by light and heavy chain variable sequences having at least 70%, 80%, or 90% identity to SEQ ID NO: 2 and SEQ ID NO: 1, respectively.

4. The monoclonal antibody of claim 1, wherein said antibody or antibody fragment is encoded by light and heavy chain variable sequences having at least 95% identity to SEQ ID NO: 2 and SEQ ID NO: 1, respectively.

5. The monoclonal antibody of claim 1, wherein said antibody or antibody fragment comprises light and heavy chain variable sequences SEQ ID NO: 10 and SEQ ID NO: 9, respectively.

6. The monoclonal antibody of claim 1, wherein said antibody or antibody fragment comprises light and heavy chain variable sequences having 95% identity to SEQ ID NO: 10 and SEQ ID NO: 9, respectively.

7. The monoclonal antibody of claim 1, wherein the antibody fragment is a recombinant scFv (single chain fragment variable) antibody, Fab fragment, F(ab')$_2$ fragment, or Fv fragment.

8. The monoclonal antibody of claim 1, wherein said antibody is a chimeric antibody, or is bispecific antibody.

9. The monoclonal antibody of claim 1, wherein said antibody is a recombinant IgG antibody or antibody fragment.

10. The monoclonal antibody of claim 9, wherein the recombinant IgG or IgG fragment comprises an Fc portion carrying a LALA, N297, GASD/ALIE, YTE or LS mutation.

11. The monoclonal antibody of claim 9, wherein the recombinant IgG or IgG fragment comprises a glycan modification selected from enzymatic or chemical addition or removal of glycans or that result from expression in a cell line engineered with a defined glycosylating pattern.

12. The monoclonal antibody of claim 1, wherein said antibody or antibody fragment further comprises a cell penetrating peptide and/or is an intrabody.

13. A method of producing an IgG immune response to an *Aspergillus* allergen comprising:
   (a) identifying an IgE epitope in an allergen by mapping the binding of an IgE antibody binding site, wherein said antibody has clone-paired heavy and light chain CDR1, CDR2 and CDR3 sequences of SEQ ID NOS: 17, 18 and 19 and SEQ ID NOS: 29, 30 and 31, respectively;
   (b) modifying one or more residues in said IgE antibody binding site to reduce or eliminate IgE antibody binding to said binding site, thereby producing a hypoallergenic *Aspergillus* allergen;
   (c) immunizing a subject with said hypoallergenic *Aspergillus* allergen to produce and IgG response to said hypoallergenic *Aspergillus* allergen, while producing a reduced or no IgE response as compared to the allergen of step (a).

* * * * *